(12) United States Patent
Shair et al.

(10) Patent No.: US 10,273,264 B2
(45) Date of Patent: Apr. 30, 2019

(54) CORTISTATIN ANALOGUES AND SYNTHESES AND USES THEREOF

(71) Applicant: President and Fellows of Harvard College, Cambridge, MA (US)

(72) Inventors: Matthew D. Shair, Lexington, MA (US); Henry Efrem Pelish, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/852,178

(22) Filed: Dec. 22, 2017

(65) Prior Publication Data

US 2018/0118778 A1  May 3, 2018

Related U.S. Application Data

(63) Continuation of application No. PCT/US2016/040482, filed on Jun. 30, 2016.

(60) Provisional application No. 62/187,696, filed on Jul. 1, 2015.

(51) Int. Cl.
- C07J 71/00 (2006.01)
- C07D 493/08 (2006.01)
- A61P 35/00 (2006.01)

(52) U.S. Cl.
CPC .......... C07J 71/0005 (2013.01); A61P 35/00 (2018.01); C07D 493/08 (2013.01)

(58) Field of Classification Search
None
See application file for complete search history.

(56) References Cited

U.S. PATENT DOCUMENTS

| | | | |
|---|---|---|---|
| 2,886,589 A | 5/1959 | Novello et al. | |
| 4,853,224 A | 8/1989 | Wong | |
| 4,863,457 A | 9/1989 | Lee | |
| 4,997,652 A | 3/1991 | Wong | |
| 5,098,443 A | 3/1992 | Parel et al. | |
| 5,185,152 A | 2/1993 | Peyman | |
| 5,378,475 A | 1/1995 | Smith et al. | |
| 5,410,016 A | 4/1995 | Hubbell et al. | |
| 5,443,505 A | 8/1995 | Wong et al. | |
| 5,554,187 A | 9/1996 | Rizzo, III | |
| 5,710,182 A | 1/1998 | Reunamaki et al. | |
| 5,725,493 A | 3/1998 | Avery et al. | |
| 6,177,095 B1 | 1/2001 | Sawhney et al. | |
| 6,632,457 B1 | 10/2003 | Sawhney | |
| 6,803,031 B2 | 10/2004 | Rabinowitz et al. | |
| 8,642,766 B2 | 2/2014 | Shenvi et al. | |
| 8,791,263 B2 | 7/2014 | Kobayashi et al. | |
| 9,127,019 B2 | 9/2015 | Flyer et al. | |
| 9,714,255 B2 | 7/2017 | Flyer et al. | |
| 2003/0060425 A1 | 3/2003 | Ahlem et al. | |
| 2003/0149287 A1 | 8/2003 | Zasloff et al. | |
| 2004/0220161 A1 | 11/2004 | Ahlem et al. | |
| 2005/0014737 A1 | 1/2005 | Agoston et al. | |
| 2006/0014727 A1 | 1/2006 | Karsan et al. | |
| 2006/0094696 A1 | 5/2006 | Leese et al. | |
| 2007/0004689 A1 | 1/2007 | Agoston et al. | |
| 2007/0225256 A1 | 9/2007 | Leese et al. | |
| 2009/0023666 A1 | 1/2009 | Gardiner et al. | |
| 2010/0168141 A1 | 7/2010 | Evans et al. | |
| 2011/0190323 A1 | 8/2011 | Flyer et al. | |
| 2012/0083484 A1 | 4/2012 | Castro et al. | |
| 2012/0190659 A1 | 7/2012 | Corey et al. | |
| 2014/0038958 A1 | 2/2014 | Ronnison et al. | |
| 2014/0155376 A1 | 6/2014 | Hendricks et al. | |
| 2016/0016971 A1 | 1/2016 | Valente | |
| 2017/0029435 A1 | 2/2017 | Shair et al. | |
| 2017/0320886 A1 | 11/2017 | Flyer et al. | |

FOREIGN PATENT DOCUMENTS

| EP | 0562849 A2 | 9/1993 |
|---|---|---|
| WO | WO 1997/043417 A1 | 11/1997 |
| WO | WO 1998/029438 A2 | 7/1998 |
| WO | WO 2000/041545 A2 | 7/2000 |
| WO | WO 2000/066611 A1 | 11/2000 |
| WO | WO 2001/023405 A2 | 4/2001 |
| WO | WO 2001/027135 A2 | 4/2001 |

(Continued)

OTHER PUBLICATIONS

Wittaker, Steven. Pharmacology & Therapeutics 173 (2017) 83-105.*
MedicineNet.com. (2004) Web: <http://www.medterms.com>.*
Myeloproliferative disorders: University of Maryland Medical Center. (2016).Web: <http://umm.edu/health/medical/altmed/condition/myeloproliferative-disorders>.*
Abushanab et al., 9(10 leads to 19)abeo steriods. Total synthesis of abeo-estradiol, abeo-estradiol 3-methyl ether, and 17 alpha-ethynyl abeo-estradiol-3-methyl ether. JOC Apr. 30, 1976;41(9):1601-3.
Aguayo et al. Angiogenesis in acute and chronic leukemias and myelodysplastic syndromes. Blood. Sep. 15, 2000;96(6):2240-5.
Aoki et al., Cortistatins A, B, C, and D, anti-angiogenic steroidal alkaloids, from the marine sponge Corticum simplex. JACS Mar. 15, 2006;128(10):3148-9.
Aoki et al., Cortistatins J, K, L, novel abeo-0(10-19)-androstane-type steroidal alkaloids with isoquinoline unit, from marine sponge Carticium simplex. Tetrahedron Lett. 2007;48(26)4485-88.

(Continued)

*Primary Examiner* — Deepak R Rao
*Assistant Examiner* — Laura M Daniel
(74) *Attorney, Agent, or Firm* — Knowles Intellectual Property Strategies, LLC

(57) ABSTRACT

Compounds of Formula (A'), (B'), (C'), (D'), (E'), (A"), (B"), (C"), (D"), (E"), (G1), and (G2) are useful as therapeutics for treating a wide variety of conditions in a host such as a human, e.g., including but not limited to, conditions associated with angiogenesis and/or which are mediated by CDK8 and/or CDK19 kinase activity. Also provided are methods of modulating the β-catenin pathway, methods of modulating STAT1 activity, methods of modulating the TGFβ/BMP pathway, methods of modulating HIF-1-alpha activity in a cell, and methods of increasing BIM expression to induce apoptosis, using an effective amount of a compound of Formula (A'), (B'), (C'), (D'), (E'), (A"), (B"), (C"), (D"), (E"), (G1), or (G2).

17 Claims, No Drawings

(56) References Cited

FOREIGN PATENT DOCUMENTS

| WO | WO 2001/030802 A2 | 5/2001 |
|---|---|---|
| WO | WO 2003/004518 A2 | 1/2003 |
| WO | WO 3063791 A2 | 8/2003 |
| WO | WO 2006/093993 A1 | 9/2006 |
| WO | WO 2007/082980 A1 | 7/2007 |
| WO | WO 2007/103162 A2 | 9/2007 |
| WO | WO 2008/064425 A1 | 6/2008 |
| WO | WO 2010/024930 A2 | 4/2010 |
| WO | WO 2010/123545 A2 | 10/2010 |
| WO | WO 2012/096934 A2 | 7/2012 |
| WO | WO 2013/122609 A1 | 8/2013 |
| WO | WO 2014/123900 A1 | 8/2014 |
| WO | WO 2014/134169 A1 | 9/2014 |
| WO | WO 2014/199377 A1 | 12/2014 |
| WO | WO 2015/040089 A1 | 3/2015 |
| WO | WO 2015/100420 A1 | 7/2015 |

OTHER PUBLICATIONS

Aoki et al., Structure-activity relationship and biological property of cortistatins, anti-angiogenic spongean steoidal alkaloids. Bioorg. Med. Chem. Nov. 1, 2007;15(21):6758-62. Epub Aug. 21, 2007.
*Arefolov v. Presidents and Fellows of Harvard College and Matthew Shair*, Case No. 1:17-cv-10785 (D. Mass.)filed May 4, 2017.
Atta et al., New Steroidal Alkaloids from the Roots of Buxus sempervirens. J. Nat. Prod. 1999; 62(5):665-69.
Berge et al., Pharmaceutical salts. J. Pharm. Sci. Jan. 1977;66(1):1-19.
Boeckman et al., The Dess-Martin Periodinane: 1,1,1-Triacetoxy-1,1-Dihydro-1,2-Benziodoxol-3(1H)-One. J. Org. Synth. 2000 77:141-52.
Brown et al., 1986, Caplus an 1986:627117.
Brown, The Pomeranz-Fritsch Reaction, Isoquinoline vs Oxazoles. J. Org. Chem. 1977;42:3208-09.
Cassoni et al., Ghrelin and cortistatin in lung cancer: expression of peptides and related receptors in human primary tumors and in vitro effect on the H345 small cell carcinoma cell line. J. Endocrinol. Invest. Oct. 2006; 29(9):781-90—Abstract.
Chen et al., Eryhtropoietin deficiency decreases vascular stability in mice. J. Clin. Invest. Feb. 2008.p118(2):526-33.
Cheson et al., National Cancer Institute-sponsored Working Group guidelines for chronic lymphocytic leukemia:revised guidelines for diagnosis and treatment. BLOOD. Jun. 15, 1996;87(12):4990-7.
Czako et al. "Discovery of Potent and Practical Antiangiogenic Agents Inspired by Cortistatin A", J. Am. Chem. Soc. vol. 131, No. 25, Apr. 1, 2009.
De Marino et al.,A new steroidal alkaloid from a marine sponge *Corticium* sp. Tetrahedron Lett. 1998;39(41):7611-14.
Du Bois et al. Nitrogen Transfer from Nitrodomanganese (v) Complex: Amination of Silyl Enol Ethers. JACS 1996;118(4)915-16.
Duboudin et al., Evidence for [2+2] and [4+2] cycloadditions of allylic Grignard-reagents to benzyne. J. Chem. Soc-Chem Commun. 1977;13:454-55.
Evans et al., New silicon-phosphorous reagents in organic synthesis-carbonyl and conjugate addition-reactions of silicon phosphate esters and related systems. JACS 1978;100(11):3467-77.
Extended European Search Report for EP 09810384.9, dated Mar. 30, 2012.
Ferrara, Vascular endothelial growth factor as a target for anticancer therapy. Oncologist. 2004;9 Suppl 1:2-10.
Folkman, Angiogenesis: an organizing principle for drug discovery? Nat. Rev. Drug Discov. Apr. 2007;6(4):273-86.
Folkman, Antiangiogenesis in cancer therapy—endostatin and its mechanisms of action. Exp. Cell Res. Mar. 10, 2006;312(5):594-607. Epub Dec. 22, 2005.
Folkman, Tumor angiogenesis: therapeutic implications. N. Engl. J. Med. Nov. 18, 1971;285(21):1182-6.

Furrow et al., Practical procedures for the preperation of N-tert-butyldimethylsilylhydrazones and their use in modified Wolff-Kishner reductions and in the synthesis of vinyl halides and gem-dihalides. JACS May 5, 2004;126(17):5436.
Gerber et al., The role of VEGF in normal and neoplastic hematopoiesis. J. Mol. Med. Jan. 2003;81(1):20-31. Epub Dec. 14, 2002.
Grant et al., Matrigel induces thymosin beta 4 gene in differentiating endothelial cells. J. Cell Sci. Dec. 1995;108(Pt 12):3685-94.
Hajos et al., Synthesis and Conversion of 2-Methyl-2-(3Ooxobuty1)-1,3-cyclopentanedione to the Isomeric Racemic Ketols of the [3.2.1]Bicyclooctane and of the Perhydroindan Series. J. Org. Chem. 1974;39:1612-15.
Hajos et al., Total Synthesis of (+−)-17B-Hydroxy-d9(10)-des-A-Androsten-5-one-[(+−)-2,3,4a,4,5,7,8,9,9aB,9ba-Decahydro-3B-hydroxy-3aB,6-dimethyl-1H-benz[e]inden=7-one]. J. Org. Chem. 1967;32:3008-10.
Hanahan et al., Patterns and emerging mechanisms of the angiogenic switch during tumorigenesis. Cell. Aug. 9, 1996;86(3):353-64.
Huang et al., Control of cyclin D1, p27(Kipl), and cell cycle progression in human capillary endothelial cells by cell shape and cytoskeletal tension. Mol. Biol. Cell. Nov. 1998 9(11):3179-93.
Hurwitz et al., Bevacizumab plus irinotecan, fluorouracil, and leucoviorin for metastatic colorectal cancer. N. Engl. J. Med. Jun. 3, 2004;350(23):2335-42.
Hussong et al., Evidence of increased angiogenesis in patients with acute myeloid leukemia. Blood. Jan. 1, 2000;95(1):309-13.
International Preliminary Report on Patentability for PCT/US2009/04911, dated Nov. 3, 2011.
International Search Report and Written Opinion for PCT/IS2016/40482, dated Sep. 26, 2016.
International Search Report and Written Opinion for PCT/US16/68125 dated Mar. 16, 2017.
International Search Report and Written Opinion for PCT/US16/68137 dated Mar. 16, 2017.
International Search Report and Written Opinion for PCT/US16/68143 dated Mar. 23, 2017.
International Search Report and Written Opinion for PCT/US2009/04911, dated May 4, 2010.
International Search Report and Written Opinion for PCT/US2014/072365 dated May 19, 2015.
International Search Report and Written Opinion for PCT/US2016/31188, dated Aug. 18, 2016.
International Search Report and Written Opinion for PCT/US2016/31279, dated Aug. 25, 2016.
Isaacs et al., Synthesis of an Enantiomerically Pure Intermediate Containing the CD Substructure of Taxol. J. Org. Chem. 1993;58:3938-41.
Jain, Normalizing tumor vaculature with anti-angiogenic therapy:a new paradigm for combination therapy. Nat. Med. Sep. 2001;7(9):987-9.
Kerbel et al., Clinical translation of angiogenesis inhibitors. Nat. Rev. Cancer. Oct. 2002;2(10):727-39.
Khurana et al., Angiogenesis-dependent and independent phases of intimal hyperplasia. Circulation. Oct. 19, 2004;110(16):2436-43. Epub Oct. 11, 2004.
Klagsbrun et al., Molecular angiogenesis. Chem. Biol. Aug. 1999;6(8):R127-24.
Kohen et al., Solvolysis of 19-substituted androstane derivatives. J. Org. Chem. Jul. 1970;35(7):2272-5.
Kolb et al., Catalytic Asymmetric Dihydroxylation. J. Chem. Rev. 1994;94:2483-547.
Kolonin et al., Reversal of obesity by targeted ablation of adipose tissue. Nat. Med. Jun. 2004;10(6);625-32. Epub May 9, 2004.
Kotoku et al., "Synthetic Stufies of Cortistatin A Analogue from the CD-Ring Fragment of Vitamin D2", Chem. Pharm. Bull. 61(1) 1024-1029, May 13, 2013.
Kozikowiski et al., Phosphoniosilyation—an efficient and practical method for the beta-functionalization of enones. J. Org. Chem. 1986;51(17):3400-02.
Kunding, Low temperature Grignard reactions with pure Mg slurries. Trapping of cyclopropylmethyl and benzocyclobutenylmethyl Grignard reagents with $CO_2$. Helvetica Chimica Acta. 1981;64(8):2606-13.

(56) References Cited

OTHER PUBLICATIONS

Kupchan et al., Buxus alkaloids. 13. A synthetic approach to the 9(10—19) abeo-pregnane system. JACS. Nov. 22, 1967;89(24):6327-32.
Lee et al., Entantioselective synthesis of (+)-cortistatin A, a potent and selective inhibitor of endothelial cell proliferation. JACS Dec. 17, 2008;130(50):16864-6.
Liu et al., 5-(Trimethylstannyl)-2H-pyran-2-one and 3-(Trimethylstannyl)-2H-pyran-2-one: New 2H-Pyran-2-one Synthons. JOC Sep. 20, 1996;61(19):6693-6699.
Magnus et al., Oxidative addition of azide anion to triisopropylsilyl enol ethers: Synthesis of [alpha]-azido ketones and 2-amino(methoxycarbonyl)alk-2-en-1-ones. Tetrahedron 1995;51(41):11075-86.
Mammoto et al., A mechanosensitivie transcriptional mechanism that controls angiogenesis. Nature. Feb. 26, 2009;457(7233)1103-8.
Mayer, Two steps forward in the treatment of colorectal cancer. N. Engl. J. Med. Jun. 3, 2004;350(23):2406-8.
Molica et al., Prognostic value of enhanced bone marrow angiogenesis in early B-cell chronic lymphocytic leukemia. Blood. Nov. 1, 2002;100(9):3344-51.
Moses, The regulation of neovascularization of matrix metalloproteinases and their inhibitors. Stem Cells. 1997;15(3):180-9.
Moulton et al., Angiogenesis inhibitors endostatin or TNP-470 reduce intimal neovascularization and plaque growth in apolipoprotein E-deficient mice. Circulation. Apr. 6, 1999;99(13):1726-32.
Mousseau et al., An analog of the natural steroidal alkaloid Cortistatin A potently suppresses Tat dependent HIV transcription', Cell Host Microbe. Jul. 19, 2012; 12 (1): 97-108. doi:10.1016/j.chom.2012.05.016.
Neef et al., A radical approach to the synthesis of 9(10-19)abeosteroids. Tetrahedron. 1993;49(4):833-40.
Neef et al., New steroids by Simmons-Smith methylenation and subsequent rearrangement. J. Org. Chem. 1987;52(18):4143-46.
Nicolaou et al., Total synthesis of (+)-cortistatin A. (Supportive Information) Angew. Chem. Int. Ed. Engl. 2008;47(38):1-57.
Ohtani et al., Blockade of vascular endothelial growth factor suppresses experimental restenosis after intraluminal injury by inhibiting recruitment of monocye lineage cells. Circulation. Oct. 19, 2004;110(16):2444-52. Epub Oct. 11, 2004.
Ottow et al., Highly diastereoselective synthesis of 11 beta, 17 beta-diaryl-18a-homo-19-nor steroids. Journal Fur Praktishche Chemie-Chemiker-Zeitung. 1997;339(4):365-70.
Peacock et al., Angiogenesis inhibition suppresses collagen arthritis. J. Exp. Med. Apr. 1, 1992;175(4):1135-8.
Pelish et al. Mediator Kinase Inhibition Further Activates Super-Enhancer Associated Genes in AML. Nature. Oct. 8, 2015; 526(7572): 273-276.
Perez-Atayde et al., Spectrum of tumor angiogenesis in the bone marrow of children with acute lymphoblastic leukemia. Am. J. Pathol. Mar. 1997;150(3):815-21.
Puckett et al., The structure of buxenine-G. Tetrahedron Lett. 1966;7(32):3815-18.
Rastinejad et al., Regulation of the activity of a new inhibitor of angiogenesis by a cancer suppressor gene. Cell. Feb. 10, 1989;56(3):345-55.
Rigby et al., A general approach to the synthesis of C8-Oxygenated Guaianolides. JOC. 1987;52:34-44.
Shenvi et al., Synthesis of (+)-cortistatin A (Supporting Information). JACS Jun. 11, 2008; 130(23):SI-1-SI-22. Epub May 14, 2008.
Shenvi et al., Synthesis of (+)-cortistatin A JACS Jun. 11, 2008; 130(23):7241-3. Epub May 14, 2008.
Shih et al., Selective stimulation of VEGFR-1 prevents oxygen-induced retinal vascular degeneration in retinopathy of prematurity. J. Clin. Invest. Jul. 2003;112(1):50-7.
Shimizu et al., ABL2/ARG tyrosine kinase mediates SEMA3F-induced RhoA inactivation and cytoskeleton collapse in human glioma cells. J. Biol. Chem. Oct. 3, 2008;283(40):27230-8. Epub Jul. 25, 2008.
Shojima et al., The role of vascular endothelial growth factor in restenosis: the controversy continues. Circulation. Oct. 19, 2004;110(16):2283-6.
Smith et al., Organometallic reagents in synthesis: A new protocol for construction of the indole nucleus. Tetrahedron. 1986;42:2957.
Still et al., Rapid Chromatographic Technique for Perparative Seperations with Moderate Resolution. J. Org. Chem. 1978;43:2923-25.
Street et al., Vascular endothelial growth factor stimulates bone repair by promoting angiogenesis and bone turnover. Proc. Natl. Acad. Sci. USA. Jul. 23, 2002;99(15):9656-61. Epub Jul. 12, 2002.
Tamao et al., (Diisopropoxymethylsilyl)methyl Grignard Reagent: A New, Practically Useful Nucleophilic Hydroxymethylating Agent. J. Org. Chem. 1983;48:2120-22.
Teicher et al., Antiangiogenic agents can increase tumor oxygenation and response to radiation therapy. Radiat. Oncol. Investig. 1994;2(6):269-276.
Vacca et al., Bone marrow angiogenesis and progression in multiple myeloma. Br. J. Haematol. Jul. 1994;87(3):503-8.
Wang et al., Marine-Derived Angiogenesis Inhibitors for Cancer Therapy. Mar. 15, 2013; 11(3): 903-933.
Watanabe et al., Cortistatins E, F, G, and H, four novel steroidal alkaloids from marine sponge Corticium simplex. Tetrahedron. 2007;63(19):4074-79.
Williams et al., Isocyanide addition to pyridinium salts. Efficient entry into substituted nicotinonitrile derivatives. Org. Lett. Dec. 7, 2006;8(25):5789-92.
Yamashita et al., A concise synthesis of the pentacyclic framework of Cortistatins. Org. Lett., Jul. 17, 2008; 10(16): 3413-3415.

* cited by examiner

CORTISTATIN ANALOGUES AND SYNTHESES AND USES THEREOF

STATEMENT OF RELATED APPLICATIONS

This application is a continuation of PCT/US2016/040482, filed Jun. 30, 2016, which claims priority benefit of U.S. provisional patent application 62/187,696, filed Jul. 1, 2015. The entirety of this provisional application is hereby incorporated by reference for all purposes.

BACKGROUND

The cortistatins are a group of anti-angiogenic steroidal alkaloids first isolated in 2006 from the marine sponge *Corticium simplex*. See, e.g., Aoki, et al., *JACS* (2006) 128: 3148-9. From the date of isolation to the present, these natural products have been the subject of much study, especially in the development of total syntheses and of new unnatural biologically active analogs. See, e.g., Aoki et al., *Bioorganic & Medicinal Chemistry* (2007) 15: 6758-62. Mousseau et al., *Cell Host & Microbe* (2012) 12: 97-108; Chen et al., *Organic & Biomolecular Chemistry* (2010) 8: 2900; Hardin et al., *European Journal of Organic Chemistry* (2010) 19: 3553. Thus, there is an active interest in the development of new cortistatin analogs and methods of their preparation.

U.S. Pat. No. 9,127,019 titled "Cortistatin Analogs and Synthesis Thereof" filed by Flyer, et. al., and assigned to the President and Fellows of Harvard College describes analogs of Cortistatins A, J, K, and L having the general Formula I and salts thereof, and the synthesis thereof, wherein $R_1$, $R_2$, $R_3$, $R_4$, n, and m are as described therein.

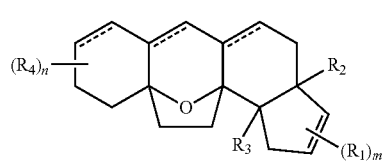

(I)

The '019 patent discloses that such compounds are anti-angiogenic and can be used to treat proliferative diseases.

WO 2015/100420 titled "Cortistatin Analogs and Syntheses and Uses Thereof" filed by Shair, et al., and also assigned to the President and Fellows of Harvard College describes further analogs of Cortistatin and methods and compositions that include the described cortistatin analogs to treat proliferative disorders such as cancer, and in particular, a hematopoietic cancer such as leukemia, multiple myeloma (MM), acute myelocytic leukemia (AML), a myeloproliferative neoplasm, acute lymphoblastic leukemia (ALL), chronic myeolcytic leukemia (CML) and primary myelofibrosis (PMF). More generally, the '420 application describes a method to treat a condition associated with CDK8 and/or CDK19 kinase activity, that includes administering an effective amount of a disclosed compound or its pharmaceutically acceptable salt, quaternary amine, or N-oxide. CDK8 and its regulatory subunit cyclin C are components of the RNA polymerase II haloenyme complex, which phosphorylates the carboxy-terminal of the largest subunit of RNA polymerase II. CDK8 regulates transcription by targeting the CDK7/cyclin H subunits of the general transcription factor TFIIH.

Other synthetic and biological descriptions of Cortistatin A and analogs of Cortistatin A have been described in: Chiu et al., *Chemistry* (2015), 21: 14287-14291, titled "Formal Total Synthesis of (+)-Cortistatins A and J"; Valente et al., *Current HIV Research* (2015), 13: 64-79, titled "Didehydro-Cortistatin A Inhibits HIV-1 Tat Mediated Neuroinflammation and Prevents Potentiation of Cocaine Reward in Tat Transgenic Mice"; Motomasa et al., *Chemical & Pharma. Bulletin* (2013), 61: 1024-1029 titled "Synthetic Studies of Cortistatin A Analog from the CD-ring Fragment of Vitamin D2"; Valente et al., *Cell Host & Microbe* (2012), 12: 97-108 titled "An Analog of the Natural Steroidal Alkaloid Cortistatin A Potently Suppress Tat-dependent HIV Transcription"; Motomasa et al., *ACS Med. Chem. Lett.* (2012), 3: 673-677 titled "Creation of Readily Accessible and Orally Active Analog of Cortistatin A"; Danishefsky et al., *Tetrahedron* (2011) 67: 10249-10260 titled "Synthetic Studies Toward (+)-Cortistatin A"; Motomasa et al., *Heterocycles* (2011), 83: 1535-1552, titled "Synthetic Study of Carbocyclic Core of Cortistatin A, an Anti-angiogenic Steroidal Alkaloid from Marine Sponge"; Motomasa et al., *Org. Lett.* (2011), 13: 3514-3517, titled "Stereoselective Synthesis of Core Structure of Cortistatin A"; Baran et al., *JACS* (2011), 133: 8014-8027, titled "Scalable Synthesis of Cortistatin A and Related Structures"; Hirama et al., *JOC* (2011), 76: 2408-2425, titled "Total Synthesis of Cortistatins A and J"; Zhai et al., *Org. Lett.* (2010), 22: 5135-5137, titled "Concise Synthesis of the Oxapentacyclic Core of Cortistatin A"; Stoltz et al., *Org. Biomol. Chem.* (2010), 13: 2915-2917, titled "Efforts Toward Rapid Construction of the Cortistatin A Carbocyclic Core via Enyne-ene Metathesis"; Sarpong et al., *Tetrahedron* (2010), 66: 4696-4700, titled "Formal Total Synthesis of (+)-Cortistatin A"; Nicolaou et al., *Angewandte Chemie* (2009), 48: 8952-8957, titled "Cortistatin A is a High-Affinity Ligand of Protein Kinases ROCK, CDK8, and CDK11".

U.S. Patent Application Publication US2013/0217014 and PCT Application WO2013/122609 titled "Methods of Using CDK8 Antagonists" filed by Firestein, et al., and assigned to Genentech, describes the use of CDK8 antagonists against various cancers.

Despite the progress to date, it would be advantageous to provide new compounds that can be used to treat such disorders in a host, including a human.

SUMMARY OF THE INVENTION

The invention provides novel cortistatin analogs of Formula (A'), (B'), (D'), (E'), (A"), (B"), (D"), (E"), (G1), and (G2) and pharmaceutically acceptable salts, quaternary amine salts, and N-oxides thereof. The invention also provides novel intermediates of Formula (C') and (C"), which can also be used as pharmaceutically active compounds. In one embodiment, the compounds can be used to treat a disorder mediated by CDK8 or CDK19 activity, by inhibiting one or both of these enzymes.

These analogs may be synthesized, for example, by reductive amination of a ketone of Formula (B') or (B"), wherein $R^5$ is —$OR^A$, —$OC(=O)R^A$, —$OC(=O)OR^A$, —$OC(=O)N(R^A)_2$, —$OS(=O)_2R^A$, —$N_3$, —$N(R^A)_2$, —$NR^AC(=O)R^A$, —$NR^AC(=O)OR^A$, —$NR^AC(=O)N(R^A)_2$, —$NR^AS(=O)_2R^A$, or —$C(R^A)_3$, to provide the aminated product of Formula (A') or (A"), as depicted in Schemes 1 and 2, optionally via an imine intermediate of Formula (C') or (C").

Scheme 1.
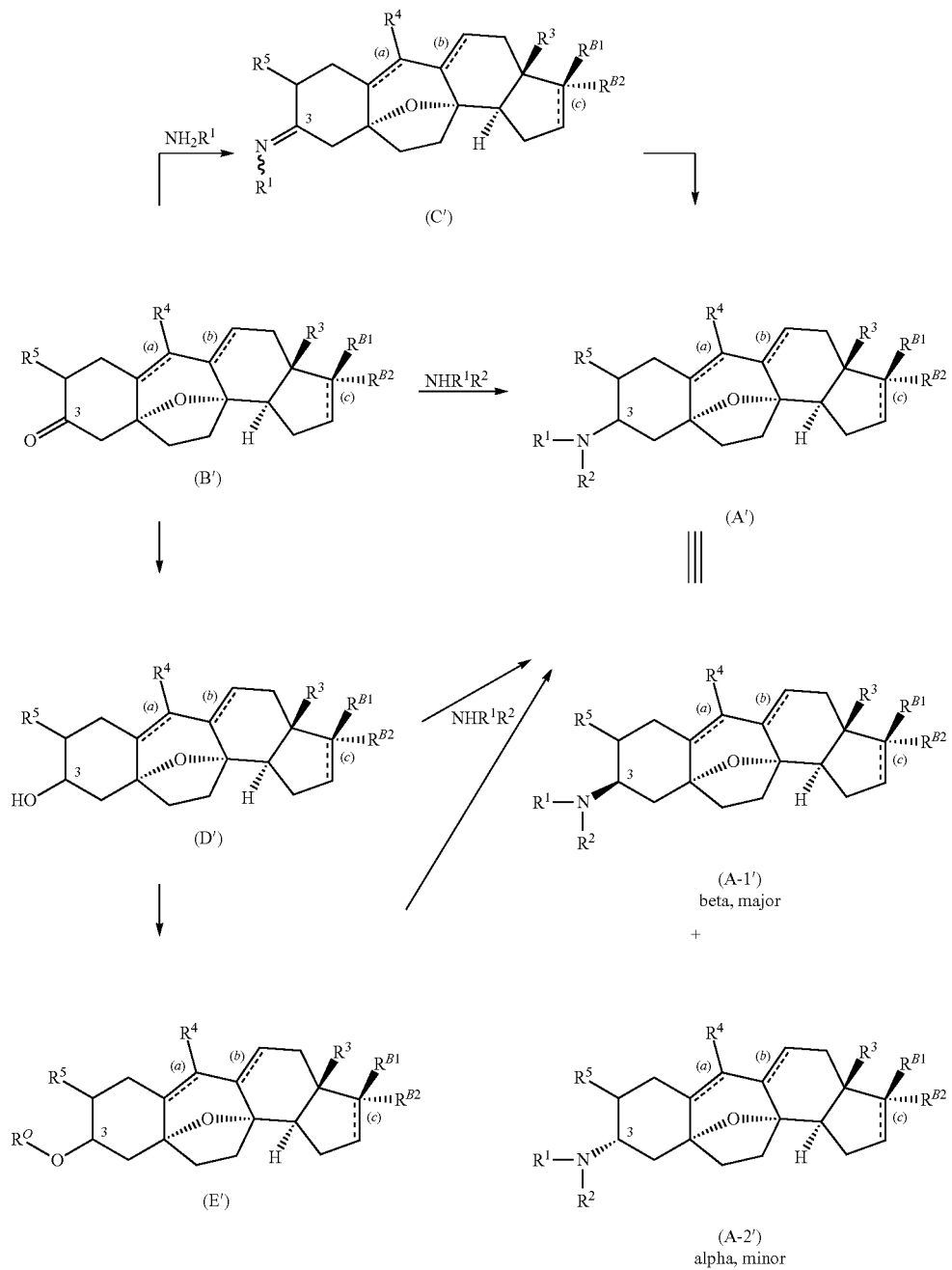
Scheme 2.
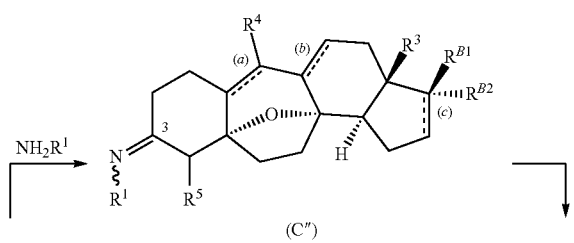

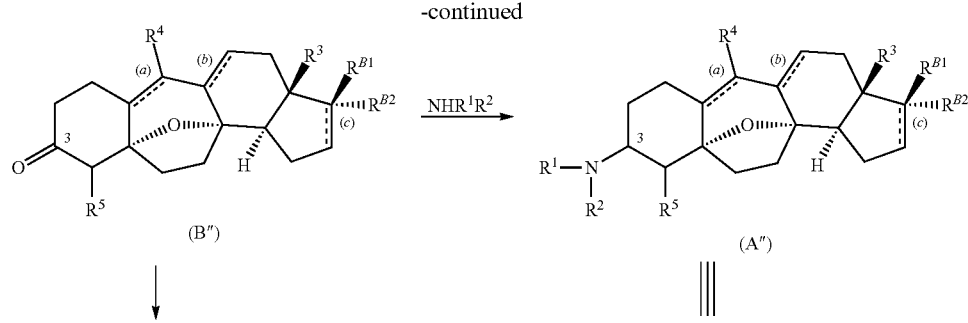

(B″)    →NHR¹R²→    (A″)

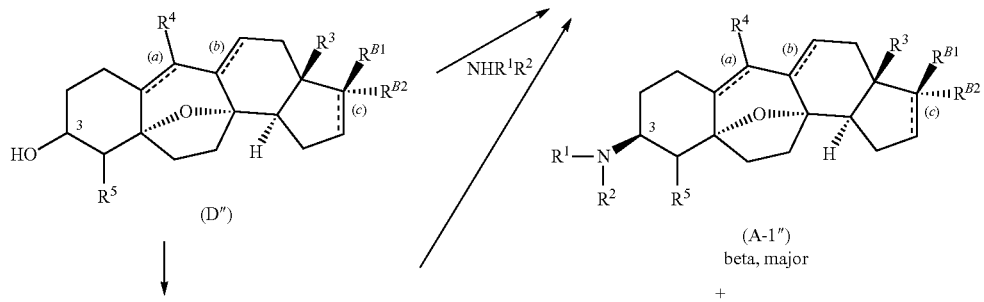

(D″)    →NHR¹R²→    (A-1″) beta, major

+

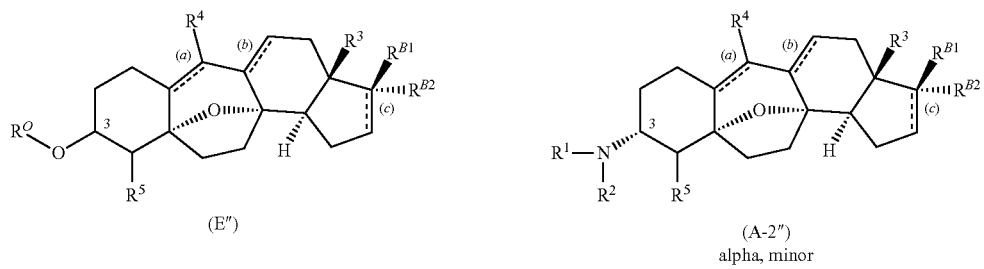

(E″)    (A-2″) alpha, minor

Further provided are novel cortistatin analogs of Formula (D') or (D″). Such compounds may be prepared by reduction of the ketone of Formula (B') or (B″) to provide a C3-hydroxyl compound of Formula (D') or (D″).

Still yet further provided is a compound of Formula (E') or (E″). Such compounds may be prepared by substitution of the compound of Formula (D') or (D″). Such compounds may also be converted to a compound of Formula (A') or (A″) upon treatment with an amine under suitable conditions.

Compounds of Formula (B') or (B″), wherein $R^5$ is as defined herein, may be formed via trapping of the Compound of Formula (B0) as the enolate (e.g., via treatment with base and a $P_1$-LG group, wherein $P_1$ is silyl and LG is a leaving group), followed by subsequent oxidation or amination of the double bond, or reaction of the double bond with an electrophilic carbon $C(R^4)_3$-LG, wherein LG is a leaving group, to provide a substituted ketone product, wherein $R^5$ is —$OR^A$, —$OC(=O)R^A$, —$OC(=O)OR^A$, —$OC(=O)N(R^A)_2$, —$OS(=O)_2R^A$, —$N_3$, —$N(R^A)_2$, —$NR^AC(=O)R^A$, —$NR^AC(=O)OR^A$, —$NR^AC(=O)N(R^A)_2$, —$NR^AS(=O)_2R^A$, or —$C(R^A)_3$. See, e.g., Scheme 3.

Scheme 3.

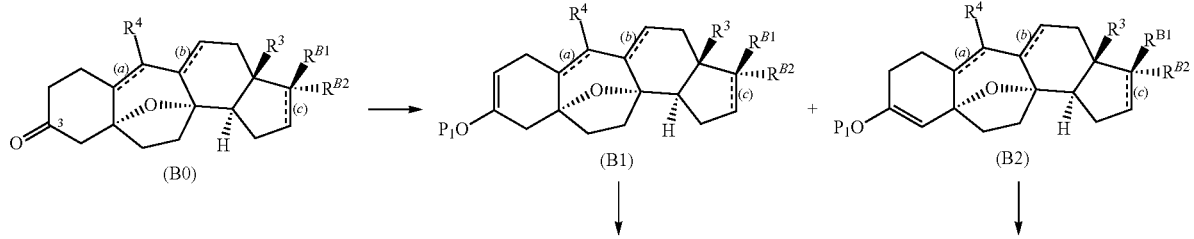

(B0)    (B1)    (B2)

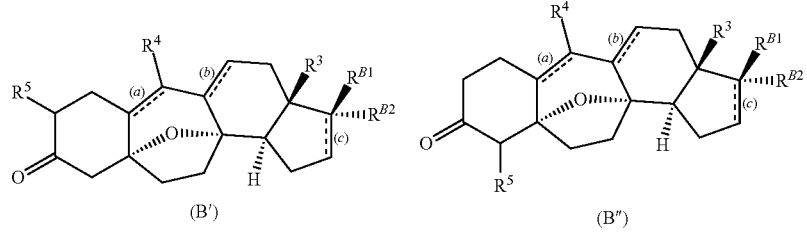

(B')    (B")

Still further provided are compounds of Formula (G1) and (G2), prepared from a Wolf-Kishner reduction of compounds of Formula (B') or (B"). See, e.g., Scheme 4.

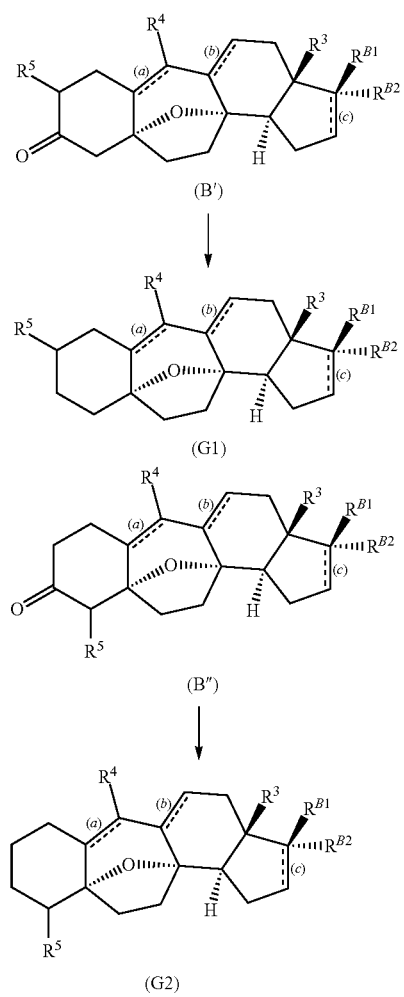

Further provided are pharmaceutical compositions comprising a cortistatin analogs of Formula (A'), (B'), (C'), (D'), (E'), (A"), (B"), (C"), (D"), (E"), (G1), or (G2) or a pharmaceutically acceptable salt, quaternary amine salt, or N-oxide thereof, and a pharmaceutically acceptable excipient. Further provided are methods of use and treatment.

Thus, as further described herein, in one aspect, provided is a method of preparing a compound of Formula (A') or (A"), or a pharmaceutically acceptable salt, quaternary amine salt, or N-oxide thereof; the method comprising contacting a compound of Formula (B') or (B"), or a pharmaceutically acceptable salt, provided $R^{B1}$ and $R^{B2}$ are not joined to form an oxo group; with an amine of formula $HNR^1R^2$, or salt thereof, under reductive amination conditions.

In another aspect, provided is a method of preparing a compound of Formula (D') or (D"), or a pharmaceutically acceptable salt thereof; the method comprising contacting a compound of Formula (B') or (B"), or a pharmaceutically acceptable salt, with a reducing agent, to provide a compound of Formula (D') or (D").

In another aspect, provided is a method of preparing a compound of Formula (E') or (E"), or a pharmaceutically acceptable salt thereof; the method comprising contacting a compound of Formula (D') or (D"), or a pharmaceutically acceptable salt thereof, with a compound of formula $R^O$-LG, wherein LG is a leaving group, to provide a compound of Formula (E') or (E").

In another aspect, provided is a method of preparing a compound of Formula (A') or (A"), or a pharmaceutically acceptable salt, quaternary amine salt, or N-oxide thereof; the method comprising contacting a compound of Formula (E') or (E"), wherein $R^O$ is C(=O)$R^A$, or a pharmaceutically acceptable salt thereof, with a compound of formula $NHR^1R^2$, to provide a compound of Formula (A') or (A").

In another aspect, provided are pharmaceutical compositions comprising a compound of Formula (A'), (B'), (C'), (D'), (E'), (A"), (B"), (C"), (D"), (E"), (G1), or (G2), or a pharmaceutically acceptable salt, quaternary amine, or N-oxide thereof.

In another aspect, provided is a method of treating a condition associated with angiogenesis comprising administering to a subject in need thereof a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof. In certain embodiments, the condition is a diabetic condition, an inflammatory condition, macular degeneration, obesity, atherosclerosis, or a proliferative disorder.

In yet another aspect, provided is a method of treating a condition associated with, i.e., mediated by, CDK8 and/or CDK19 kinase activity, comprising administering to a subject in need thereof a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof. In certain embodiments, the condition is a proliferative disorder. In certain embodiments, the proliferative disorder is cancer. In certain embodiments, the cancer is a hematopoietic cancer. In certain embodiments, the hematopoietic cancer is lymphoma. In certain embodiments, the hematopoietic cancer is leukemia. In certain embodiments, the hematopoietic cancer is multiple myeloma. In certain embodiments, the leukemia is acute myelocytic leukemia (AML). In certain embodiments, the proliferative disorder is a myeloproliferative neoplasm. In certain embodiments, the myeloproliferative neoplasm is primary myelofibrosis (PMF). In certain embodiments, the cancer is a solid tumor.

In yet another aspect, provided is a method of inhibiting CDK8 and/or CDK19 kinase activity in a cell comprising contacting a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof, with the cell.

In yet another aspect, provided is a method of modulating the β-catenin pathway in a cell comprising contacting a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof, with the cell.

In yet another aspect, provided is a method of modulating STAT1 activity in a cell comprising contacting a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof, with the cell.

In yet another aspect, provided is a method of modulating the TGFβ/BMP pathway in a cell comprising contacting a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof, with the cell.

In yet another aspect, provided is a method of modulating HIF-1-A (HIF-1-alpha) activity in a cell comprising contacting a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof, with the cell.

In yet another aspect, provided is a method of increasing BIM expression to induce apoptosis in a cell comprising contacting a compound of Formula (A'), (B'), (C'), (D'), (E'), (A"), (B"), (C"), (D"), (E"), (G1), or (G2), or a pharmaceutically acceptable salt, quaternary amine, or N-oxide thereof, or a pharmaceutical composition thereof, with the cell.

In any of the above recited methods as described herein, the method may be carried out in vitro or in vivo.

The details, objects, and advantages of the invention will be apparent from the Detailed Description, the Examples, and from the claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. Also contemplated are stereoisomers featuring either a Z or E configuration, or mixture thereof, about a double bond. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures. The mixture may contain two enantiomers, two diastereomers, or a mixture of diastereomers and enantiomers.

If, for instance, a particular enantiomer of a compound described herein is desired, it may be prepared by asymmetric synthesis, or by derivation with a chiral auxiliary, where the resulting diastereomeric mixture is separated and the auxiliary group cleaved to provide the pure desired enantiomers. In some embodiments, a compound described herein is prepared by asymmetric synthesis with an enzyme. Enantiomers and diastereomers may be separated by means of fractional crystallization or chromatography (e.g., HPLC with a chiral column). Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In some embodiments, the carbon to which $R^{B1}$ or $R^{B2}$ is attached is in the (S) configuration. In some embodiments, the carbon to which $R^{B1}$ or $R^{B2}$ is attached is in the (R) configuration. In some embodiments, the carbon to which $R^{B1}$ or $R^{B2}$ is attached is in the same configuration as a naturally occurring cortistatin (e.g., cortistatin A, cortistatin B). In some embodiments, the carbon to which $R^{B1}$ or $R^{B2}$ is attached is in the opposite configuration as a naturally occurring cortistatin (e.g., cortistatin A, cortistatin B). In some embodiments, the carbon to which $Y^1$ or $Y^2$ is attached is in the (S) configuration. In some embodiments, the carbon to which $Y^1$ or $Y^2$ is attached is in the (R) configuration. In some embodiments, the carbon to which $Y^1$ or $Y^2$ is attached is in the same configuration as a naturally occurring cortistatin (e.g., cortistatin A, cortistatin B). In some embodiments, the carbon to which $Y^1$ or $Y^2$ is attached is in the opposite configuration as a naturally occurring cortistatin (e.g., cortistatin A, cortistatin B). In some embodiments, the carbon to which $R^3$ is attached is in the (S) configuration. In some embodiments, the carbon to which $R^3$ is attached is in the (R) configuration. In some embodiments, the carbon to which $R^3$ is attached is in the same configuration as a naturally occurring cortistatin (e.g., cortistatin A, cortistatin B). In some embodiments, the carbon to which $R^3$ is attached is in the opposite configuration as a naturally occurring cortistatin (e.g., cortistatin A, cortistatin B). In some embodiments, the carbon to which $R^5$ is attached is in the (S) configuration. In some embodiments, the carbon to which $R^5$ is attached is in the (R) configuration. In some embodiments, the carbon to which $R^5$ is attached is in the same configuration as a naturally occurring cortistatin (e.g., cortistatin A, cortistatin B). In some embodiments, the carbon to which $R^5$ is attached is in the opposite configuration as a naturally occurring cortistatin (e.g., cortistatin A, cortistatin B).

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 9 ring carbon atoms ("$C_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 9 ring carbon atoms ("C$_{3-9}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-10}$ cycloalkyl. In certain embodiments, the cycloalkyl group is a substituted C$_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetra-hydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —NR$^{bb}$P(=O)(OR$^{cc}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$—P(=O)(R$^{aa}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_2$-alkenyl, $C_{2-6}$ alkynyl, heteroC$_{1-6}$ alkyl, heteroC$_{2-6}$alkenyl, heteroC$_2$-alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, an exemplary substituent is selected from the group consisting of halogen, —CN, —NO$_2$, —N$_3$, —SO$_2$H, —SO$_3$H, —OH, —O$R^{aa}$, —N($R^{bb}$)$_2$, —SH, —S$R^{aa}$, —SS$R^{cc}$, —C(=O)$R^{aa}$, —CO$_2$H, —CHO, —CO$_2$$R^{aa}$, —OC(=O)$R^{aa}$, —OCO$_2$$R^{aa}$, —C(=O)N($R^{bb}$)$_2$, —OC(=O)N($R^{bb}$)$_2$, —NR$^{bb}$C(=O)$R^{aa}$, —NR$^{bb}$CO$_2$$R^{aa}$, —NR$^{bb}$C(=O)N($R^{bb}$)$_2$, —C(=O)NR$^{bb}$SO$_2$$R^{aa}$, —NR$^{bb}$SO$_2$$R^{aa}$, —SO$_2$N($R^{bb}$)$_2$, —SO$_2$$R^{aa}$, —S(=O)$R^{aa}$, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quaternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and —OSO$_2$$R^{aa}$, wherein $R^{aa}$ as defined herein. The group —OSO$_2$$R^{aa}$ encompasses leaving groups such as tosyl, mesyl, and besyl, wherein $R^{aa}$ is optionally substituted alkyl (e.g., —CH$_3$) or optionally substituted aryl (e.g., phenyl, tolyl).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O)S$R^{aa}$, —OC(=O)$R^{aa}$, —OCO$_2$$R^{aa}$, —OC(=O)N($R^{bb}$)$_2$, —OC(=NR$^{bb}$)$R^{aa}$, —OC(=NR$^{bb}$)O$R^{aa}$, —OC(=NR$^{bb}$)N($R^{bb}$)$_2$, —OS(=O)$R^{aa}$, —OSO$_2$$R^{aa}$, —OSi($R^{aa}$)$_3$, —OP($R^{cc}$)$_2$, —OP(=O)($R^{aa}$)$_2$, and —OP(=O)(O$R^{cc}$)$_2$, wherein $R^{aa}$, $R^{bb}$, and $R^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —S$R^{aa}$, —S=S$R^{cc}$, —SC(=S)S$R^{aa}$, —SC(=O)S$R^{aa}$, —SC(=O)O$R^{aa}$, and —SC(=O)$R^{aa}$, wherein $R^{aa}$ and $R^{cc}$ are as defined herein.

As used herein, the term, "amino" refers to the group —NH$_2$. The term "substituted amino," by extension, refers to a monosubstituted amino or a disubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2$$R^{aa}$, —NHC(=O)N($R^{bb}$)$_2$, —NHC(=NR$^{bb}$)N($R^{bb}$)$_2$, —NHSO$_2$$R^{aa}$, and —NHP(=O)(O$R^{cc}$)$_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2$$R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2$$R^{aa}$, and —N$R^{bb}$P(=O)(O$R^{cc}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "sulfonyl" refers to a group selected from —SO$_2$N($R^{bb}$)$_2$, —SO$_2$$R^{aa}$, and —SO$_2$O$R^{aa}$, wherein $R^{aa}$ and $R^{bb}$ are as defined herein.

As used herein, the term "sulfinyl" refers to the group —S(=O)$R^{aa}$, wherein $R^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2$$R^{aa}$, —C(=O)S$R^{aa}$, —C(=S)S$R^{aa}$), amides (—C(=O)N($R^{bb}$)$_2$, —C(=O)N$R^{bb}$SO$_2$$R^{aa}$, —C(=S)N($R^{bb}$)$_2$), and imines (—C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

As used herein, the term "silyl" refers to the group —Si($R^{aa}$)$_3$, wherein $R^{aa}$ is as defined herein.

As used herein, the term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=NR)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(O-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(=O)(R$^{aa}$)$_2$, and —P(=O)(OR$^{cc}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6- dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(=O)(R^{aa})_2$, and $-P(=O)(OR^{cc})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "modulating" refers to the ability of a compound to increase or inhibit a particular biological process (e.g., kinase activity, overexpression), e.g., for example in a cell (e.g., in vitro such as a cell in a cell culture, or in vivo such as a cell in a subject) relative to vehicle.

As used herein "inhibition", "inhibiting", "inhibit" and "inhibitor", and the like, refer to the ability of a compound to reduce, slow, halt or prevent activity of a particular biological process (e.g., kinase activity, overexpression), e.g., for example in a cell (e.g., in vitro such as a cell in a cell culture, or in vivo such as a cell in a subject) relative to vehicle.

As used herein "increasing" or "increase", and the like, refer to the ability of a compound to stimulate activity of a particular biological process (e.g., kinase activity), e.g., for example in a cell (e.g., in vitro such as a cell in a cell culture, or in vivo such as a cell in a subject) relative to vehicle.

DETAILED DESCRIPTION OF CERTAIN EMBODIMENTS OF THE INVENTION

As described herein, provided are novel cortistatin analogs of Formula (A'), (B'), (C'), (D'), (E'), (A"), (B"), (C"), (D"), (E"), (G1), and (G2). Such compounds may be synthesized, in part, by reductive amination of a ketone of Formula (B') or (B") to provide an aminated product of Formula (A') or (A"), optionally via an imine intermediate of Formula (C') or (C"). Further provided are new cortistatin analogs of Formula (D'), (D"), (E'), (E"), (G1) and (G2). See, e.g., Schemes 1-4, supra.

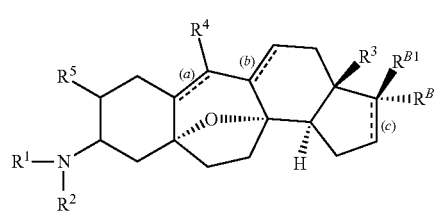
(A')

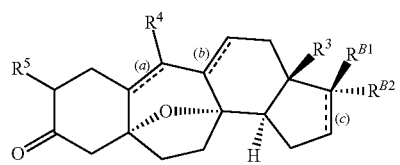
(B')

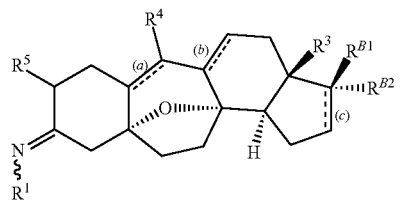
(C')

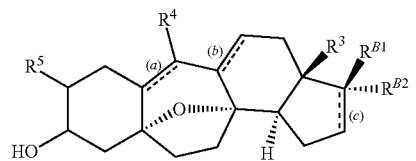
(D')

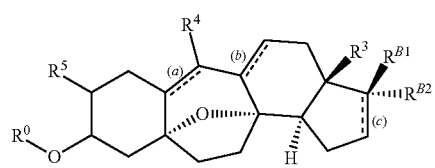
(E')

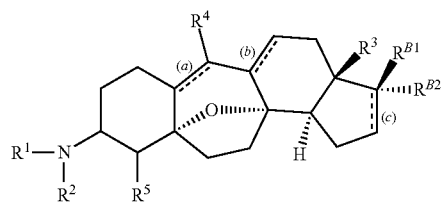
(A")

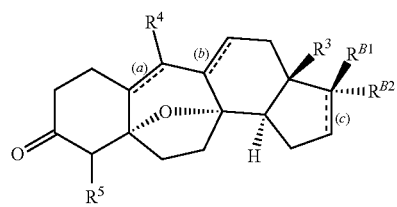
(B")

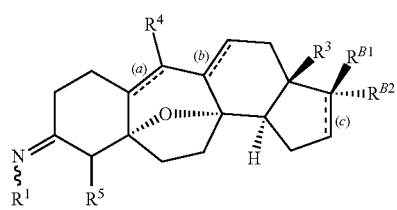
(C")

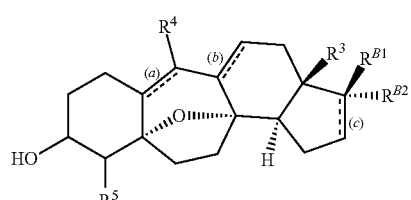
(D")

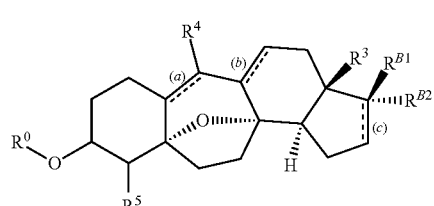
(E")

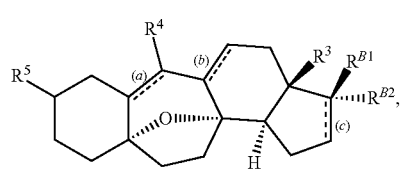
(G1)

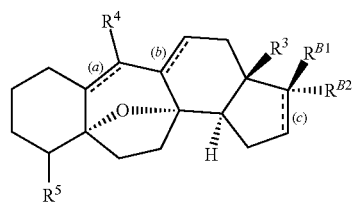
(G2)

and pharmaceutically acceptable salts, quaternary amine salts, or N-oxides thereof, wherein:

$R^1$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —SR$^A$, —N(R$^A$)$_2$, —C(=O)R$^A$, —C(=O)OR$^A$, —C(=O)N(R$^A$)$_2$, —S(=O)$_2$R$^A$, or a nitrogen protecting group;

R$^2$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^A$, —C(=O)OR$^A$, —C(=O)N(R$^A$)$_2$, —S(=O)$_2$R$^A$, or a nitrogen protecting group;

or R$^1$ and R$^2$ are joined to form an optionally substituted heterocyclyl or optionally substituted heteroaryl;

R$^3$ is hydrogen or optionally substituted alkyl;

R$^4$ is hydrogen, halogen, optionally substituted alkyl, or —Si(R$^A$)$_3$;

R$^5$ is —OR$^A$, —OC(=O)R$^A$, —OC(=O)OR$^A$, —OC(=O)N(R$^A$)$_2$, —OS(=O)$_2$R$^A$, —N$_3$, —N(R$^A$)$_2$, —NR$^A$C(=O)R$^A$, —NR$^A$C(=O)OR$^A$, —NR$^A$C(=O)N(R$^A$)$_2$, —NR$^A$S(=O)$_2$R$^A$, or —C(R$^A$)$_3$;

each instance of ⁓, designated as (a), (b), and (c), represents a single or double bond, provided that when ⁓ designated as (c) represents a double bond, then one of R$^{B1}$ and R$^{B2}$ is absent, and provided that when ⁓ designated as (c) represents a single bond, then both R$^{B1}$ and R$^{B2}$ are present;

each instance of R$^{B1}$ and R$^{B2}$ is, independently, hydrogen, —L$_1$—R$^{B3}$, or —X$^A$R$^A$ wherein X$^A$ is —O—, —S—, or —N(R$^A$)—; or R$^{B1}$ and R$^{B2}$ are joined to form an oxo group, provided that at least one of R$^{B1}$ and R$^{B2}$ is not hydrogen;

L$_1$ is a bond, —C(=O)—, —C(=O)O—, —C(=O)S—, —C(=O)N(R$^L$)—, or —N(R$^L$)—(C(R$^{LL}$)$_2$)$_p$—, wherein R$^L$ is hydrogen, optionally substituted alkyl, or a nitrogen protecting group, each instance of R$^{LL}$ is independently hydrogen, halogen, or optionally substituted alkyl, and p is 0, 1, or 2;

R$^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when L$_1$ is a bond, then R$^{B3}$ is not hydrogen;

each instance of R$^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen, optionally when attached to N the two R$^A$ groups may be joined to form an optionally substituted heterocyclyl or optionally substituted heteroaryl ring, and optionally when R$^{B1}$ and R$^{B2}$ are each —X$^A$R$^A$ then two R$^A$ groups may be joined to form an optionally substituted heterocyclyl ring; and R$^O$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^A$, —C(=O)OR$^A$, —C(=O)N(R$^A$)$_2$, or an oxygen protecting group.

It is generally understood that any atom encompassed by any of the formula described herein may be replaced with an isotope of that atom, e.g., for example, a hydrogen atom ($^1$H) may be replaced with a deuterium ($^2$H, D) or tritium ($^3$H, T) atom, a carbon atom ($^{12}$C) may be replaced with its $^{14}$C isotope, and a fluorine atom ($^{18}$F) may be replaced by its $^{19}$F isotope.

In one embodiment, the present invention includes compounds of Formulas (A'), (B'), (C'), (D'), (E'), (A"), (B"), (C"), (D"), (E"), (G1), and (G2) and additional active compounds described herein, and the use of these compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A typical isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group when at least one of the variables within the R group is hydrogen (e.g., $^2$H or D) or alkyl (e.g., CHD, CD$_2$, CD$_3$). For example, when any of R groups are, or contain for example through substitution, methyl, ethyl, or another alkyl group, the alkyl residue can be deuterated, e.g., CD$_3$, CH$_2$CD$_3$ or CD$_2$CD$_3$. In certain other embodiments, when any of the above mentioned R groups are hydrogen, the hydrogen may be isotopically enriched as deuterium (i.e., $^2$H).

In some embodiments, R$^{B1}$ is deuterium. In some embodiments, R$^{B1}$ comprises an isotopically enriched atom (e.g., $^2$H, $^3$H, $^{13}$C, $^{14}$C, $^{18}$F). In some embodiments, R$^{B2}$ is deuterium. In some embodiments, R$^{B2}$ comprises an isotopically enriched atom (e.g., $^2$H, $^3$H, $^{13}$C $^{14}$C, $^{18}$F). In some embodiments, $R^3$ is deuterium. In some embodiments, $R^3$ comprises an isotopically enriched atom (e.g., $^2H$, $^3H$, $^{13}C$, $^{14}C$, $^{18}F$). In some embodiments, $R^4$ is deuterium. In some embodiments, $R^4$ comprises an isotopically enriched atom (e.g., $^2H$, $^3H$, $^{13}C$, $^{14}C$, $^{18}F$). In some embodiments, $R^5$ is deuterium. In some embodiments, $R^5$ comprises an isotopically enriched atom (e.g., $^2H$, $^3H$, $^{13}C$, $^{14}C$, $^{18}F$). In some embodiments, $R^O$ is deuterium. In some embodiments, $R^O$ comprises an isotopically enriched atom (e.g., $^2H$, $^3H$, $^{13}C$, $^{14}C$, $^{18}F$). In some embodiments, $R^1$ or $R^2$ is deuterium. In some embodiments, $R^1$ or $R^2$ comprises an isotopically enriched atom (e.g., $^2H$, $^3H$, $^{13}C$, $^{14}C$, $^{18}F$). In some embodiments, a hydrogen on ring A (see below) is substituted with deuterium. In some embodiments, a hydrogen on ring B is substituted with deuterium. In some embodiments, a hydrogen on ring C is substituted with deuterium. In some embodiments, a hydrogen on ring D is substituted with deuterium.

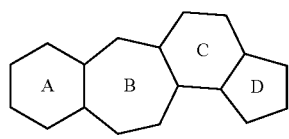

cortistatin ring labeling

In some embodiments, $R^5$ or another position of ring A is deuterated by trapping of an enolate with a deuterium source, such as $D_2O$ or a deuterated acid. In some embodiments, a position of ring B, C, or D is deterated by reduction of double bond (a), (b), or (c) respectively with a deuterium source (e.g., $D_2$, HD, a deuterated borohydride). In some embodiments, a position of ring D is deteurated by trapping of an enolate (e.g., for a compound of Formula (XXI)) with a deuterium source, such as $D_2O$ or a deuterated acid.

In general, reductive amination of Formula (B') or (B") generally provides both alpha and beta aminated isomers encompassed by Formula (A') or (A"), referred to herein as Formula (A-1') or (A-1"), the beta isomer, and Formula (A-2') or (A-2"), the alpha isomer. In certain embodiments, the beta isomer is the major product of the reaction. In other embodiments, the alpha isomer is the major product of the reaction. The alpha isomer shares C3 stereochemistry with other cortistatin natural products. Furthermore, reduction of the ketone generally provides both alpha and beta reduced isomers encompassed by Formula (D') or (D"), referred to herein as Formula (D-1') or (D-1"), the beta isomer, and Formula (D-2') or (D-2"), the alpha isomer. Subsequent protection of these isomers of Formula (D') or (D") respectively provides Formula (E-1') or (E-1"), the beta isomer, and Formula (E-2') or (E-2"), the alpha isomer.

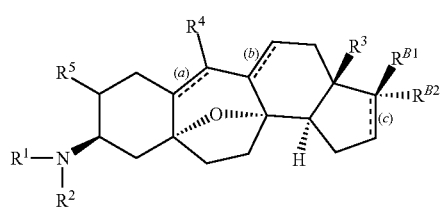
(A-1')

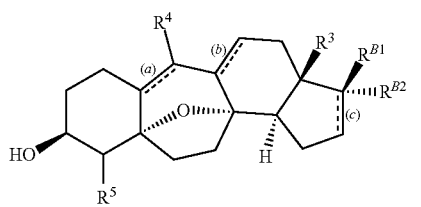
(D-1')

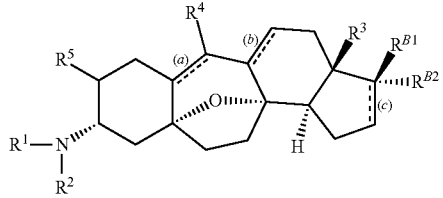
(A-2')

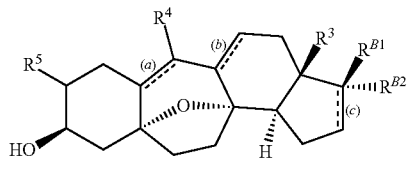
(D-1')

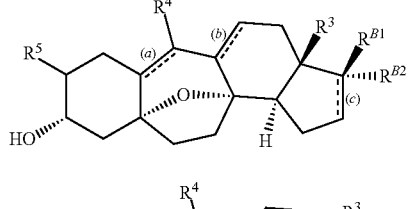
(D-2')

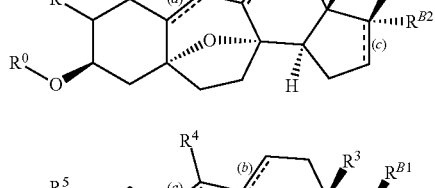
(E-1')

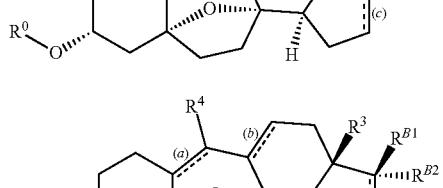
(E-2')

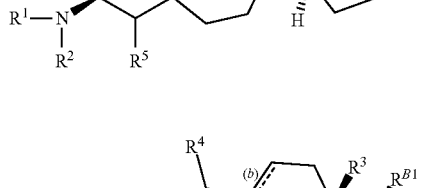
(A-1")

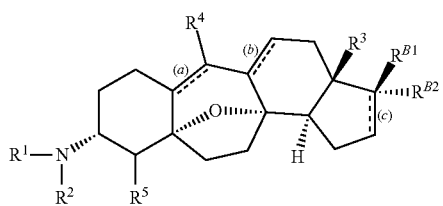
(A-2")

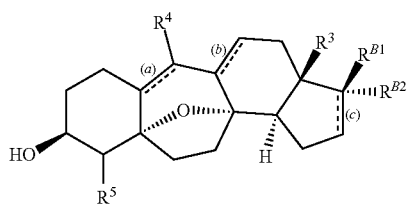
(D-1")

(D-2″)
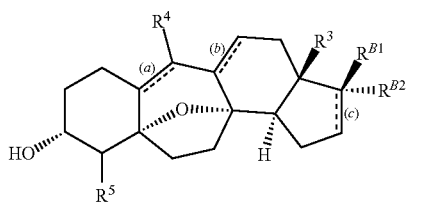

(E-1″)
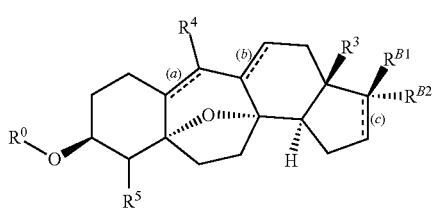

(E-2″)
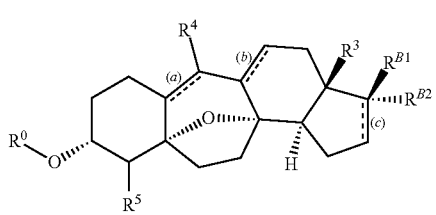

Quaternary Amine Salts and N-Oxides

In certain embodiments, as provided, a compound of Formula (A′), (B′), (C′), (D′), (E′), (A″), (B″), (C″), (D″), (E″), (G1), or (G2) may comprise a quaternary amine salt and/or an N-oxide.

A "quaternary amine salt" as used herein refers to an amino group wherein the nitrogen atom comprises four valence bonds (e.g., is substituted with four groups which may be hydrogen and/or non-hydrogen groups) such that the nitrogen atom is positively charged and the charge is balanced (neutralized) with a counteranion (e.g., $X^C$ as defined herein).

An "N-oxide" as used herein refers to an amino group wherein the nitrogen atom comprises four valence bonds (e.g, is substituted with four groups which may be hydrogen and/or non-hydrogen groups, wherein one group directly attached to the nitrogen atom is an oxidyl group ($-O^{\ominus}$)) such that the nitrogen atom is positively charged, and wherein the oxidyl group balances (neutralizes) the positive charge of the nitrogen atom.

It should be understood that any one of Formula (A′), (B′), (C′), (D′), (E′), (A″), (B″), (C″), (D″), (E″), (G1), or (G2) may comprise quaternary amine salt and/or N-oxide groups at any position where an amino group may be located.

In particular, compounds of Formula (A′) or (A″) may comprise a quaternary amine salt or N-oxide group at the $C_3$ position (also referred to as a "quaternary C3-amine salt" and "C3-N-oxide"), which comprises the amino group $-NR_1R_2$ attached to Ring A.

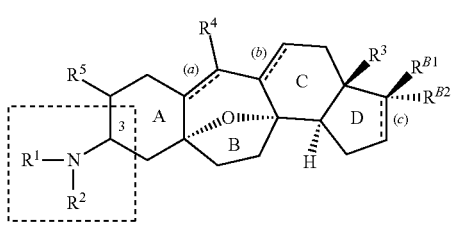

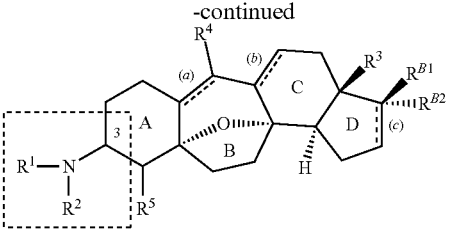

In certain embodiments, the amino group

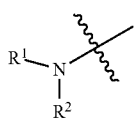

at the $C_3$ position may be an quaternary amine salt formula

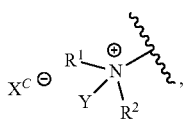

e.g., to provide a compound of Formula (A-QA′) or (A-QA″):

(A-QA′)
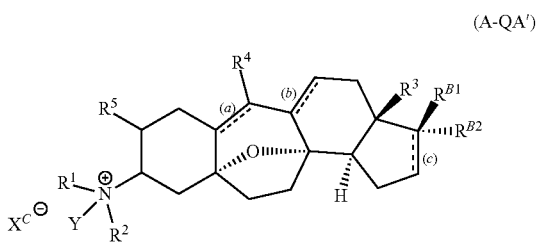

(A-QA″)
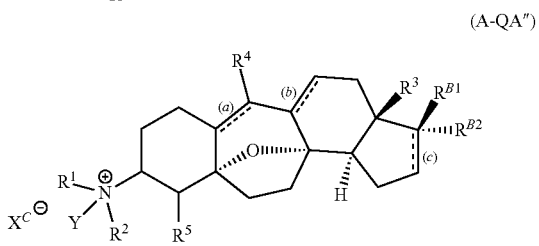

wherein ----, $R^1$, $R^2$, $R^3$, $R^4$, $R^5$, $R^{B1}$, and $R^{B2}$ are as defined herein; and wherein:

Y is optionally substituted alkyl, optionally substituted alkenyl, optionally substituted alkynyl, optionally substituted carbocyclyl, optionally substituted heterocyclyl, optionally substituted aryl, or optionally substituted heteroaryl; and $X^C$ is a counteranion.

A quaternary C3-amine salt may be formed by reaction of the free C3-amine with a group $Y-X^C$, wherein Y is defined above (e.g., optionally substituted alkyl, optionally substituted alkenyl, optionally substituted alkynyl, optionally substituted carbocyclyl, or optionally substituted heterocyclyl), and $X^C$ is a leaving group as defined herein. The counterion $X^C$ resulting therefrom may be exchanged with another counterion $X^C$ by ion exchange methods, e.g., ion exchange chromatography. Exemplary $X^C$ counterions include but are not limited to halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like). In certain embodiments, Y is optionally substituted alkyl (e.g., methyl). In certain embodiments, $X^C$ is a halide ion.

In certain embodiments, the quaternary amine salt of Formula (A-QA') or Formula (A-QA") is the beta (A-1-QA') or (A-1-QA") or alpha (A-2-QA') or (A-2-QA") isomer of the following Formula:

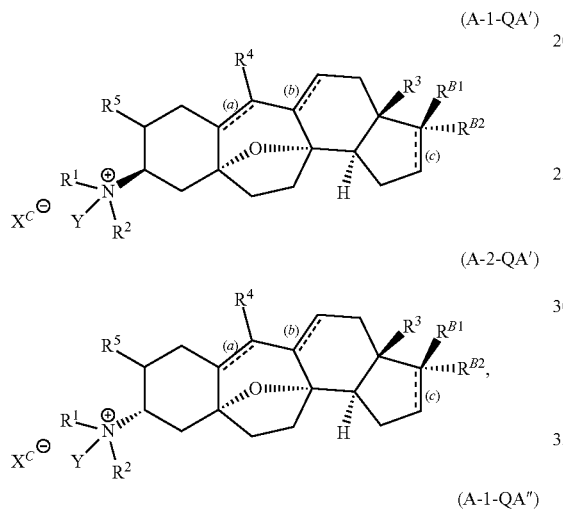

(A-1-QA')

(A-2-QA')

(A-1-QA")

(A-2-QA")

wherein ~~~, $R^1$, $R^2$, $R^3$, $R^4$, $R^5$, $R^{B1}$, and $R^{B2}$ are as defined herein.

Alternatively, in certain embodiments, the amino group

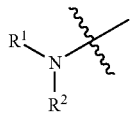

at the $C_3$ position may be an N-oxide of formula

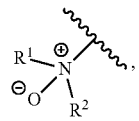

e.g., to provide a compound of Formula:

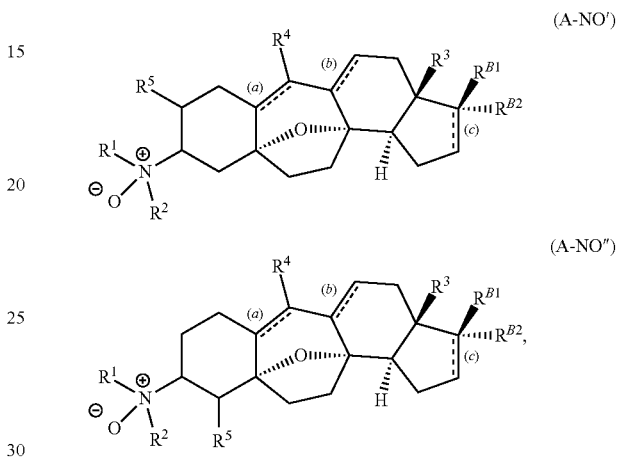

(A-NO')

(A-NO")

wherein ~~~, $R^1$, $R^2$, $R^3$, $R^4$, $R^5$, $R^{B1}$, and $R^{B2}$ are as defined herein.

In certain embodiments, the N-oxide of Formula (A-NO') or (A-NO") is the beta (A-1-NO') or (A-1-NO") or alpha (A-2-NO') or (A-2-NO") isomer of the following Formula:

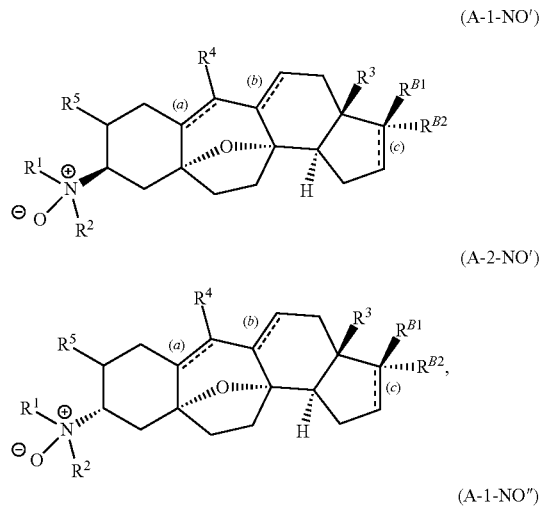

(A-1-NO')

(A-2-NO')

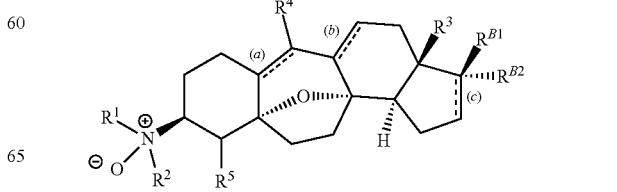

(A-1-NO")

(A-2-NO″)

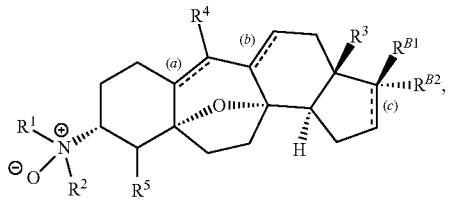

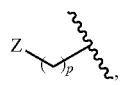

e.g., to provide a compound of Formula:

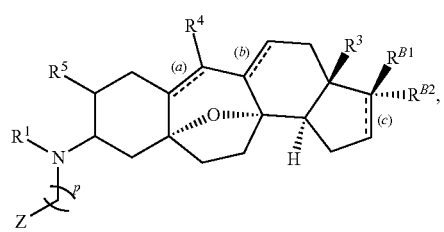
(A-f′)

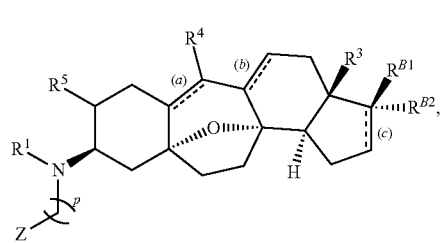
(A-1-f′)

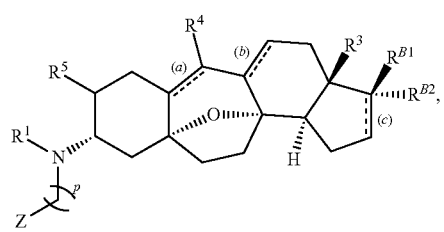
(A-2-f′)

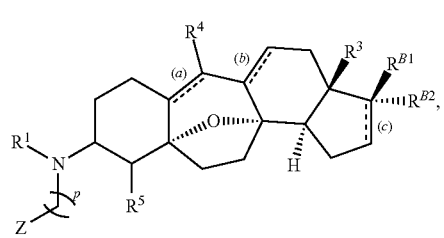
(A-f″)

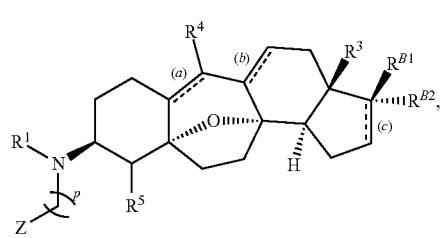
(A-1-f″)

wherein ----, $R^1$, $R^2$, $R^3$, $R^4$, $R^5$, $R^{B1}$, and $R^{B2}$ are as defined herein.

Groups $R^1$ and $R^2$

As generally defined herein, in certain embodiments of Formula (A′) or (A″) and (C), $R^1$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —$SR^A$, —$N(R^A)_2$, —$C(=O)R^A$, —$C(=O)OR^A$, —$C(=O)N(R^A)_2$, —$S(=O)_2R^A$, or a nitrogen protecting group.

Furthermore, in certain embodiments of Formula (A′) or (A″), $R^2$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$C(=O)R^A$, —$C(=O)OR^A$, —$C(=O)N(R^A)_2$, —$S(=O)_2R^A$, or a nitrogen protecting group.

For example, in certain embodiments of Formula (A′) or (A″), at least one of $R^1$ and $R^2$ is hydrogen. In certain embodiments of Formula (A′) or (A″), both of $R^1$ and $R^2$ is hydrogen. In certain embodiments of Formula (A′) or (A″), one of $R^1$ and $R^2$ is hydrogen and the other is a non-hydrogen group, e.g, optionally substituted alkyl. In certain embodiments of Formula (C′) or (C″), $R^1$ is hydrogen.

In certain embodiments of Formula (A′) or (A″), at least one of $R^1$ and $R^2$ is optionally substituted alkyl, e.g., optionally substituted $C_{1-6}$alkyl. In certain embodiments of Formula (A′) or (A″), each instance of $R^1$ and $R^2$ is independently optionally substituted alkyl. In certain embodiments of Formula (C′) or (C″), $R^1$ is optionally substituted alkyl, e.g., optionally substituted $C_{1-6}$alkyl. In certain embodiments, $R^1$ and/or $R^2$ is optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments, $R^1$ and/or $R^2$ is optionally substituted methyl ($C_1$), optionally substituted ethyl ($C_2$), optionally substituted n-propyl ($C_3$), optionally substituted isopropyl ($C_3$), optionally substituted n-butyl ($C_4$), or optionally substituted t-butyl ($C_4$). In certain embodiments, $R^1$ and/or $R^2$ is alkyl substituted with one or more halogen substitutents (e.g., fluoro). In certain embodiments, $R^1$ and/or $R^2$ is —$CH_3$ or —$CF_3$. In certain embodiments, each instance of $R^1$ and $R^2$ is independently —$CH_3$ or —$CF_3$. In certain embodiments, $R^1$ and/or $R^2$ is alkyl substituted with one or more halogen (e.g., fluoro), amino (—$NH_2$), substituted amino, hydroxyl (—OH), substituted hydroxyl, thiol (—SH), substituted thiol, or sulfonyl substituents. In certain embodiments, $R^1$ and/or $R^2$ is alkyl substituted with an optionally substituted carbocyclyl (e.g., cyclopropyl) or optionally substituted heterocyclyl (e.g., oxetanyl) ring.

For example, in certain embodiments, at least one of $R^1$ and $R^2$ is a group of formula:

-continued

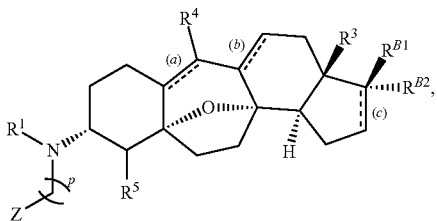

(A-2-f'')

or a pharmaceutically acceptable salt, quaternary amine salt, or N-oxide thereof,
wherein ----, $R^1$, $R^3$, $R^4$, $R^5$, $R^{B1}$, and $R^{B2}$ are as defined herein; and
wherein:
p is 1, 2, 3, 4, 5, or 6; and
Z is —$CH_2X^Z$, —$CH(X^Z)_2$, —$C(X^Z)_3$, —$OR^Z$, —$SR^Z$, —$N(R^Z)_2$, —$S(O)_2N(R^Z)_2$,

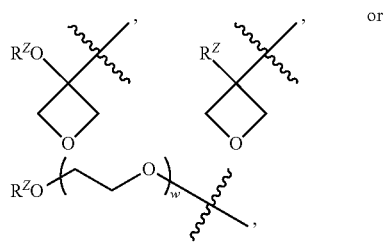

wherein each instance of $R^Z$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^Z$, —C(=O)O$R^Z$, —C(=O)N($R^Z$)$_2$, an oxygen protecting group when attached to oxygen, a sulfur protecting group when attached to sulfur, or a nitrogen protecting group when attached to nitrogen, optionally when attached to N the two $R^Z$ groups may be joined to form an optionally substituted heterocyclyl or optionally substituted heteroaryl ring;
each instance of $X^Z$ is independently fluoro, chloro, bromo, or iodo; and
w is an integer between 1 and 10, inclusive.

In certain embodiments, both instances of $R^1$ and $R^2$ are independently a group of formula

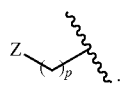

In certain embodiments, p is 1. In certain embodiments, p is 2. In certain embodiments, p is 3. In certain embodiments, w is 1, 2, 3, or 4. In certain embodiments, $R^Z$ is hydrogen or optionally substituted alkyl (e.g., —$CH_3$). In certain embodiments, Z is —$OR^Z$, e.g., —OH or —$OR^Z$ wherein $R^Z$ is a non-hydrogen group, e.g., wherein $R^Z$ is optionally substituted alkyl such as —$CH_3$. In certain embodiments, Z is —$N(R^Z)_2$, e.g., —$NH_2$, —$NHR^Z$, or —$N(R^Z)_2$ wherein $R^Z$ is a non-hydrogen group, e.g., wherein $R^Z$ is optionally substituted alkyl such as —$CH_3$. In certain embodiments, Z is —$CH_2X^Z$, —$CH(X^Z)_2$, or —$C(X^Z)_3$, e.g., wherein $X^Z$ is fluoro. In certain embodiments, Z is —$S(O)_2N(R^Z)_2$, e.g., —$S(O)_2NH_2$ or —$S(O)_2NHCH_3$.

In certain embodiments of Formula (A') or (A"), at least one of $R^1$ and $R^2$ is optionally substituted alkenyl, e.g., optionally substituted $C_{2-6}$alkenyl. In certain embodiments of Formula (A') or (A"), both of $R^1$ and $R^2$ is optionally substituted alkenyl. In certain embodiments of Formula (C') or (C"), $R^1$ is optionally substituted alkenyl, e.g., optionally substituted $C_{2-6}$alkenyl. In certain embodiments, $R^1$ and/or $R^2$ is optionally substituted $C_2$alkenyl, optionally substituted $C_3$alkenyl, optionally substituted $C_4$alkenyl, optionally substituted $C_5$alkenyl, or optionally substituted $C_6$alkenyl. In certain embodiments, $R^1$ and/or $R^2$ is optionally substituted vinyl ($C_2$) or optionally substituted allyl ($C_3$).

In certain embodiments of Formula (A') or (A"), at least one of $R^1$ and $R^2$ is optionally substituted alkynyl, e.g., optionally substituted $C_{2-6}$alkynyl. In certain embodiments of Formula (A') or (A"), both of $R^1$ and $R^2$ is optionally substituted alkynyl. In certain embodiments of Formula (C') or (C"), $R^1$ is optionally substituted alkynyl, e.g., optionally substituted $C_{2-6}$alkynyl. In certain embodiments, $R^1$ and/or $R^2$ is optionally substituted $C_2$alkynyl, optionally substituted $C_3$alkynyl, optionally substituted $C_4$alkynyl, optionally substituted $C_5$alkynyl, or optionally substituted $C_6$alkynyl. In certain embodiments, $R^1$ and/or $R^2$ is optionally substituted acetylenyl ($C_2$) or optionally substituted propargyl ($C_3$).

In certain embodiments of Formula (A') or (A"), at least one of $R^1$ and $R^2$ is optionally substituted carbocyclyl, e.g., optionally substituted $C_{3-6}$carbocyclyl. In certain embodiments of Formula (A') or (A"), both of $R^1$ and $R^2$ is optionally substituted carbocyclyl. In certain embodiments of Formula (C') or (C"), $R^1$ is optionally substituted carbocyclyl, e.g., optionally substituted $C_{3-6}$carbocyclyl. In certain embodiments, $R^1$ and/or $R^2$ is optionally substituted $C_3$ carbocyclyl, optionally substituted $C_4$ carbocyclyl, optionally substituted $C_5$ carbocyclyl, or optionally substituted $C_6$ carbocyclyl. In certain embodiments, $R^1$ and/or $R^2$ is optionally substituted cyclopropyl ($C_3$), optionally substituted cyclobutyl ($C_4$), optionally substituted cyclopenyl ($C_5$), or optionally substituted cyclohexyl ($C_6$).

In certain embodiments of Formula (A') or (A"), at least one of $R^1$ and $R^2$ is optionally substituted heterocyclyl, e.g., optionally substituted 3-6 membered heterocyclyl. In certain embodiments of Formula (A') or (A"), both of $R^1$ and $R^2$ is optionally substituted heterocyclyl. In certain embodiments of Formula (C') or (C"), $R^1$ is optionally substituted heterocyclyl, e.g., optionally substituted 3-6 membered heterocyclyl. In certain embodiments, $R^1$ and/or $R^2$ is optionally substituted 3-membered heterocyclyl (e.g., optionally substituted oxetanyl), optionally substituted 4-membered heterocyclyl, optionally substituted 5-membered heterocyclyl, or optionally substituted 6-membered heterocyclyl, e.g., optionally substituted 6-membered heterocyclyl comprising 1 or 2 heteroatoms selected from oxygen, sulfur, or nitrogen.

In certain embodiments of Formula (A') or (A"), at least one of $R^1$ and $R^2$ is optionally substituted aryl, e.g., optionally substituted phenyl. In certain embodiments of Formula (A') or (A"), both of $R^1$ and $R^2$ is optionally substituted phenyl. In certain embodiments of Formula (C') or (C"), $R^1$ is optionally substituted aryl, e.g., optionally substituted phenyl.

In certain embodiments of Formula (A') or (A"), at least one of $R^1$ and $R^2$ is optionally substituted heteroaryl, e.g., optionally substituted 5-6 membered heteroaryl. In certain embodiments of Formula (A') or (A"), both of $R^1$ and $R^2$ is optionally substituted heteroaryl. In certain embodiments of Formula (C') or (C"), $R^1$ is optionally substituted heteroaryl, e.g., optionally substituted 5-6 membered heteroaryl.

In certain embodiments of Formula (A') or (A") and (C), $R^1$ is —$OR^A$, e.g., —OH or —$OCH_3$. In certain embodiments of Formula (A') or (A") and (C), $R^1$ is —$SR^A$. In certain embodiments of Formula (A') or (A") and (C), $R^1$ is —$N(R^A)_2$.

In certain embodiments of Formula (A') or (A"), at least one of $R^1$ and $R^2$ is —C(=O)$R^A$, —C(=O)O$R^A$, or —C(=O)N($R^A)_2$. In certain embodiments of Formula (C') or (C"), $R^1$ is —C(=O)$R^A$, —C(=O)O$R^A$, or —C(=O)N($R^A)_2$.

In certain embodiments of Formula (A') or (A"), at least one of $R^1$ and $R^2$ is a nitrogen protecting group. In certain embodiments of Formula (C') or (C"), $R^1$ is a nitrogen protecting group.

Furthermore, as generally defined herein, in certain embodiments of Formula (A') or (A"), $R^1$ and $R^2$ are joined to form an optionally substituted heterocyclyl or optionally substituted heteroaryl.

In certain embodiments of Formula (A') or (A"), at least one of $R^1$ and $R^2$ is —$S(O)_2R^A$. In certain embodiments, $R^A$ is optionally substituted alkyl (e.g., —$CH_3$). In certain embodiments of Formula (A') or (A"), one of $R^1$ and $R^2$ is —$S(O)_2R^A$ and the other is optionally substituted alkyl (e.g., —$CH_3$). In certain embodiments of Formula (C') or (C"), $R^1$ is —$S(O)_2R^A$.

In certain embodiments of Formula (A') or (A"), $R^1$ and $R^2$ are joined to form an optionally substituted heterocyclyl, e.g., an optionally substituted 3-6 membered heterocyclyl. In certain embodiments of Formula (A') or (A"), $R^1$ and $R^2$ are joined to form an optionally substituted 3-membered heterocyclyl, an optionally substituted 4-membered heterocyclyl, optionally substituted 5-membered heterocyclyl, or an optionally substituted 6-membered heterocyclyl. In certain embodiments, $R^1$ and $R^2$ are joined to form an optionally substituted 3-membered heterocyclyl, i.e., an optionally substituted aziridinyl. In certain embodiments, $R^1$ and $R^2$ are joined to form an optionally substituted 4-membered heterocyclyl, e.g., an optionally substituted azetidinyl. In certain embodiments, $R^1$ and $R^2$ are joined to form an optionally substituted 5-membered heterocyclyl, e.g., an optionally substituted pyrrolidinyl or optionally substituted imidazolidine-2,4-dione. In certain embodiments, $R^1$ and $R^2$ are joined to form an optionally substituted 6-membered heterocyclyl, e.g., an optionally substituted piperidinyl, optionally substituted tetrahydropyranyl, optionally substituted dihydropyridinyl, optionally substituted thianyl, optionally substituted piperazinyl, optionally substituted morpholinyl, optionally substituted dithianyl, optionally substituted dioxanyl, or optionally substituted triazinanyl.

For example, in certain embodiments, $R^1$ and $R^2$ are joined to form a group of formula:

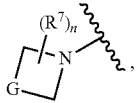

e.g., to provide a compound of Formula:

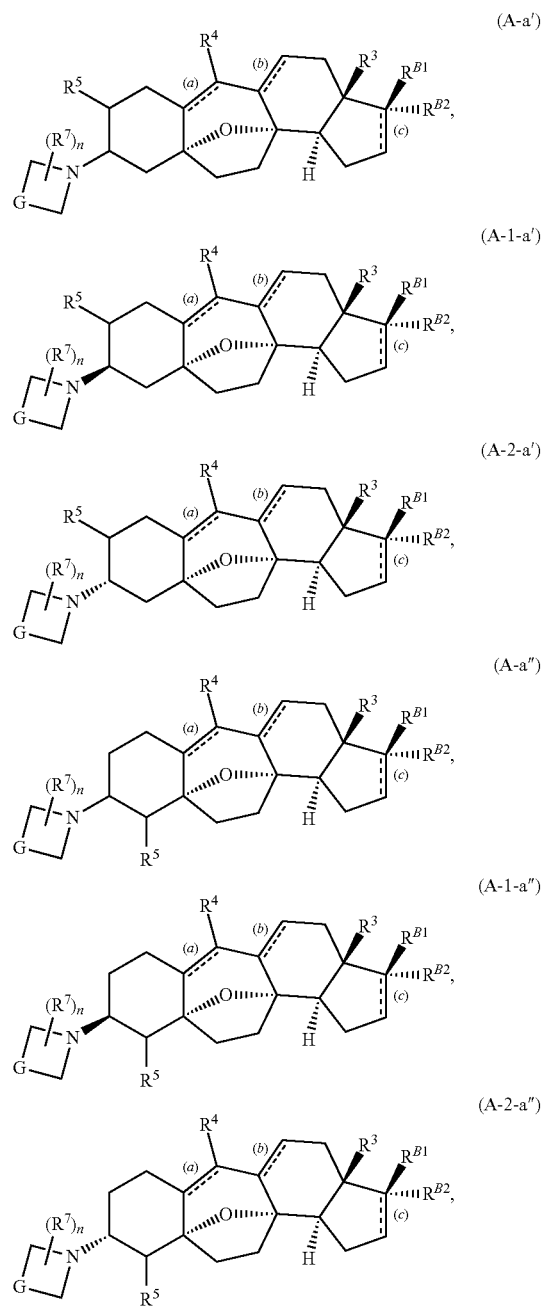

or a pharmaceutically acceptable salt, quaternary amine salt, or N-oxide thereof, wherein ⁓, $R^3$, $R^4$, $R^5$, $R^{B1}$, and $R^{B2}$ are as defined herein; and
wherein:
G is —O—, —S—, —NH—, —$NR^7$—, —$CH_2$—, —CH(R')—, or —$C(R^7)_2$—;

each instance of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, amino, substituted amino, hydroxyl, substituted hydroxyl, thiol, substituted thiol, carbonyl, sulfonyl, sulfinyl, or a nitrogen protecting group when attached to a nitrogen atom;

optionally wherein two $R^7$ groups are joined to form an optionally substituted carbocyclyl, optionally substituted heterocyclyl, optionally substituted aryl, an optionally substituted heteroaryl ring, or an oxo (=O) group; and n is 0, 1, 2, 3, or 4.

In certain embodiments, $R^1$ and $R^2$ are joined to form a group of formula:

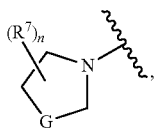

e.g., to provide a compound of formula:

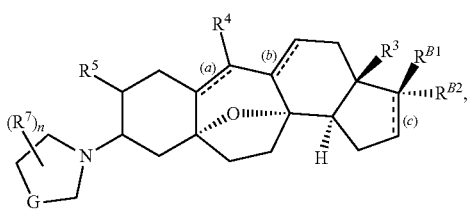
(A-b')

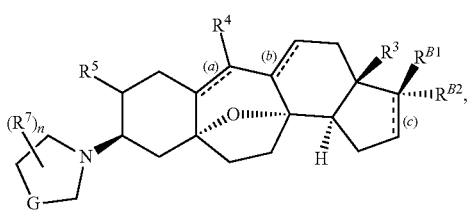
(A-1-b')

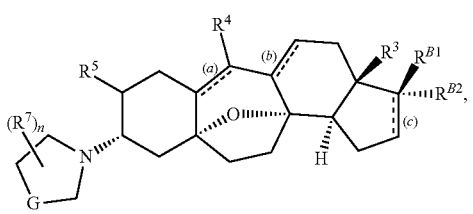
(A-2-b')

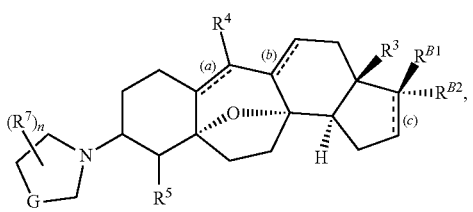
(A-b")

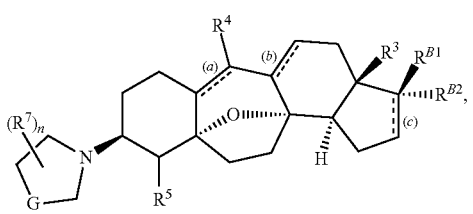
(A-1-b")

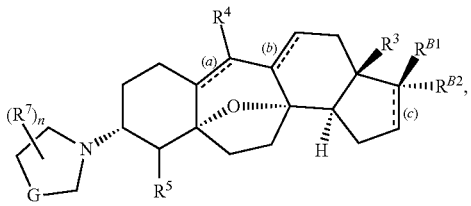
(A-2-b")

or a pharmaceutically acceptable salt, quaternary amine salt, or N-oxide thereof, wherein ⁓, $R^3$, $R^4$, $R^5$, $R^{B1}$, and $R^{B2}$ are as defined herein; and wherein:

G is —O—, —S—, —NH—, —NR$^7$—, —CH$_2$—, —CH(R$^7$)—, or —C(R$^7$)$_2$—;

each instance of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, amino, substituted amino, hydroxyl, substituted hydroxyl, thiol, substituted thiol, carbonyl, sulfonyl, sulfinyl, or a nitrogen protecting group when attached to a nitrogen atom;

optionally wherein two $R^7$ groups are joined to form an optionally substituted carbocyclyl, optionally substituted heterocyclyl, optionally substituted aryl, an optionally substituted heteroaryl ring, or an oxo (=O) group; and n is 0, 1, 2, 3, or 4.

In certain embodiments, $R^1$ and $R^2$ are joined to form a group of formula:

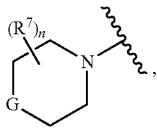

e.g., to provide a compound of Formula:

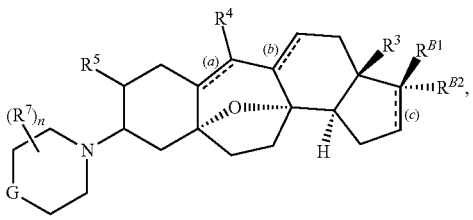
(A-c')

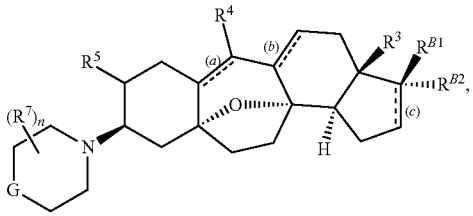
(A-1-c')

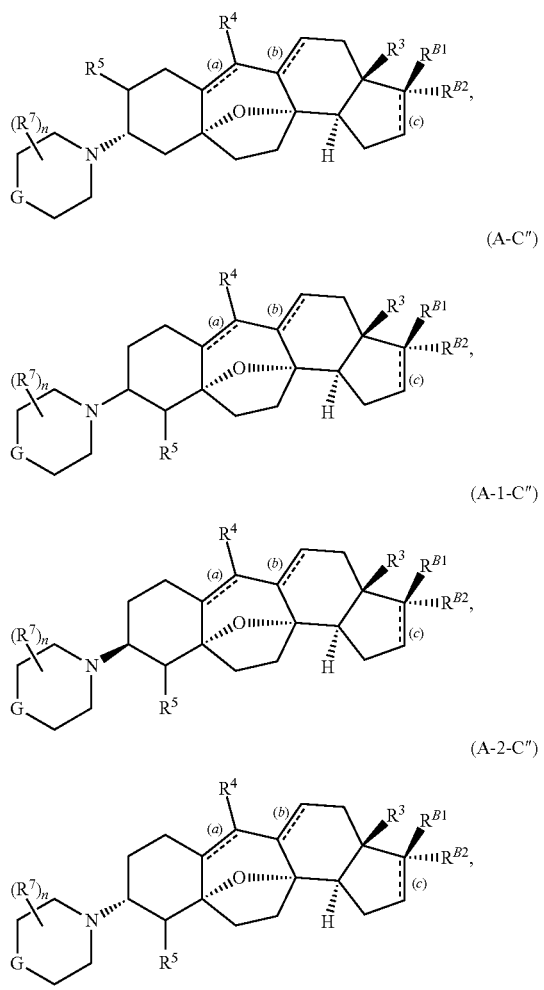

or a pharmaceutically acceptable salt, quaternary amine salt, or N-oxide thereof, wherein ---, $R^3$, $R^4$, $R^5$, $R^{B1}$, and $R^{B2}$ are as defined herein; and
wherein:
G is —O—, —S—, —NH—, —$NR^7$—, —$CH_2$—, —CH(R')—, or —$C(R^7)_2$—;
each instance of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, amino, substituted amino, hydroxyl, substituted hydroxyl, thiol, substituted thiol, carbonyl, sulfonyl, sulfinyl, or a nitrogen protecting group when attached to a nitrogen atom;
optionally wherein two $R^7$ groups are joined to form an optionally substituted carbocyclyl, optionally substituted heterocyclyl, optionally substituted aryl, an optionally substituted heteroaryl ring, or an oxo (=O) group; and
n is 0, 1, 2, 3, or 4.

In certain embodiments, n is 0, and the ring system formed by the joining of $R^1$ and $R^2$ is not substituted with an $R^7$ group as defined herein. In certain embodiments, n is 1, 2, 3, or 4, and the ring system is substituted with 1, 2, 3, or 4 $R^7$ groups as defined herein. In certain embodiments, n is 1. In certain embodiments, n is 2. In certain embodiments, n is 3. In certain embodiments, n is 4.

In certain embodiments, wherein n is not 0 (i.e., n is 1, 2, 3, or 4) and at least one $R^7$ is attached to a carbon atom, the $R^7$ is halogen (e.g., fluoro), hydroxyl, substituted hydroxyl, or carbonyl (e.g., —$CO_2H$). In certain embodiments, wherein n is not 0 (i.e., n is 1, 2, 3, or 4) and two $R^7$ groups are attached to the same carbon atom, the two $R^7$ groups are each halogen, e.g., fluoro. In certain embodiments, wherein n is not 0 (i.e., n is 1, 2, 3, or 4) and two $R^7$ groups are attached to the same carbon atom, the two $R^7$ groups are joined to form an optionally substituted carbocyclyl ring or optionally substituted heterocyclyl ring (e.g., optionally substituted oxetanyl ring). In certain embodiments, wherein n is not 0 (i.e., n is 1, 2, 3, or 4) and two $R^7$ groups are attached to a different carbon atom, the two $R^7$ groups are joined to form an optionally substituted carbocyclyl ring or optionally substituted heterocyclyl ring.

In certain embodiments, G is —O—. In certain embodiments, G is —$NR^7$—, e.g., wherein $R^7$ is optionally substituted alkyl (e.g., —$CH_3$). In certain embodiments, G is —CH($R^7$)— or —$C(R^7)_2$— wherein at least one $R^7$ is hydroxyl, substituted hydroxyl, or carbonyl (e.g., —$CO_2H$).

In certain embodiments, the group

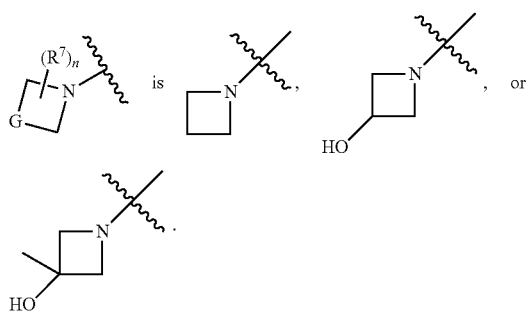

In certain embodiments, the group

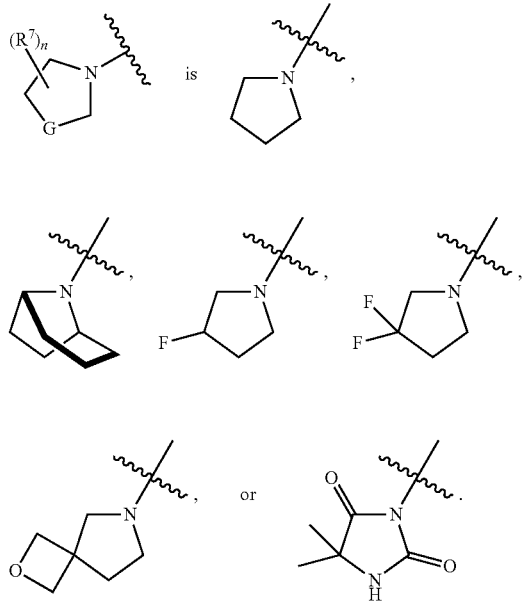

In certain embodiments, the group

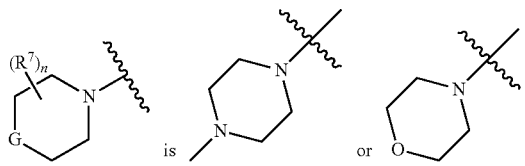

is

In certain embodiments of Formula (A') or (A"), $R^1$ and $R^2$ are joined to form an optionally substituted heteroaryl, e.g., an optionally substituted 5-membered heteroaryl or optionally substituted 6-membered heteroaryl.

Group $R^O$

As generally defined herein, for Formula (E') or (E"), $R^O$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^A$, —C(=O)O$R^A$, —C(=O)N($R^A$)$_2$, or an oxygen protecting group.

In certain embodiments of Formula (E') or (E"), $R^O$ is optionally substituted alkyl, e.g., optionally substituted $C_{1-6}$alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments, $R^O$ is optionally substituted methyl ($C_1$), optionally substituted ethyl ($C_2$), optionally substituted n-propyl ($C_3$), optionally substituted isopropyl ($C_3$), optionally substituted n-butyl ($C_4$), or optionally substituted t-butyl ($C_4$). In certain embodiments, $R^O$ is alkyl substituted with one or more halogen substitutents (e.g., fluoro). In certain embodiments, $R^O$ is —CH$_3$ or —CF$_3$. In certain embodiments, $R^O$ is alkyl substituted with one or more halogen (e.g., fluoro), amino (—NH$_2$), substituted amino, hydroxyl (—OH), substituted hydroxyl, thiol (—SH), substituted thiol, or sulfonyl substituents. In certain embodiments, $R^O$ is alkyl substituted with an optionally substituted carbocyclyl (e.g., cyclopropyl) or optionally substituted heterocyclyl (e.g., oxetanyl) ring.

For example, in certain embodiments, $R^O$ is a group of formula:

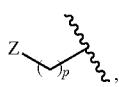

e.g., to provide a compound of Formula:

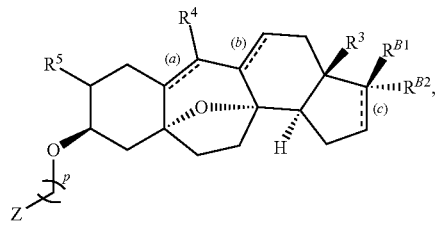 (E-f')

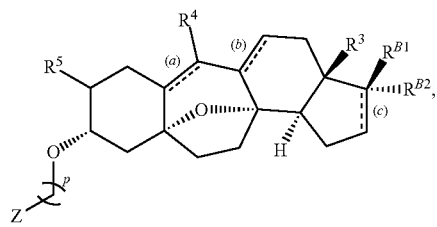 (E-1-f')

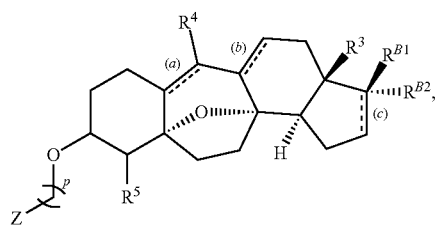 (E-2-f')

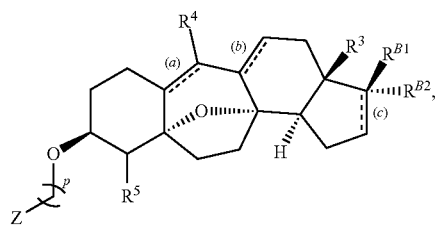 (E-f")

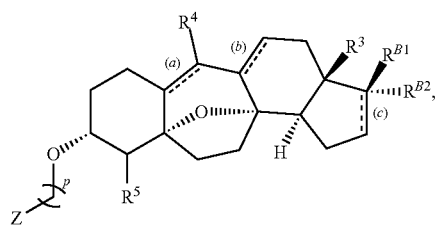 (E-1-f")

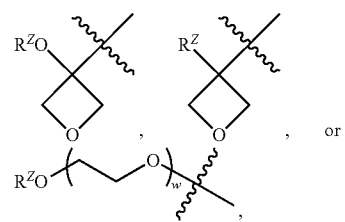 (E-2-f")

or a pharmaceutically acceptable salt, quaternary amine salt, or N-oxide thereof, wherein ---- $R^3$, $R^4$, $R^5$, $R^{B1}$, and $R^{B2}$ are as defined herein; and wherein:

p is 1, 2, 3, 4, 5, or 6; and

Z is —CH$_2$X$^Z$, —CH(X$^Z$)$_2$, —C(X$^Z$)$_3$, —OR$^Z$, —SR$^Z$, —N(R$^Z$)$_2$, —S(O)$_2$N(R$^Z$)$_2$,

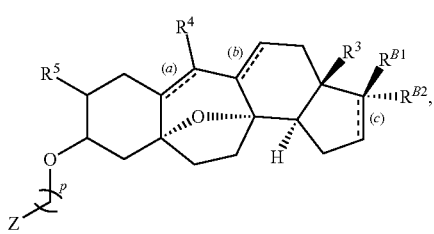

wherein each instance of $R^Z$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^Z$, —C(=O)O$R^Z$, —C(=O)N($R^Z$)$_2$, an oxygen protecting group when attached to oxygen, a sulfur protecting group when attached to sulfur, or a nitrogen protecting group when attached to nitrogen, optionally when attached to N the two $R^Z$ groups may be joined to form an optionally substituted heterocyclyl or optionally substituted heteroaryl ring;

each instance of $X^Z$ is independently fluoro, chloro, bromo, or iodo; and w is an integer between 1 and 10, inclusive.

In certain embodiments, p is 1. In certain embodiments, p is 2. In certain embodiments, p is 3. In certain embodiments, w is 1, 2, 3, or 4. In certain embodiments, $R^Z$ is hydrogen or optionally substituted alkyl (e.g., —CH$_3$). In certain embodiments, Z is —O$R^Z$, e.g., —OH or —O$R^Z$ wherein $R^Z$ is a non-hydrogen group, e.g., wherein $R^Z$ is optionally substituted alkyl such as —CH$_3$. In certain embodiments, Z is —N($R^Z$)$_2$, e.g., —NH$_2$, —NH$R^Z$, or —N($R^Z$)$_2$ wherein $R^Z$ is a non-hydrogen group, e.g., wherein $R^Z$ is optionally substituted alkyl such as —CH$_3$. In certain embodiments, Z is —CH$_2$$X^Z$, —CH($X^Z$)$_2$, —C($X^Z$)$_3$, e.g., wherein $X^Z$ is fluoro. In certain embodiments, Z is —S(O)$_2$N($R^Z$)$_2$, e.g., —S(O)$_2$NH$_2$ or —S(O)$_2$NHCH$_3$.

In certain embodiments of Formula (E') or (E"), $R^O$ is optionally substituted alkenyl, e.g., optionally substituted $C_{3-6}$alkenyl, e.g., optionally substituted $C_3$alkenyl, optionally substituted $C_4$alkenyl, optionally substituted $C_5$alkenyl, or optionally substituted $C_6$alkenyl.

In certain embodiments of Formula (E') or (E"), $R^O$ is optionally substituted alkynyl, e.g., optionally substituted $C_{3-6}$alkynyl, e.g., optionally substituted $C_3$alkynyl, optionally substituted $C_4$alkynyl, optionally substituted $C_5$alkynyl, or optionally substituted $C_6$alkynyl.

In certain embodiments of Formula (E') or (E"), $R^O$ is optionally substituted carbocyclyl, e.g., optionally substituted $C_{3-6}$carbocyclyl, e.g., optionally substituted $C_3$ carbocyclyl, optionally substituted $C_4$ carbocyclyl, optionally substituted $C_5$ carbocyclyl, or optionally substituted $C_6$ carbocyclyl. In certain embodiments, $R^O$ is optionally substituted cyclopropyl ($C_3$), optionally substituted cyclobutyl ($C_4$), optionally substituted cyclopenyl ($C_5$), or optionally substituted cyclohexyl ($C_6$).

In certain embodiments of Formula (E') or (E"), $R^O$ is optionally substituted heterocyclyl, e.g., optionally substituted 3-6 membered heterocyclyl, e.g., optionally substituted 3-membered heterocyclyl (e.g., optionally substituted oxetanyl), optionally substituted 4-membered heterocyclyl, optionally substituted 5-membered heterocyclyl, or optionally substituted 6-membered heterocyclyl, e.g., optionally substituted 6-membered heterocyclyl comprising 1 or 2 heteroatoms selected from oxygen, sulfur, or nitrogen.

In certain embodiments of Formula (E') or (E"), at least one of $R^1$ and $R^2$ is optionally substituted aryl, e.g., optionally substituted phenyl.

In certain embodiments of Formula (E') or (E"), $R^O$ is optionally substituted heteroaryl, e.g., optionally substituted 5-6 membered heteroaryl.

In certain embodiments of Formula (E') or (E"), $R^O$ is —C(=O)$R^A$, —C(=O)O$R^A$, or —C(=O)N($R^A$)$_2$. In certain embodiments, $R^A$ is hydrogen or optionally substituted alkyl (e.g., —CH$_3$). For example, in certain embodiments, $R^O$ is —C(=O)CH$_3$, —C(=O)OCH$_3$, —C(=O)N(CH$_3$)$_2$, or —C(=O)NHCH$_3$.

In certain embodiments of Formula (E') or (E"), $R^O$ is an oxygen protecting group.

Group $R^3$, $R^4$, $R^5$, and Bonds (a), (b), and (c) of Formula ⸺

As generally defined herein, for Formula (A'), (B'), (C'), (D'), (E'), (A"), (B"), (C"), (D"), (E"), (G1), and (G2), $R^3$ is hydrogen or optionally substituted alkyl.

In certain embodiments, $R^3$ is hydrogen. Such compounds are possible using starting materials such as 18-nor estrone.

In certain embodiments, $R^3$ is optionally substituted alkyl, e.g., methyl (—CH$_3$). Such compounds are possible by using starting materials such as estrone and tetralone for methyl.

As generally defined herein, for Formula (A'), (B'), (C'), (D'), (E'), (A"), (B"), (C"), (D"), (E"), (G1), and (G2), $R^4$ is hydrogen, halogen, optionally substituted alkyl, or —Si($R^A$)$_3$.

For example, in certain embodiments, $R^4$ is hydrogen. In certain embodiments, $R^4$ is optionally substituted alkyl, e.g., methyl. In certain embodiments, $R^4$ is —Si($R^A$)$_3$, e.g., wherein each instance of $R^A$ is independently optionally substituted alkyl or optionally substituted phenyl.

As generally defined herein, $R^5$ is —O$R^A$, —OC(=O)$R^A$, —OC(=O)O$R^A$, —OC(=O)N($R^A$)$_2$, —OS(=O)$_2$$R^A$, —N$_3$, —N($R^A$)$_2$, —N$R^A$C(=O)$R^A$, —N$R^A$C(=O)O$R^A$, —N$R^A$C(=O)N($R^A$)$_2$, —N$R^A$S(=O)$_2$$R^A$, or —C($R^A$)$_3$, wherein $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen, optionally when attached to N the two $R^A$ groups may be joined to form an optionally substituted heterocyclyl or optionally substituted heteroaryl ring.

In certain embodiments, $R^5$ is —O$R^A$, —OC(=O)$R^A$, —OC(=O)O$R^A$, —OC(=O)N($R^A$)$_2$, —OS(=O)$_2$$R^A$, wherein $R^A$ is as defined herein.

In certain embodiments, $R^5$ is —N$_3$, —N($R^A$)$_2$, —N$R^A$C(=O)$R^A$, —N$R^A$C(=O)O$R^A$, —N$R^A$C(=O)N($R^A$)$_2$, or —N$R^A$S(=O)$_2$$R^A$.

In certain embodiments, $R^5$ is —C($R^A$)$_3$.

In certain embodiments, the group $R^5$ is in the alpha (down) configuration. In certain embodiments, the group $R^5$ is in the beta (up) configuration.

As generally defined herein, each instance of ⸺, designated as (a), (b), and (c), represents a single or double bond, provided that when ⸺ designated as (c) represents a double bond, then one of $R^{B1}$ and $R^{B2}$ is absent, and provided that when ⸺ designated as (c) represents a single bond, then both $R^{B1}$ and $R^{B2}$ are present.

In certain embodiments, the bond ⸺ designated as (a) is a single bond. In certain embodiments, the bond ⸺ designated as (a) is a double bond.

In certain embodiments, the bond ⸺ designated as (b) is a single bond. In certain embodiments, the bond ⸺ designated as (b) is a double bond.

In certain embodiments, the bond ⸺ designated as (c) is a single bond. In certain embodiments, the bond ⸺ designated as (c) is a double bond, and $R^{B2}$ is absent.

In certain embodiments, the bond ⸺ designated as (a) is double bond, and the bond ⸺ designated as (b) is a double bond. In this instance, in certain embodiments, the bond ⸺ designated as (c) is a double bond, and $R^{B2}$ is absent. However, in this instance, in other embodiments, the bond ⸺ designated as (c) is a single bond.

Groups $R^{B1}$ and $R^{B2}$

As generally defined herein, each instance of $R^{B1}$ and $R^{B2}$ is, independently, hydrogen, —$L_1$—$R^{B3}$, or —$X^A R^A$ wherein $X^A$ is —O—, —S—, or —N($R^A$)—, provided that at least one of $R^{B1}$ and $R^{B2}$ is not hydrogen; or $R^{B1}$ and $R^{B2}$ are joined to form an oxo group;

$L_1$ is a bond, —C(=O)—, —C(=O)O—, —C(=O)S—, —C(=O)N($R^L$)—, or —N($R^L$)—(C($R^{LL}$)$_2$)$_p$—, wherein $R^L$ is hydrogen, optionally substituted alkyl, or a nitrogen protecting group, each instance of $R^{LL}$ is independently hydrogen, halogen, or optionally substituted alkyl, and p is 0, 1, or 2;

$R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when $L_1$ is a bond, then $R^{B3}$ is not hydrogen;

each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen; optionally when attached to N the two $R^A$ groups may be joined to form an optionally substituted heterocyclyl or optionally substituted heteroaryl ring; and optionally when $R^{B1}$ and $R^{B2}$ are each —$X^A R^A$ then two $R^A$ groups may be joined to form an optionally substituted heterocyclyl ring.

In certain embodiments, at least one instance of $R^{B1}$ and $R^{B2}$ is —$L_1$—$R^{B3}$. In this instance, in certain embodiments, the other of $R^{B1}$ and $R^{B2}$ is hydrogen or —$X^A R^A$ (e.g., —$OR^A$). For example, in certain embodiments, when ⸺ designated as (c) represents a single bond, then $R^{B1}$ is —$L_1$—$R^{B3}$ and $R^{B2}$ is hydrogen or —$X^A R^A$ (e.g., —$OR^A$). In other embodiments, when ⸺ designated as (c) represents a single bond, then $R^{B2}$ is —$L_1$—$R^{B3}$ and $R^{B1}$ is hydrogen or —$X^A R^A$ (e.g., —$OR^A$). Alternatively, in certain embodiments, when ⸺ designated as (c) represents a double bond, then $R^{B1}$ is —$L_1$—$R^{B3}$ and $R^{B2}$ is absent.

For example, in certain embodiments wherein $R^{B1}$ is —$L_1$—$R^{B3}$, provided are compounds of Formula:

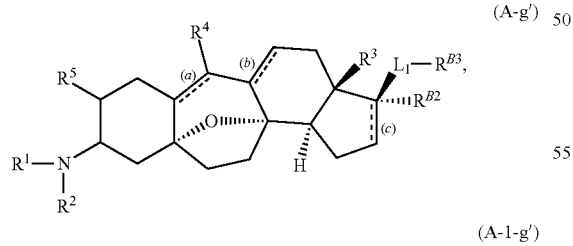

(A-g')

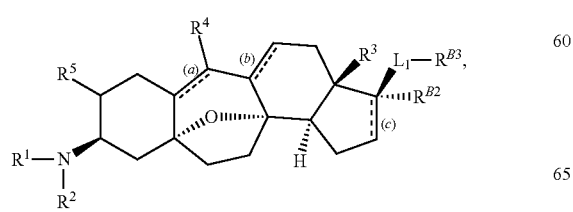

(A-1-g')

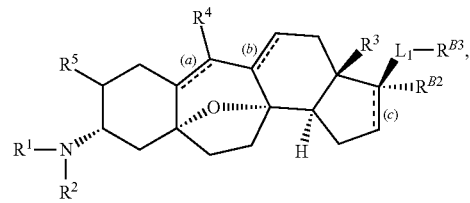

(A-2-g')

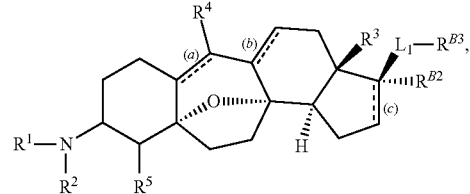

(A-g'')

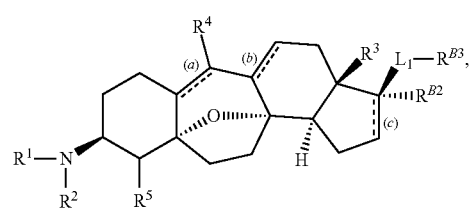

(A-1-g'')

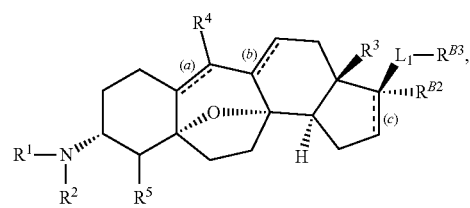

(A-2-g'')

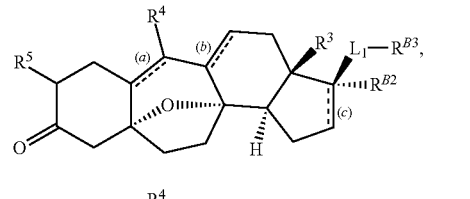

(B-g)

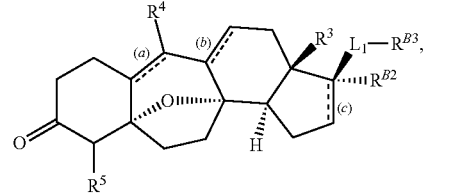

(B-g'')

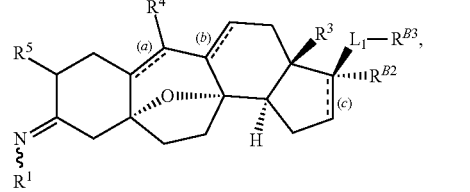

(C-g)

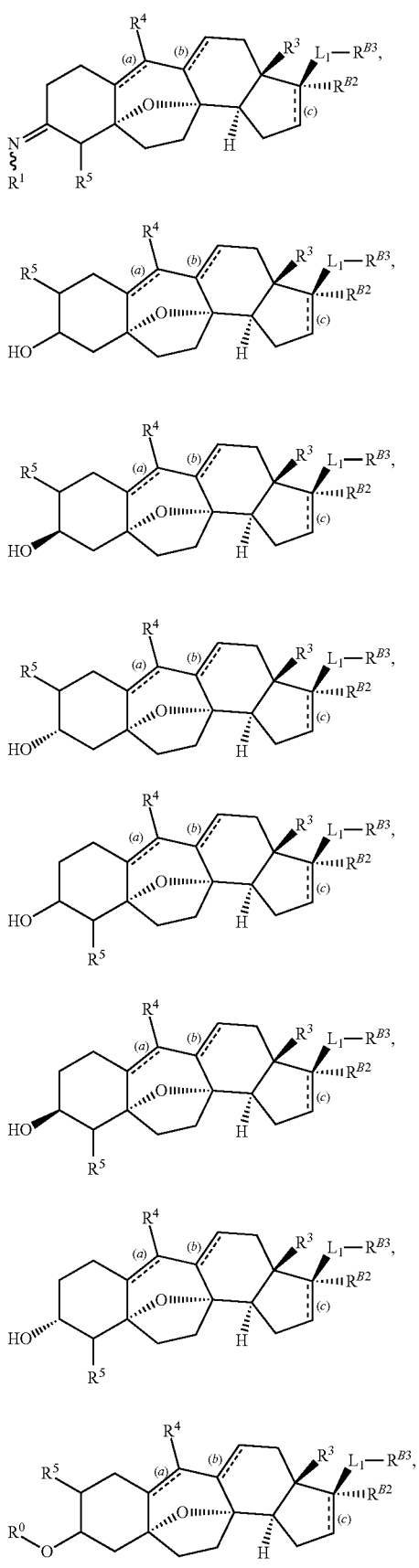
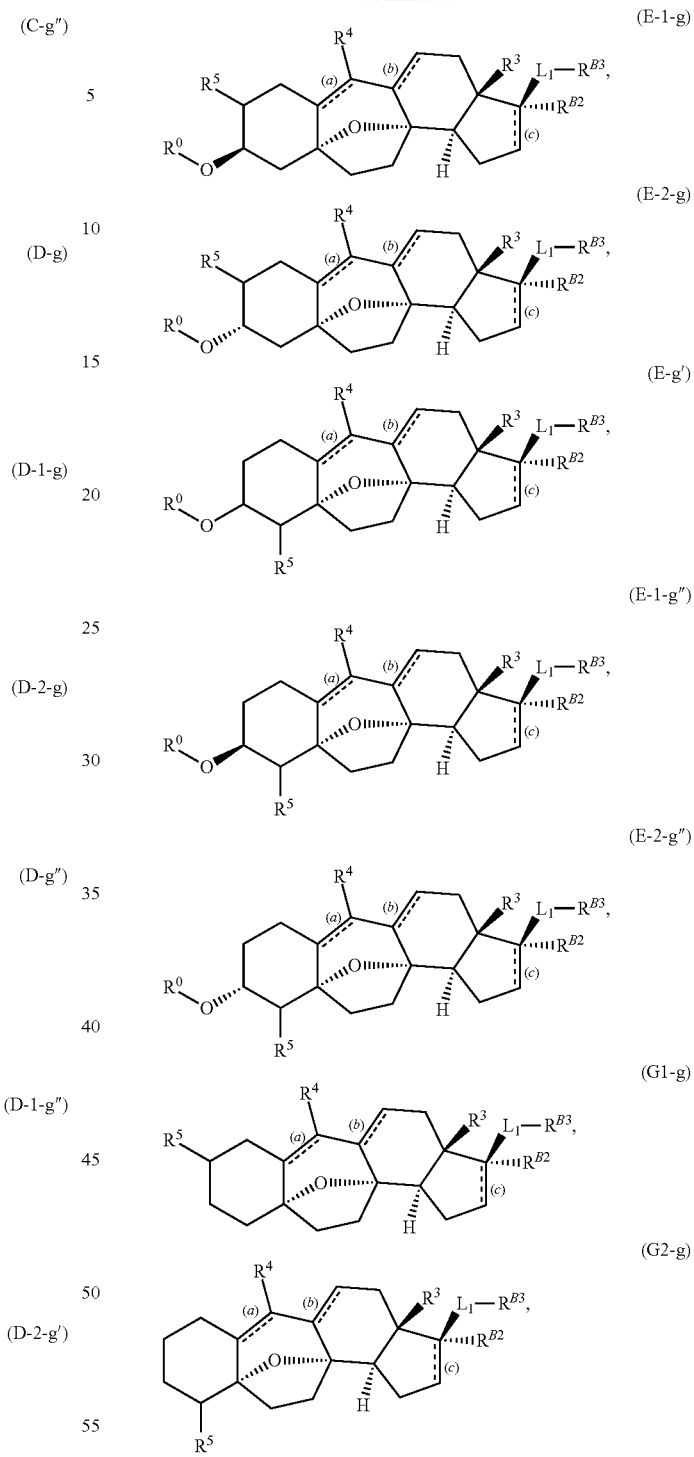

or a pharmaceutically acceptable salt, quaternary amine salt, or N-oxide thereof; wherein ----, $R^1$, $R^2$, $R^O$, $R^3$, $R^4$, $R^5$, $R^{B2}$, $L_1$, and $R^{B3}$ are as defined herein.

In certain embodiments, $L_1$ is a bond, and $R^{B3}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $L_1$ is —C(=O)—, —C(=O)O—, —C(=O)S—, —C(=O)N($R^L$)— or —N($R^L$)—(C $(R^{LL})_2)_p$—, wherein $R^L$ is hydrogen, optionally substituted alkyl, or a nitrogen protecting group, each instance of $R^{LL}$ is independently hydrogen, halogen, or optionally substituted alkyl, and $R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $L_1$ is —C(=O)—. In certain embodiments, $L_1$ is —C(=O)O—. In certain embodiments, $L_1$ is —C(=O)S—. In certain embodiments, $L_1$ is —C(=O)N($R^L$)—. In certain embodiments, $L_1$ is —N($R^L$)—C($R^{LL}$)$_2$—. In certain embodiments, $R^L$ is hydrogen or optionally substituted alkyl, e.g., methyl. In certain embodiments, each instance of $R^{LL}$ is independently hydrogen, optionally substituted alkyl, e.g., methyl, or fluoro. In certain embodiments, p is 0. In certain embodiments, p is 1. In certain embodiments, p is 2.

In certain embodiments, when $L_1$ is —C(=O)—, —C(=O)O—, —C(=O)S—, —C(=O)N($R^L$)—, or —N($R^L$)—(C($R^{LL}$)$_2$)$_p$—, and $R^{B3}$ is hydrogen, provided is a group of formula —C(=O)H, —C(=O)OH, —C(=O)SH, —C(=O)N($R^L$)H, or —N($R^L$)H.

However, in certain embodiments when $L_1$ is a bond or —C(=O)—, —C(=O)O—, —C(=O)S—, —C(=O)N($R^L$)—, or —N($R^L$)—(C($R^{LL}$)$_2$)$_p$—, $R^{B3}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^{B3}$ is an acyclic group, e.g., $R^{B3}$ is an optionally substituted alkyl, optionally substituted alkenyl, or optionally substituted alkynyl. In certain embodiments, $R^{B3}$ is optionally substituted alkyl, e.g., optionally substituted $C_{1-6}$alkyl. In certain embodiments, $R^{B3}$ is optionally substituted alkenyl, e.g., optionally substituted $C_{2-6}$alkenyl. In certain embodiments, $R^{B3}$ is optionally substituted alkynyl, e.g., optionally substituted $C_{2-6}$alkynyl.

However, in certain embodiments, $R^{B3}$ is a cyclic group, e.g., $R^{B3}$ is optionally substituted carbocyclyl, optionally substituted heterocyclyl, optionally substituted aryl, or optionally substituted heteroaryl. In certain embodiments, $R^{B3}$ is a nonaromatic cyclic group, e.g., in certain embodiments, $R^{B3}$ is optionally substituted carbocyclyl or optionally substituted heterocyclyl. In certain embodiments, $R^{B3}$ is an aromatic cyclic group, e.g., in certain embodiments, $R^{B3}$ is optionally substituted aryl or optionally substituted heteroaryl.

In certain embodiments, $R^{B3}$ is optionally substituted carbocyclyl, e.g., optionally substituted $C_{3-6}$carbocyclyl. In certain embodiments $R^{B3}$ is optionally substituted $C_3$ carbocyclyl, optionally substituted $C_4$ carbocyclyl, optionally substituted $C_5$ carbocyclyl, or optionally substituted $C_6$ carbocyclyl. In certain embodiments, $R^{B3}$ is optionally substituted cyclopenyl ($C_5$) or optionally substituted cyclohexyl ($C_6$).

In certain embodiments, $R^{B3}$ is optionally substituted carbocyclyl fused to an optionally substituted aryl or optionally substituted heteroaryl ring, wherein the point of attachment is on the carbocyclyl ring. In certain embodiments, $R^{B3}$ is optionally substituted carbocyclyl, e.g., optionally substituted $C_{3-6}$carbocyclyl, fused to an optionally substituted aryl or optionally substituted heteroaryl ring. In certain embodiments $R^{B3}$ is optionally substituted $C_3$ carbocyclyl, optionally substituted $C_4$ carbocyclyl, optionally substituted $C_5$ carbocyclyl, or optionally substituted $C_6$ carbocyclyl, fused to an optionally substituted aryl or optionally substituted heteroaryl ring. In certain embodiments, $R^{B3}$ is optionally substituted cyclopenyl ($C_5$) or optionally substituted cyclohexyl ($C_6$) fused to an optionally substituted aryl or optionally substituted heteroaryl ring. In certain embodiments, the fused aryl ring is an optionally substituted phenyl ring. In certain embodiments, the fused heteroaryl ring is an optionally substituted 6-membered heteroaryl ring, e.g., an optionally substituted pyridinyl ring.

In certain embodiments, $R^{B3}$ is optionally substituted heterocyclyl, e.g., optionally substituted 3-6 membered heterocyclyl. In certain embodiments $R^{B3}$ is optionally substituted 3-membered heterocyclyl, optionally substituted 4-membered heterocyclyl, optionally substituted 5-membered heterocyclyl, or optionally substituted 6-membered heterocyclyl, e.g., comprising 1 or 2 heteroatoms selected from oxygen, sulfur, or nitrogen.

In certain embodiments, $R^{B3}$ is optionally substituted heterocyclyl fused to an optionally substituted aryl or optionally substituted heteroaryl ring, wherein the point of attachment is on the heterocyclyl ring. In certain embodiments, $R^{B3}$ is optionally substituted heterocyclyl, e.g., optionally substituted 3-6 membered heterocyclyl, fused to an optionally substituted aryl or optionally substituted heteroaryl ring. In certain embodiments $R^{B3}$ is optionally substituted 3-membered heterocyclyl, optionally substituted 4-membered heterocyclyl, optionally substituted 5-membered heterocyclyl, or optionally substituted 6-membered heterocyclyl, e.g., comprising 1 or 2 heteroatoms selected from oxygen, sulfur, or nitrogen, fused to an optionally substituted aryl or optionally substituted heteroaryl ring. In certain embodiments, the fused aryl ring is a fused optionally substituted phenyl ring. In certain embodiments, the fused heteroaryl ring is a 6-membered heteroaryl ring, e.g., an optionally substituted pyridinyl ring. In certain embodiments, the point of attachment of $R^{B3}$ is via a nitrogen atom. In certain embodiments, $R^{B3}$ is an optionally substituted 1,2,3,4-tetrahydro-2,7-naphthyridinyl ring, a 3,4-dihydropyrido[4,3-d]pyrimidinyl ring, a 3,4-dihydropyrido[4,3-d]pyrimidin-2-one ring, or a 3,4-dihydro-2H-pyrido[3,4-e][1,3]oxazin-2-one ring, wherein the point of attachment is on the non-aromatic heterocyclyl ring.

In certain embodiments, $R^{B3}$ is optionally substituted aryl, e.g., optionally substituted $C_{6-14}$aryl. In certain embodiments, $R^{B3}$ is optionally substituted phenyl. In certain embodiments, $R^{B3}$ is optionally substituted naphthyl. In certain embodiments, $R^{B3}$ is optionally substituted phenyl fused to an optionally substituted heterocyclyl ring; such as an optionally substituted tetrahydroisoquinolinyl. It is understood in reference to optionally substituted aryl ring systems comprising a fused heterocyclyl ring that the point of attachment to the parent molecule is on the aryl (e.g., phenyl) ring.

In certain embodiments, $R^{B3}$ is optionally substituted heteroaryl, e.g., optionally substituted 5-14 membered heteroaryl. In certain embodiments, $R^{B3}$ is an optionally substituted 5-membered heteroaryl or an optionally substituted 6-membered heteroaryl. In certain embodiments, $R^{B3}$ is an optionally substituted bicyclic heteroaryl, e.g., an optionally substituted 5,6-bicyclic heteroaryl, or optionally substituted 6,6-bicyclic heteroaryl. In certain embodiments, $R^{B3}$ is an optionally substituted 5,6-bicyclic heteroaryl or optionally substituted 6,6-bicyclic heteroaryl ring system selected from the group consisting of optionally substituted naphthyridinyl, optionally substituted pteridinyl, optionally substituted quinolinyl, optionally substituted isoquinolinyl, optionally substituted cinnolinyl, optionally substituted quinoxalinyl, optionally substituted phthalazinyl, and optionally substituted quinazolinyl. In certain embodiments, the point of attachment of $R^{B3}$ is via a nitrogen atom.

In certain embodiments, wherein $R^{B3}$ is an optionally substituted heterocyclyl, $-L_1-R^{B3}$ is selected from the group consisting of:

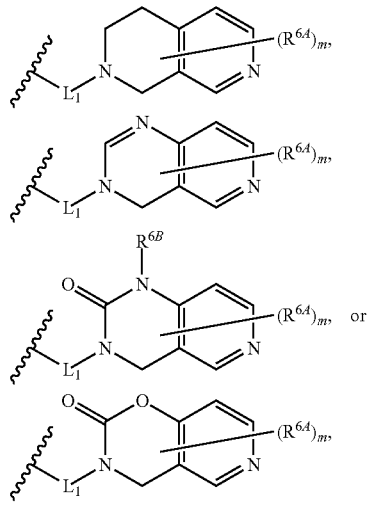

wherein:
each instance of $R^{6A}$ is independently halogen, $-NO_2$, $-CN$, $-OR^{6C}$, $-SR^{6C}$, $-N(R^{6C})_2$, $-C(=O)R^{6C}$, $-C(=O)OR^{6C}$, $-C(=O)N(R^{6C})_2$, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{6B}$ is independently hydrogen, optionally substituted alkyl, or a nitrogen protecting group when attached to nitrogen;

wherein each instance of $R^{6C}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a nitrogen protecting group when attached to nitrogen, optionally when attached to N the two $R^{6C}$ groups may be joined to form an optionally substituted heterocyclyl or optionally substituted heteroaryl ring; and m is 0 or an integer between 1 and 4, inclusive, provided $L^1$ is not $-N(R^L)-(C(R^{LL})_2)_p-$ wherein p is 0.

In certain embodiments, wherein $R^{B3}$ is an optionally substituted aryl or optionally substituted heteroaryl, $-L_1-R^{B3}$ is selected from the group consisting of:

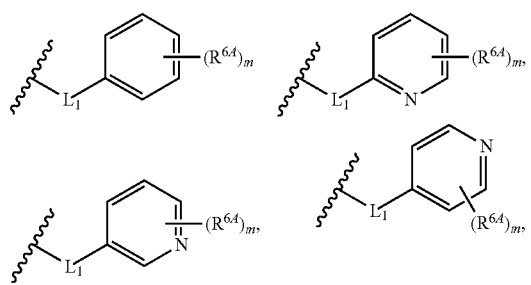

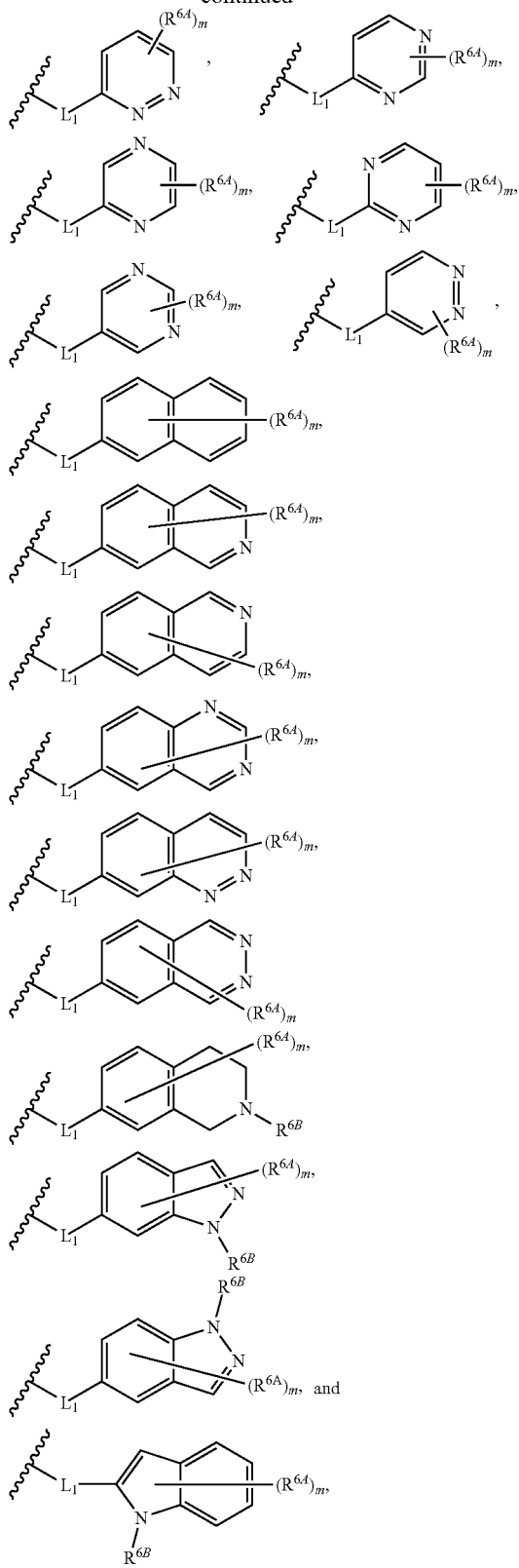

wherein:
each instance of $R^{6A}$ is independently halogen, $-NO_2$, $-CN$, $-OR^{6C}$, $-SR^{6C}$, $-N(R^{6C})_2$, $-C(=O)R^{6C}$, $-C(=O)OR^{6C}$, $-C(=O)N(R^{6C})_2$, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{6B}$ is independently hydrogen, optionally substituted alkyl, or a nitrogen protecting group when attached to nitrogen;

wherein each instance of $R^{6C}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a nitrogen protecting group when attached to nitrogen, optionally when attached to N the two $R^{6C}$ groups may be joined to form an optionally substituted heterocyclyl or optionally substituted heteroaryl ring; and m is 0 or an integer between 1 and 4, inclusive.

In certain embodiments, m is 0. In certain embodiments, m is 1, 2, 3, or 4. In certain embodiments, wherein m is 1, 2, 3, or 4, at least one $R^{6A}$ is halogen (e.g., fluoro), —$OR^{6C}$, —$SR^{6C}$, or —$N(R^{6C})_2$.

In certain embodiments, $L_1$ is a bond or —C(=O)N($R^L$)—, wherein $R^L$ is hydrogen or an optionally substituted alkyl (e.g., methyl), and $R^{B3}$ is optionally substituted aryl or optionally substituted heteroaryl, as described herein.

For example, in certain embodiments of Formula (A'), (B'), (C'), (D'), (E'), (A"), (B"), (C"), (D"), (E"), (G1), and (G2), wherein the group —$L_1$—$R^{B3}$ is a group of formula:

wherein $L_1$ is a bond, provided are compounds of Formula:

(A-h)

(A-1-h)

(A-2-h)

(A-h')

(A-1-h')

(A-2-h')

(B-h)

(B-h')

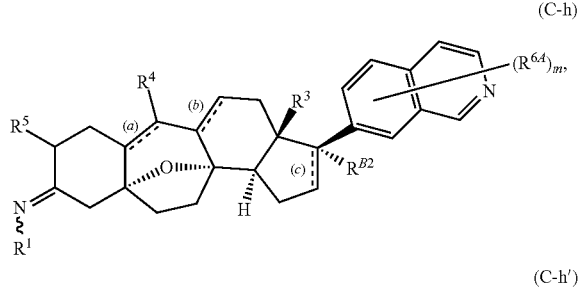
(C-h)
(C-h′)
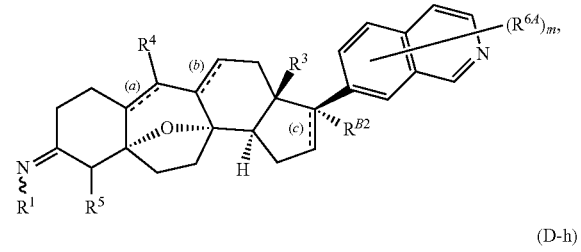
(D-h)
(D-1-h)
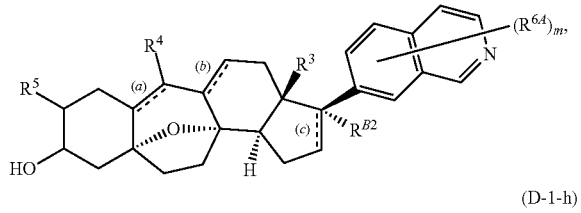
(D-2-h)
(D-h′)
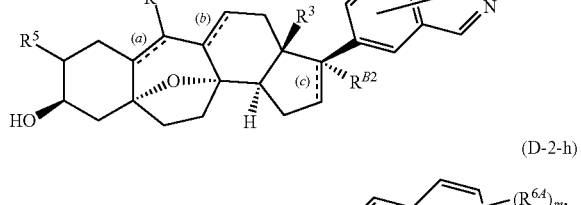
(D-1-h′)
(D-2-h′)
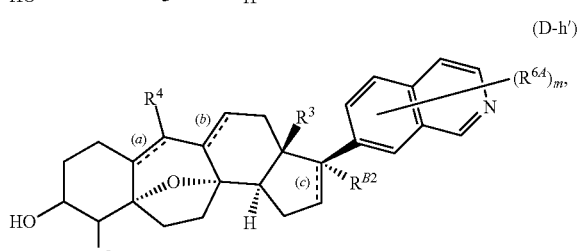
(E-h)
(E-1-h)
(E-2-h)
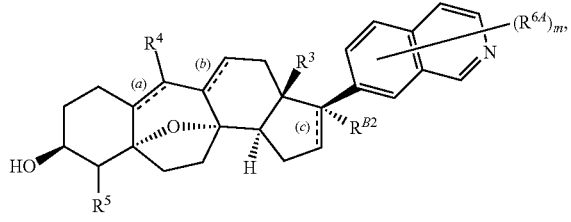
(E-h′)
(E-1-h′)
(E-2-h′)

(G1-h)

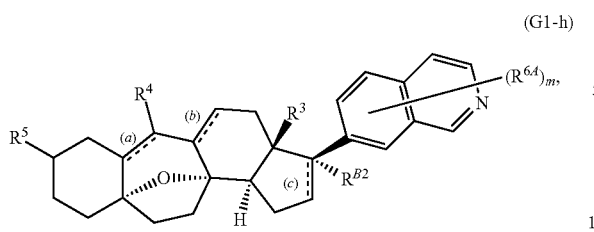

(G2-h)

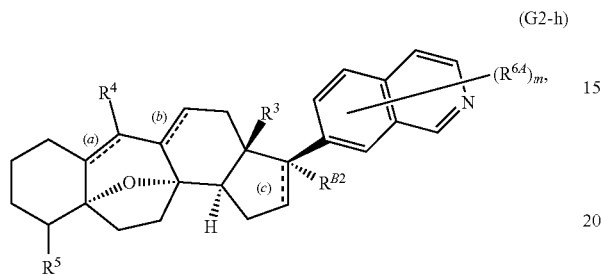

or a pharmaceutically acceptable salt, quaternary amine salt, or N-oxide thereof; wherein ----, $R^1$, $R^2$, $R^3$, $R^4$, $R^5$, $R^{6A}$, and m are as defined herein.

Alternatively, in certain embodiments, at least one instance of $R^{B1}$ and $R^{B2}$ is —$X^AR^A$. In this instance, in certain embodiments, the other of $R^{B1}$ and $R^{B2}$ is hydrogen or —$X^AR^A$ (e.g., —$OR^A$). For example, in certain embodiments, when ---- designated as (c) represents a single bond, then $R^{B1}$ is —$X^AR^A$ (e.g., —$OR^A$) and $R^{B2}$ is hydrogen or —$X^AR^A$ (e.g., —$OR^A$). In other embodiments, when ---- designated as (c) represents a single bond, then $R^{B2}$ is —$X^AR^A$ (e.g., —$OR^A$) and $R^{B1}$ is hydrogen or —$X^AR^A$ (e.g., —$OR^A$). Alternatively, in certain embodiments, when ---- designated as (c) represents a double bond, then $R^{B1}$ is —$X^AR^A$ (e.g., —$OR^A$ wherein $R^A$ is not hydrogen) and $R^{B2}$ is absent.

In certain embodiments, both instances of $R^{B1}$ and $R^{B2}$ are —$X^AR^A$. In this embodiments, in certain instances, the two $R^A$ groups may be joined to form an optionally substituted heterocyclyl ring, e.g., an optionally substituted 5-6 membered heterocyclyl ring. For example, in certain embodiments provided are compounds of Formula:

(A-k)

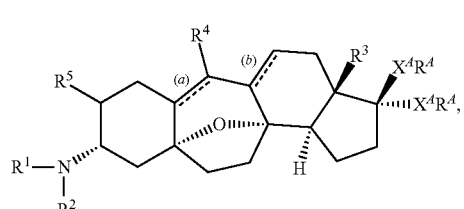

(A-1-k)

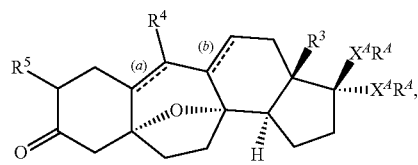

(A-2-k)

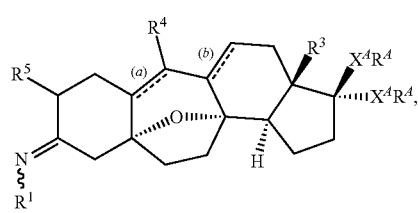

(B-k)

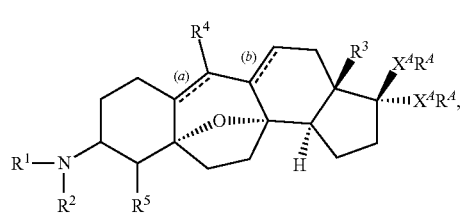

(C-k)

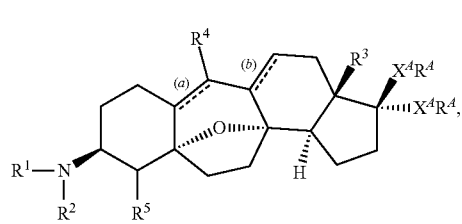

(A-k')

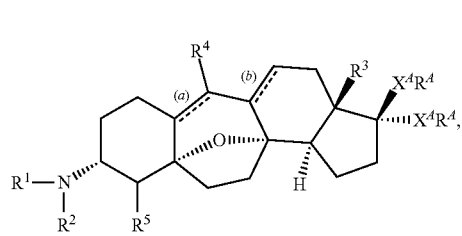

(A-1-k')

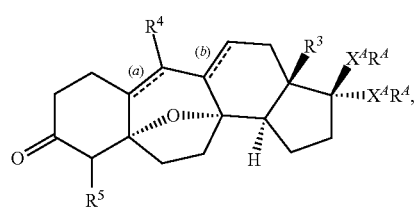

(A-2-k')

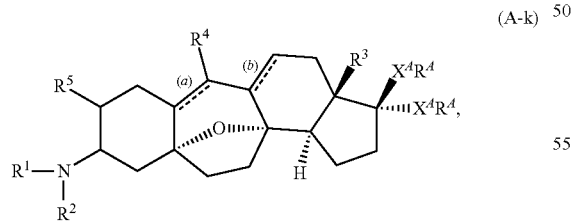

(B-k')

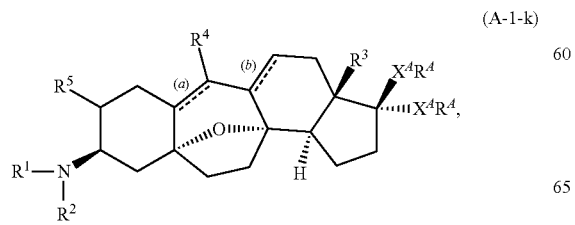

(C-k')
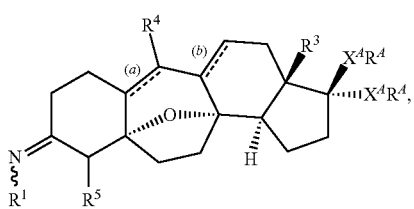
(G1-k)
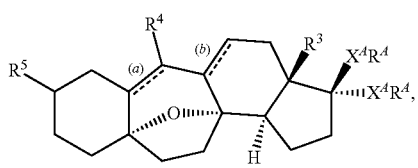
(G2-k)
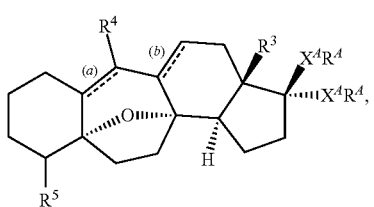
or a pharmaceutically acceptable salt, quaternary amine salt, or N-oxide thereof; wherein ⋯, $R^1$, $R^2$, $R^3$, $R^4$, $R^5$, $X^A$ and $R^A$, are as defined herein.
In certain embodiments, $R^{B1}$ and $R^{B2}$ are joined to form an oxo group (=O). For example, $R^{B1}$ and $R^{B2}$ are joined to form an oxo group (=O), provided are compounds of Formula:
(A-m)
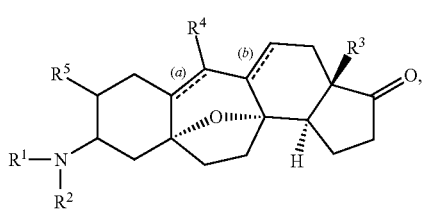
(A-1-m)
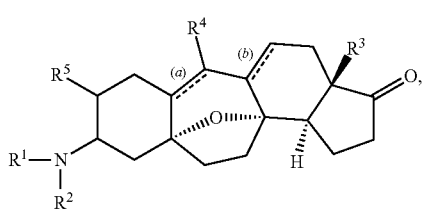
(A-2-m)
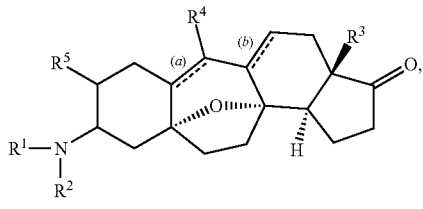
(B-m)
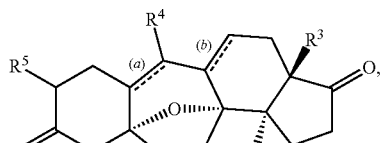
(C-m)
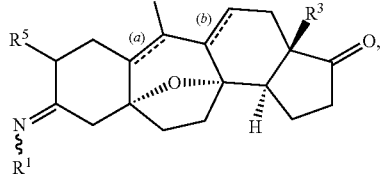
(A-m')
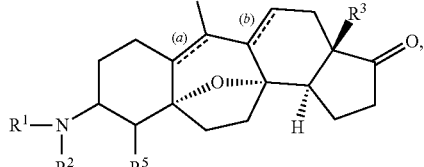
(A-1-m')
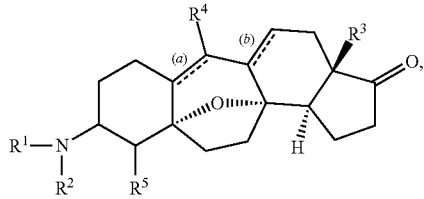
(A-2-m')
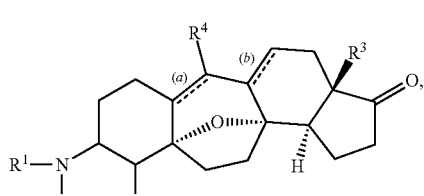
(B-m')
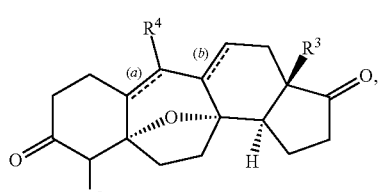
(C-m')
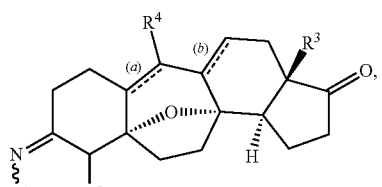
(G1-m)
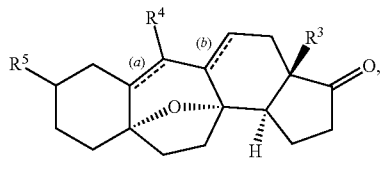

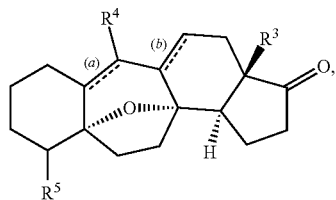
(G2-m)

or a pharmaceutically acceptable salt, quaternary amine salt, or N-oxide thereof: wherein ---, $R^1$, $R^2$, $R^3$, $R^4$, and $R^5$, are as defined herein.

Exemplary Compounds

Various combinations of certain embodiments are further contemplated herein.

For example, in certain embodiments, provided is a compound of Formulae:

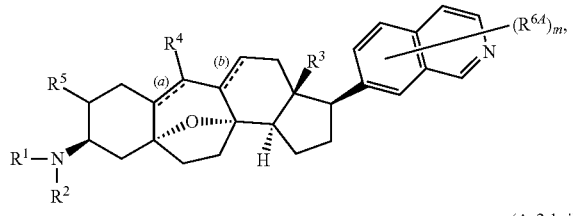
(A-1-h-i)

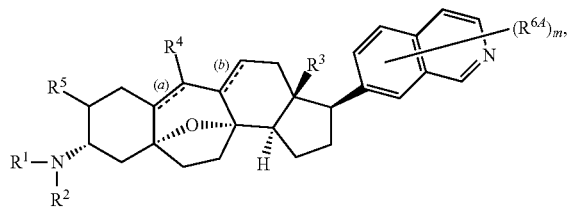
(A-2-h-i)

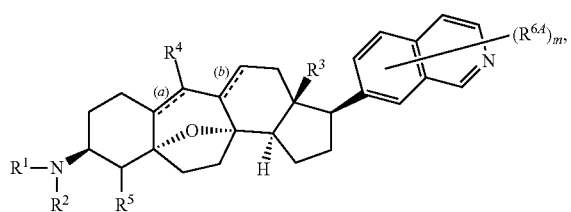
(a-1-h-i′)

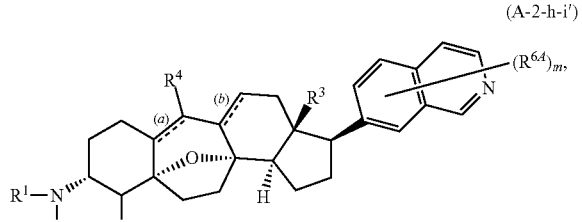
(A-2-h-i′)

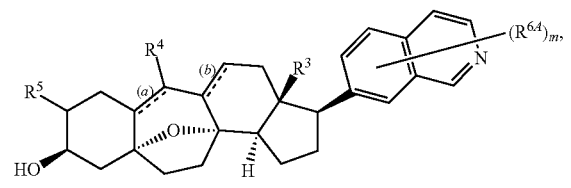
(D-1-h-i)

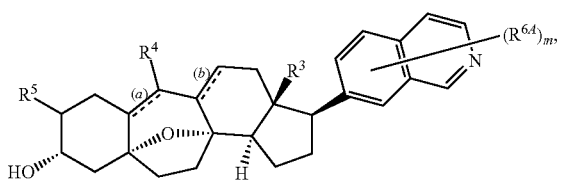
(D-2-h-i)

(D-1-h-i′)

(D-2-h-i′)

(E-1-h-i)

(E-2-h-i)

(E-1-h-i′)

(E-2-h-i′)

(G1-h-i)

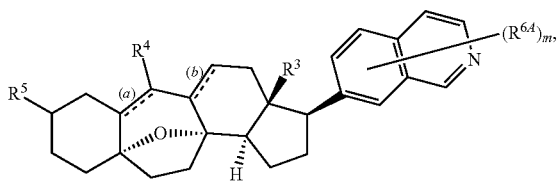

(G2-h-i)

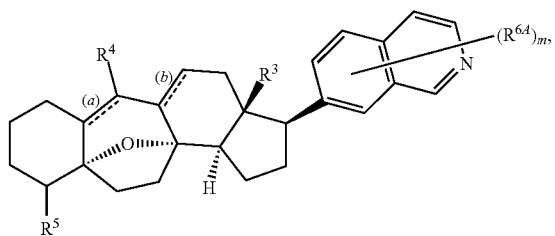

or a pharmaceutically acceptable salt, quaternary amine salt, or N-oxide thereof; wherein ---, $R^1$, $R^2$, $R^O$, $R^3$, $R^4$, $R^5$, $R^{6A}$, $R^{6B}$, $R^L$, $R^{LL}$, and m are as defined herein. In certain embodiments, $R^3$ is methyl. In certain embodiments, $R^4$ is hydrogen. In certain embodiment the bonds --- designated as (a) and (b) are double bonds. In certain embodiments, each instance of $R^1$ and $R^2$ is optionally substituted alkyl, e.g., —CH$_3$. In certain embodiments, at least one of $R^1$ and $R^2$ is a group of formula

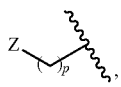

wherein p and Z are as defined herein. In certain embodiments, at least one of $R^1$ and $R^2$ is —S(=O)$_2$R$^A$. In certain embodiments, $R^1$ and $R^2$ are joined to form an optionally substituted heterocyclyl. In certain embodiments, $R^1$ and $R^2$ are joined to form a ring of formula:

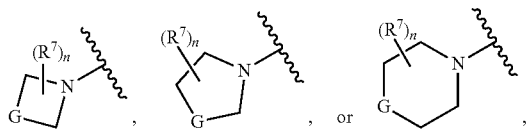

wherein $R^7$, n and G are as defined herein. In certain embodiments, the compound is an N-oxide, e.g., the group

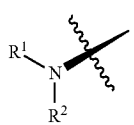

is of formula

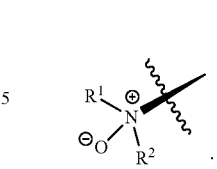

In certain embodiments, $R^O$ is an optionally substituted alkyl, e.g., —CH$_3$ or a group of formula

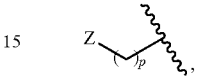

wherein Z and p are as defined herein. In certain embodiments, $R^O$ is —C(=O)R$^A$, —C(=O)OR$^A$, or —C(=O)N(R$^A$)$_2$, e.g., —C(=O)CH$_3$, —C(=O)OCH$_3$, —C(=O)N(CH$_3$)$_2$, or —C(=O)NHCH$_3$. In certain embodiments, $R^5$ is —OR$^A$. In certain embodiments, $R^5$ is —N(R$^A$)$_2$. In certain embodiments, $R^5$ is —C(R$^A$)$_3$.

In certain embodiments provided is a compound of Formulae:

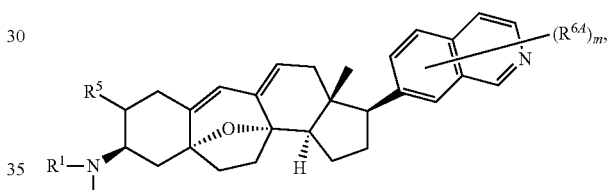

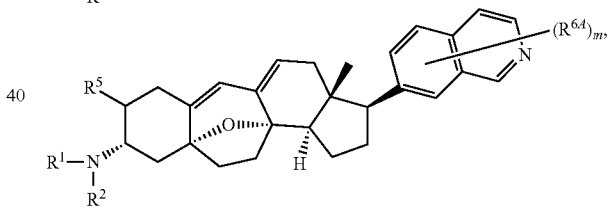

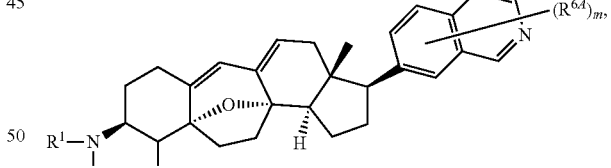

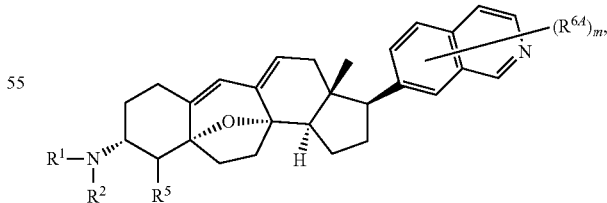

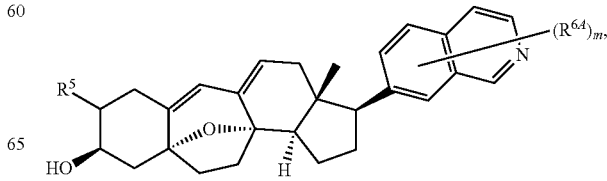

-continued

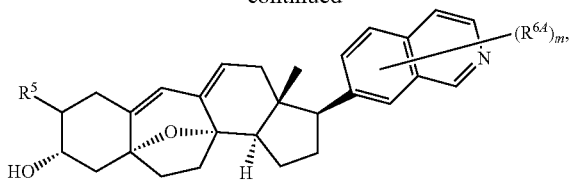

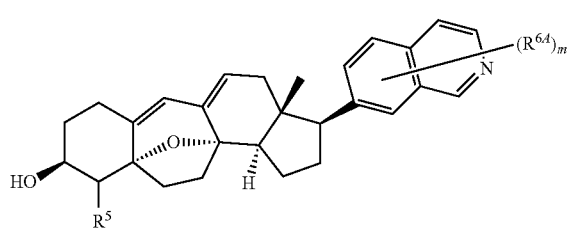

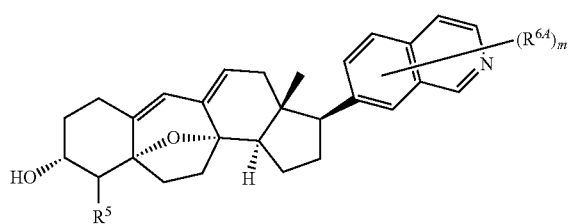

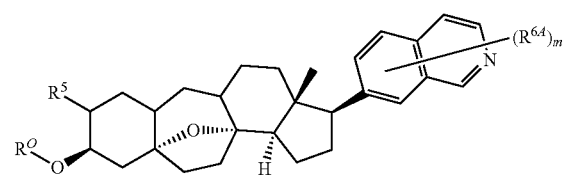

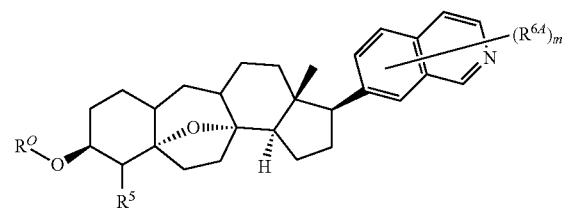

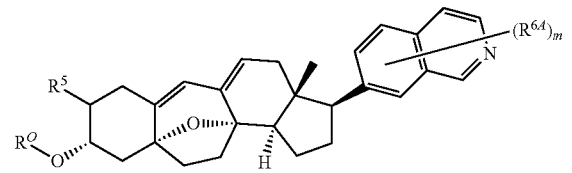

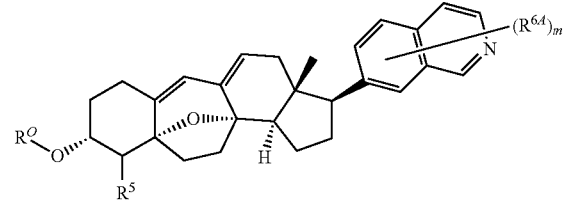

(G1-h-ii)

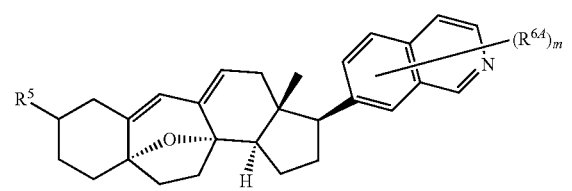

-continued (G2-h-ii)

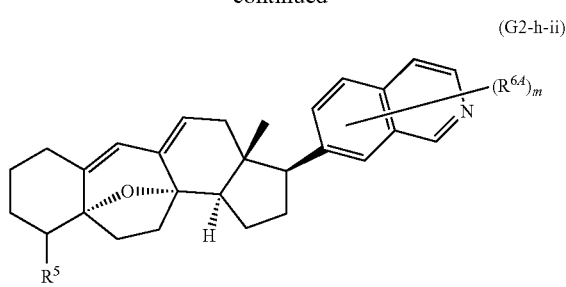

or a pharmaceutically acceptable salt, quaternary amine salt, or N-oxide thereof, wherein $R^1$, $R^2$, $R^O$, $R^{6A}$, $R^{6A}$, $R^{6B}$, $R^L$, $R^{LL}$ and m are as defined herein. In certain embodiments, each instance of $R^1$ and $R^2$ is optionally substituted alkyl, e.g., —$CH_3$. In certain embodiments, one of $R^1$ and $R^2$ is hydrogen, and one of $R^1$ and $R^2$ is optionally substituted alkyl, e.g., —$CH_3$. In certain embodiments, at least one of $R^1$ and $R^2$ is a group of formula

wherein p and Z are as defined herein. In certain embodiments, at least one of $R^1$ and $R^2$ is —$S(=O)_2R^A$. In certain embodiments, $R^1$ and $R^2$ are joined to form an optionally substituted heterocyclyl. In certain embodiments, $R^1$ and $R^2$ are joined to form a ring of formula:

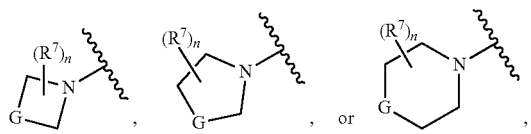

wherein $R^7$, n and G are as defined herein. In certain embodiments, the compound is an N-oxide, e.g., the group

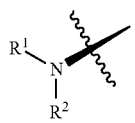

is of formula

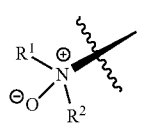

In certain embodiments, $R^O$ is an optionally substituted alkyl, e.g., —$CH_3$ or a group of formula

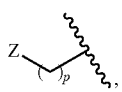

wherein Z and p are as defined herein. In certain embodiments, $R^O$ is —C(=O)$R^A$, —C(=O)O$R^A$, or —C(=O)N($R^A$)$_2$, e.g., —C(=O)CH$_3$, —C(=O)OCH$_3$, —C(=O)N(CH$_3$)$_2$, or —C(=O)NHCH$_3$. In certain embodiments, $R^5$ is —O$R^A$. In certain embodiments, $R^5$ is —N($R^A$)$_2$. In certain embodiments, $R^5$ is —C($R^A$)$_3$.

In certain embodiments provided is a compound of Formula:

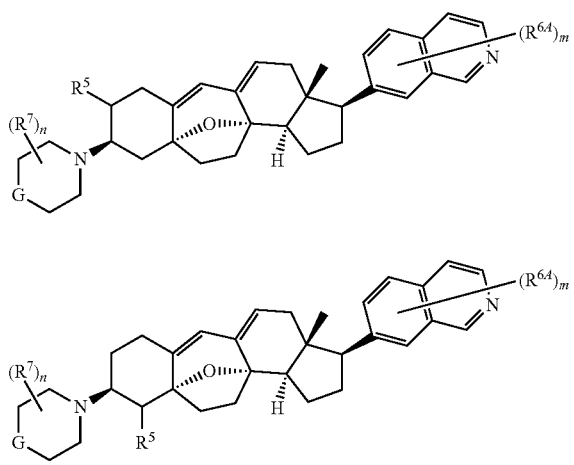

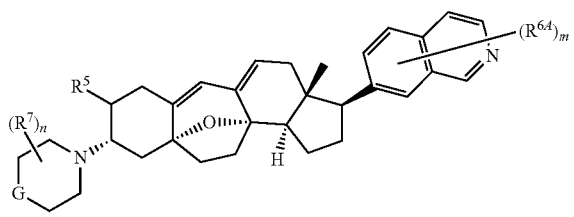

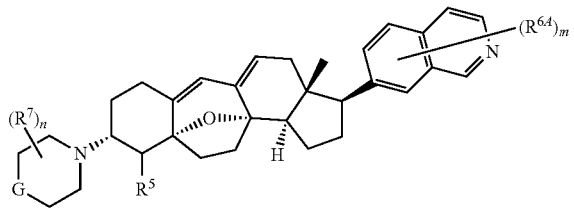

or a pharmaceutically acceptable salt, quaternary amine salt, or N-oxide thereof; wherein $R^7$, $R^{6A}$, n and m are as defined herein. In certain embodiments, G is O. In certain embodiments, G is N—CH$_3$. In certain embodiments, m is 0. In certain embodiments, m is 1. In certain embodiments, n is 0. In certain embodiments, n is 1. In certain embodiments, $R^5$ is —O$R^A$. In certain embodiments, $R^5$ is —N($R^A$)$_2$. In certain embodiments, $R^5$ is —C($R^A$)$_3$.

In certain embodiments provided is a compound of formula:

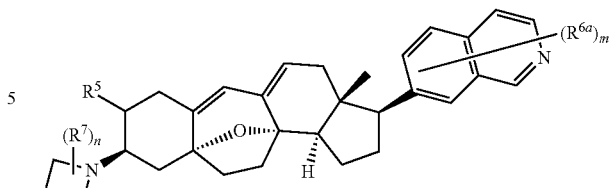

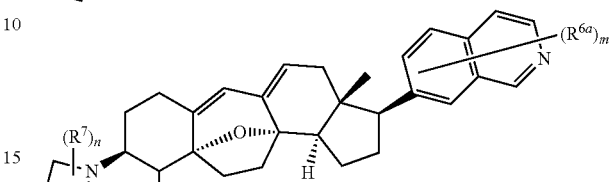

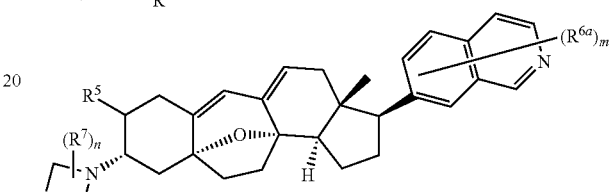

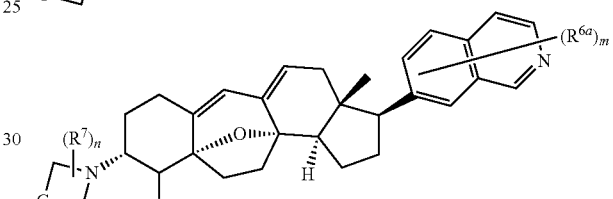

or a pharmaceutically acceptable salt, quaternary amine salt, or N-oxide thereof; wherein $R^7$, $R^{6A}$, n and m are as defined herein. In certain embodiments, G is —CH$_2$—. In certain embodiments, m is 0. In certain embodiments, m is 1. In certain embodiments, n is 0. In certain embodiments, n is 1. In certain embodiments, $R^5$ is —O$R^A$. In certain embodiments, $R^5$ is —N($R^A$)$_2$. In certain embodiments, $R^5$ is —C($R^A$)$_3$.

In certain embodiments provided is a compound of formula:

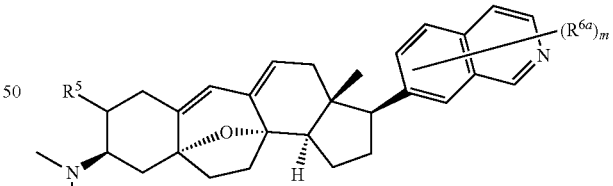

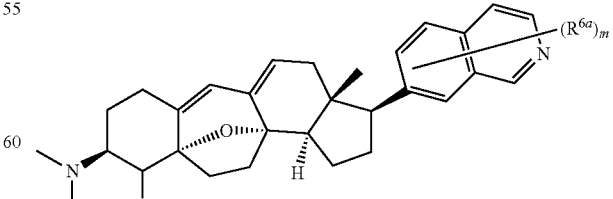

or a pharmaceutically acceptable salt, quaternary amine salt, or N-oxide thereof; wherein $R^{6A}$ and m are as defined herein. In certain embodiments, m is 0. In certain embodiments, m is 1. In certain embodiments, $R^5$ is —$OR^A$. In certain embodiments, $R^5$ is —$N(R^A)_2$. In certain embodiments, $R^5$ is —$C(R^A)_3$.

In certain embodiments provided is a compound of formula:

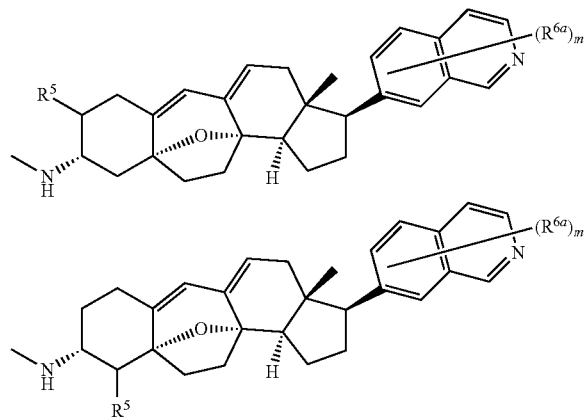

or a pharmaceutically acceptable salt, quaternary amine salt, or N-oxide thereof; wherein $R^{6A}$, and m are as defined herein. In certain embodiments, m is 0. In certain embodiments, m is 1. In certain embodiments, $R^5$ is —$OR^A$. In certain embodiments, $R^5$ is —$N(R^A)_2$. In certain embodiments, $R^5$ is —$C(R^A)_3$.

Pharmaceutical Compositions

In certain embodiments, the present invention provides pharmaceutical compositions comprising a compound of Formula (A'), (B'), (C'), (D'), (E'), (A"), (B"), (C"), (D"), (E"), (G1), or (G2) or a pharmaceutically acceptable salt, quaternary amine salt, or N-oxide thereof, and a pharmaceutically acceptable excipient. In certain embodiments, the compound is present in an effective amount, e.g., a therapeutically effective amount or a prophylactically effective amount.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of Formula (A'), (B'), (C'), (D'), (E'), (A"), (B"), (C"), (D"), (E"), (G1), or (G2) or a pharmaceutically acceptable salt, quaternary amine salt, or N-oxide thereof (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient. In some embodiments, the composition comprises between 0.1% and 1%, between 1% and 10%, between 10% and 20%, between 20% and 30%, between 30% and 40%, between 40% and 50%, between 50% and 60%, between 60% and 70%, between 70% and 80%, between 80% and 90%, or between 90% and 100% (w/w) of active ingredient. In the absence of a statement to the contrary, the composition comprises between 0.1 and 100% (w/w) of active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g.

polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredient(s), the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds are mixed with solubilizing agents such as Cremophor, alcohols, oils, modified oils, glycols, polysorbates, cyclodextrins, polymers, polymer conjugates (e.g., IT-101/CLRX101), and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the active ingredient, it is often desirable to slow the absorption of the active ingredient from subcutaneous or intramuscular injection. This can be accomplished by the use of a liquid suspension of crystalline or amorphous material with poor water solubility. The rate of absorption of the active ingredient then depends upon its rate of dissolution which, in turn, may depend upon crystal size and crystalline form. Alternatively, delayed absorption of a parenterally administered form is accomplished by dissolving or suspending the active ingredient in an oil vehicle.

Compositions for rectal or vaginal administration are typically suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient(s) can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. In some embodiments, the formulation suitable for nasal administration comprises between 0.1% and 1%, between 1% and 10%, between 10% and 20%, between 20% and 30%, between 30% and 40%, between 40% and 50%, between 50% and 60%, between 60% and 70%, between 70% and 80%, between 80% and 90%, or between 90% and 100% (w/w) of active ingredient. In the absence of a statement to the contrary, the formulation suitable for nasal administration comprises between 0.1 and 100% (w/w) of active ingredient. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or atomized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Treatment

CDK8 and CDK19, referred to as "Mediator kinases", assemble in multi-protein complexes that reversibly bind the Mediator complex. The Mediator complex links enhancer-bound transcription factors to promoter-bound RNA pol II holoenzyme and it influences chromatin architecture to regulate transcription and gene expression through still poorly understood mechanisms. Recent comprehensive genome-wide sequencing of samples from 200 AML patients revealed that, remarkably, nearly all mutations in presumably cancer-driving proteins are associated with regulating gene expression. See, e.g., Aerts, et al., *Nature* (2013) 499:35-36; The Cancer Genome Atlas Research Network, 2013. Genomic and Epigenomic Landscapes of Adult De Novo Acute Myeloid Leukemia. *N Engl. J. Med.* 368, 2059-2074. Therefore, specific inhibition of Mediator kinases might be a new means to disrupt the ability of some AML mutations to deregulate gene expression programs that drive AML cell growth. Specific small molecule inhibition of CDK8/CDK19 may also prove beneficial for treating other cancers that rely on deregulated gene expression. CDK8/cyclin C was further observed to be more highly expressed in neurons and astrocytes of Alzheimer's disease (AD) patients, and thus specific small molecule inhibition of CDK8 may also prove beneficial for treating degenerative disorders, such as AD. See, e.g., Hessel et al., *Neurobiology of Aging* (2003) 24:427-435, wherein. Cortistatin A has been reported to bind to CDK8 and CDK19. See, e.g., Cee et al., *Angew Chem Int Ed* (2009) 48:8952 and US 20120071477. Furthermore, as described in PCT/US2014/72365, incorporated herein by reference, cortistatin A inhibits CDK8 kinase activity, in part due to this binding. CDK8 and CDK19 have very similar sequences and catalytic domains suggesting that inhibiting CDK8 will likely also inhibit CDK19. See, e.g., Ries et al., *Semin. Cell Dev. Biol.* (2011) 22:735-740. Blast alignment of CDK8 vs. CDK19 also indicate that the amino acids are 70% identical and 82% similar.

Thus, in one aspect, provided is a method of inhibiting CDK8 and/or CDK19 kinase activity in a cell comprising contacting a compound of Formula (A'), (B'), (C'), (D'), (E'), (A"), (B"), (C"), (D"), (E"), (G1), or (G2) or a pharmaceutically acceptable salt, quaternary amine, or N-oxide thereof, with the cell. In certain embodiments, the method is an in vitro method. In certain embodiments, the method is an in vivo method. In another aspect, provided is a method of treating a condition associated with CDK8 and/or CDK19 kinase activity, comprising administering to a subject in need thereof a compound Formula (A'), (B'), (C'), (D'), (E'), (A"), (B"), (C"), (D"), (E"), (G1), or (G2) or a pharmaceutically acceptable salt, quaternary amine salt, or N-oxides thereof.

In certain embodiments, the condition associated with CDK8 and/or CDK19 kinase activity is a proliferative disorder, e.g., cancer. CDK8 kinase activity has been linked to colon cancer. See, e.g., Firestein, et al., *Nature* (2008) 455:547-551.

In certain embodiments, the condition associated with CDK8 and/or CDK19 kinase activity is a diabetic condition, e.g., diabetes.

In certain embodiments, the condition associated with CDK8 and/or CDK19 kinase activity is a degenerative disorder, e.g., Alzheimer's disease (AD).

CDK8 has been linked to regulation of a number of signaling pathways and transcriptional programs that have been implicated in maintaining and driving diseases such as cancer. These pathways and programs include Wnt/beta-catenin pathway, Notch pathway, TGF-beta/BMP signaling, JAK-STAT pathway, p53 pathway, and hypoxia response. Aberrant Wnt/beta-catenin signaling is associated with leukemias and many other cancers. For instance, the most common mutations in colon cancer are ones that lead to activation of Wnt/beta-catenin signaling, expression of Wnt-target genes, and tumorigenesis. Given its central role in tumorigenesis, there is much interest in identifying safe, effective inhibitors of Wnt/beta-catenin signaling. See, e.g., Wang, et al., *Science* (2010) 327:1650-1653. Polakis, *EMBO J.* (2012) 31: 2737-2746.

Thus, in another aspect, provided is a method of treating a β-catenin pathway-associated condition comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine, or N-oxide thereof. In another aspect, provided is a method of modulating the β-catenin pathway (e.g., by inhibiting the expression of beta-catenin target genes) in a cell comprising contacting a compound of Formula (A'), (B'), (C'), (D'), (E'), (A"), (B"), (C"), (D"), (E"), (G1), or (G2) or a pharmaceutically acceptable salt, quaternary amine, or N-oxide thereof, with the cell. In certain embodiments, the method is an in vitro method. In certain embodiments, the method is an in vivo method.

As described in PCT/US2014/72365, incorporated herein by reference, cortistatin A inhibits beta-catenin activated transcription in a reporter gene assay and expression of putative Wnt/beta-catenin target genes in AML cells. Numerous studies have linked beta-catenin pathway activation to tumor initiation, maintenance, and growth. Wnt/beta-catenin pathway alterations have been observed in breast cancer, colorectal cancer, hepatocellular carcinoma, medulloblastoma, pancreatic cancer, lymphoma/leukemia, lung cancer, kidney cancer, and Wilms' tumor. See, e.g., Saito-Diaz, et al., *Growth Factors* (2013) 31:1-31. In addition to cancer, other diseases with overactivation of the Wnt/beta-catenin pathway include high bone mass diseases and hypertrophic obesity. Furthermore, variants of the Wnt-beta catenin pathway transcription factor TCF7L2 have been associated with diabetes. See, e.g., MacDonald et al., *Developmental Cell* (2009) 17, 9-26.

In another aspect, provided is a method of treating a JAK-STAT pathway-associated condition comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine, or N-oxide thereof. In another aspect, provided is a method of modulating the STAT1 activity in a cell (e.g., by inhibiting phosphorylation of STAT1 S727 in the JAK-STAT pathway, leading to up- or down-regulation of specific STAT1-associated genes) comprising contacting a compound of Formula (A'), (B'), (C'), (D'), (E'), (A"), (B"), (C"), (D"), (E"), (G1), or (G2) or a pharmaceutically acceptable salt, quaternary amine, or N-oxide thereof, with the cell. In certain embodiments, the method is an in vitro method. In certain embodiments, the method is an in vivo method.

As described in PCT/US2014/72365, incorporated herein by reference, cortistatin A inhibits interferon-gamma-stimulated STAT1 phosphorylation. Inhibition of STAT1 phosphorylation may be a therapeutic strategy to treat aberrant inflammation, including in atherosclerosis, to treat cancers, including MPNs and leukemias, and to treat diabetes, through prevention of STAT1-mediated beta-cell apoptosis. IFN-gamma is expressed at high levels in atherosclerotic lesions leading to increased inflammation through STAT1 activation and IFN-gamma activates STAT1 to induce beta-cell apoptosis. See, e.g., Gysemans et al., *Biochem. Soc. Trans* (2008) 36:328. Phosphorylation of STAT1 by CDK8 has also been shown to restrain NK activation and tumor surveillance. Therefore, inhibition of CDK8 kinase activity may beneficially enable an NK-mediated tumor cell killing in addition to directly inhibiting the proliferation of tumor cells. See, e.g., Putz et al., *Cell Reports* (2013) 4:437-444.

It has been reported that nuclear CDKs, such as CDK8, drive SMAD transcriptional activation and turnover in BMP and TGF-beta. See, e.g., Alarcon et al., *Cell* (2009) 139: 757-769. Thus, in yet another aspect, provided is a method of treating a TGF-beta/BMP pathway-associated condition comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine, or N-oxide thereof. In another aspect, provided is a method of modulating the TGF-beta/BMP pathway (e.g., by inhibiting CDK8/CDK19 phosphorylation SMAD proteins in the TGF-beta/BMP pathway leading to up- or down-regulation of specific SMAD protein-associated genes) in a cell comprising contacting a compound of Formula (A'), (B'), (C'), (D'), (E'), (A"), (B"), (C"), (D"), (E"), (G1), or (G2) or a pharmaceutically acceptable salt, quaternary amine, or N-oxide thereof, with the cell. In certain embodiments, the method is an in vitro method. In certain embodiments, the method is an in vivo method.

TGF-beta and BMP pathways are critical for tissue homeostasis, modulation of TGF-beta and BMP pathway activity may be a treatment strategy for conditions including but not limited to muscle dystrophy (see, e.g., Ceco, *FEBS J.* (2013) 280:4198-4209), immune response to transplants, cancer, fibrosis, and Marfan syndrome (see, e.g., Akhurst and Hata, Nat Rev Drug Discov (2012) 11:790-811).

Hypoxia is a condition in which the body or region of the body is deprived of adequate oxygen supply, and may result from altitude sickness, ischaemia, stroke, heart attack, anemia, cancer, and carbon monoxide poisoning. CDK8 has been linked to regulation of hypoxic response, playing a role in induction of HIF-1-A (HIF-1-alpha) target genes. These genes are involved in angiogenesis, glycolysis, metabolic adaption, and cell survival, processes critical to tumor maintenance and growth. See, e.g., Galbraith, et al., *Cell* 153:1327-1339.

Thus, in one aspect, provided is a method of treating a condition associated with hypoxia comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine, or N-oxide thereof. In another aspect, provided is a method of reducing hypoxia injury comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine, or N-oxide thereof. In yet another aspect, provided is a method of modulating HIF-1-A (HIF-1-alpha) activity (e.g., by inhibiting the expression HIF-1-alpha associated genes) in a cell comprising contacting a compound of Formula (A'), (B'), (C'), (D'), (E'), (A"), (B"), (C"), (D"), (E"), (G1), or (G2) or a pharmaceutically acceptable salt, quaternary amine, or N-oxide thereof, with the cell. In certain embodiments, the method is an in vitro method. In certain embodiments, the method is an in vivo method.

In another aspect, provided is a method of increasing BIM expression (e.g., BCLC2L11 expression) to induce apoptosis in a cell comprising contacting a compound of Formula (A'), (B'), (C'), (D'), (E'), (A"), (B"), (C"), (D"), (E"), (G1), or (G2) or a pharmaceutically acceptable salt, quaternary amine, or N-oxide thereof, with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is downregulated in many cancers and BIM is inhibited in many cancers, including chronic myelocytic leukemia (CML) and non-small cell lung cancer (NSCLC) and that suppression of BCL2L11 expression can confer resistance to tyrosine kinase inhibitors. See, e.g., Ng et al., *Nat. Med.* (2012) 18:521-528.

Furthermore, the cortistatins as a class of compounds have been found to have anti-antiogenic activity. See, e.g., Aoki, et al., *JACS* (2006) 128: 3148-9. Angiogenesis is the process of generating new capillary blood vessels from the pre-existing vasculature. After birth, angiogenesis contributes to organ growth, but in adulthood it is strictly regulated and occurs only during wound healing and in the female reproductive cycle. See, e.g., Klagsbrun et al., Molecular angiogenesis. *Chemistry & Biology* 1999, 6 (8), R217-R224. Under normal physiological conditions, angiogenesis is tightly controlled by a series of pro-angiogenic and anti-angiogenic factors, which allow vascular growth for controlled periods of time. See, e.g., Ferrara, Vascular Endothelial Growth Factor as a Target for Anticancer Therapy. *The Oncologist* 2004, 9:2-10. Persistent, unregulated angiogenesis has been implicated in a wide range of diseases, including rheumatoid arthritis, macular degeneration, atherosclerosis, obesity, benign neoplasms, and cancers. See, e.g., Moulton et al., Angiogenesis inhibitors endostatin or TNP-470 reduce intimal neovascularization and plaque growth in apolipoprotein E-deficient mice. *Circulation* 1999, 99, (13), 1726-1732; and Hanahan et al., The hallmarks of cancer. *Cell* 2000, 100, (1), 57-70. That these pathological states are unified by their status as "angiogenesis-dependent diseases" but are otherwise unrelated has led Folkman to propose the concept of angiogenesis as an "organizing principle" in biology, by which many types of seemingly dissimilar phenomena may be connected. See Folkman, Opinion-Angiogenesis: an organizing principle for drug discovery? *Nature Reviews Drug Discovery* 2007, 6(4):273-286.

Thus, in yet another aspect, provided is a method of treating a condition associated with angiogenesis, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine salt, or N-oxide thereof.

In certain embodiments, the condition associated with angiogenesis is a diabetic condition or associated complication. In certain embodiments, provided is a method of treating a diabetic condition or associated complication comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine salt, or N-oxide thereof.

As used herein, a "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type 2 diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes.

All forms of diabetes increase the risk of long-term complications (referred to herein as the "associated complication" of the diabetic condition). These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

As will be appreciated by those of ordinary skill in this art, in treating a diabetic condition or complication, an effective amount of a compound administered may, for example, reduce, prevent, or delay the onset, of any one of the following symptoms: reduce fasting plasma glucose level [typical diabetic level is ≥7.0 mmol/l (126 mg/dl); typical prediabetic range is 6.1 to 6.9 mmol/l]; reduce plasma glucose [typical diabetic level is ≥11.1 mmol/l (200 mg/dL) two hours after a 75 g oral glucose load as in a glucose tolerance test]; reduce symptoms of hyperglycemia and casual plasma glucose [typical diabetic level is ≥11.1 mmol/l (200 mg/dl)]; reduce levels of glycated hemoglobin (Hb A1C) [typical diabetic level is ≥6.5%]. Subjects with fasting glucose levels from 110 to 125 mg/dl (6.1 to 6.9 mmol/1) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

In certain embodiments, the associated complication is diabetic retinopathy. For example, in certain embodiments, provided is a method of treating diabetic retinopathy comprising administering to a subject in need thereof a compound of Formula (A'), (B'), (C'), (D'), (E'), (A"), (B"), (C"), (D"), (E"), (G1), or (G2), or a pharmaceutically acceptable salt, quaternary amine, or N-oxide thereof.

In certain embodiments, the condition associated with angiogenesis is macular degeneration. In certain embodiments, provided is a method of treating macular degeneration comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine salt, or N-oxide thereof.

In certain embodiments, the condition associated with angiogenesis is obesity. As used herein, "obesity" and "obese" as used herein, refers to class I obesity, class II obesity, class III obesity and pre-obesity (e.g., being "overweight") as defined by the World Health Organization. In certain embodiments, provided is a method of treating obesity comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine salt, or N-oxide thereof. Evidence suggests that adipose tissue expansion is dependent on vasculature development. Therefore, inhibition of angiogenesis may be therapeutic strategy for restricting the expansion of adipose tissue to prevent and treat obesity. See, e.g., Christiaens and Lijnen, *Molecular and Cellular Endocrinology* (2010) 318:2-9.

In certain embodiments, the condition associated with angiogenesis is atherosclerosis. In certain embodiments, provided is a method of treating atherosclerosis comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine salt, or N-oxide thereof. Evidence suggests that new angiogenesis occurs in atherosclerotic lesions, contributing to their growth and rupture. Therefore, inhibition of angiogenesis may be a therapeutic strategy for restricting the expansion, growth, and ultimate rupture of atherosclerotic plaques to prevent and treat atherosclerosis. See, e.g., Ho-Tin-Noé et al., *Trends Cariovasc. Med.* (2011) 21:183-187.

In certain embodiments, the condition associated with angiogenesis is a proliferative disorder. In certain embodiments, provided is a method of treating a proliferative disorder comprising administering to a subject in need thereof a compound of Formula (A'), (B'), (C'), (D'), (E'), (A"), (B"), (C"), (D"), (E"), (G1), or (G2) or a pharmaceutically acceptable salt, quaternary amine, or N-oxide thereof.

Exemplary proliferative disorders include, but are not limited to, tumors (e.g., solid tumors), begnin neoplasms, pre-malignant neoplasms (carcinoma in situ), and malignant neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain embodiments, the cancer is associated with CDK8 and/or CDK19 kinase activity. In certain embodiments, the cancer is associated with CDK8 kinase activity. In certain embodiments, the cancer is associated with CDK19 kinase activity. In certain embodiments, the cancer is associated with aberrant CDK8 kinase activity. In certain embodiments, the cancer is associated with aberrant CDK19 kinase activity. In certain embodiments, the cancer is associated with increased CDK8 kinase activity. In certain embodiments, the cancer is associated with increased CDK19 kinase activity.

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML). As described in PCT/US2014/72365, incorporated herein by reference, cortistatin A or cortistatin A analogs inhibit proliferation of AML cell lines in vitro, and cortistatin A inhibits AML progression in vivo.

In certain embodiments, the proliferative disorder is a myeloproliferative neoplasm. In certain embodiments, the myeloproliferative neoplasm (MPN) is primary myelofibrosis (PMF). As described in PCT/US2014/72365, incorporated herein by reference, cortistatin A inhibits the proliferation of cell lines derived from patients with MPNs, and cortistatin A is efficacious in an in vivo model of PMF.

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

Compounds of Formula (A'), (B'), (C'), (D'), (E'), (A"), (B"), (C"), (D"), (E"), (G1), or (G2) and pharmaceutically acceptable salts, quaternary amines, and N-oxides thereof, may be formulated in dosage unit form for ease of administration and uniformity of dosage. It will be understood, however, that the total daily usage of the compositions comprising a compound as described herein will be decided by the attending physician within the scope of sound medical judgment. The specific therapeutically effective dose level for any particular subject or organism will depend upon a variety of factors including the disease, disorder, or condition being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The compounds and compositions provided can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 0.1 mg to about 10 mg, or about 0.1 mg to about 15 mg, of a compound per unit dosage form. In certain embodiments, an effective amount of an active agent for administration to a 70 kg adult human comprises about 1 mg, about 5 mg, about 10 mg, about 15 mg, about 20 mg, about 25 mg, about 30 mg, about 40 mg, about 50 mg, about 60 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, about 850 mg, about 900 mg, about 950 mg, or about 1000 mg.

In certain embodiments, the compound may be administered orally or parenterally to an adult human at dosage levels sufficient to deliver from about 0.001 mg/kg to about 100 mg/kg, from about 0.01 mg/kg to about 50 mg/kg, preferably from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 0.01 mg/kg to about 1 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically active agent is an anti-cancer agent, e.g., radiation therapy and/or one or more chemotherapeutic agents.

Methods of Preparation

Still further provided are methods of preparing compounds of Formula (A'), (B'), (C'), (D'), (E'), (A"), (B"), (C"), (D"), (E"), (G1), or (G2). An exemplary synthesis of compounds described herein is provided in Schemes 5 to 18.

The synthesis initially is contemplated using a compound of Formula (I) as starting material. Oxidation (e.g., DDQ, $MnO_2$) of estrone (wherein $R^3$ is —$CH_3$) or norestrone (wherein $R^3$ is H) (I) provides the compound of Formula (III). See, e.g., Stephan et al., *Steroid*, 1995, 60, 809-811. The compound of Formula (III) is protected as an acetal or ketal (e.g., via reaction with $HX^AR^A$, or $HX^AR^A$—$R^AX^AH$, wherein the two $R^A$ groups are joined, wherein $R^{B1}$ and $R^{B2}$ are each independently —$X^AR^A$) to give a mixture (e.g., 1:1 mixture) of (IV)-A and (IV)-B. Exemplary conditions contemplated for protection include PTSA and ethylene glycol, PTSA and $CH(OMe)_3$, PTSA and $CH(OEt)_3$, and PTSA and 2,2-dimethyl-1,3-propandiol). The protected compounds are then alkylated (e.g., methylated) using an alkylating agent (e.g., $Me_2SO_4$ and $K_2CO_3$, EtN(i-Pr)$_2$ and TMS-diazomethane) to afford (V)-A and (V)-B, wherein E is optionally substituted alkyl. See Scheme 5.

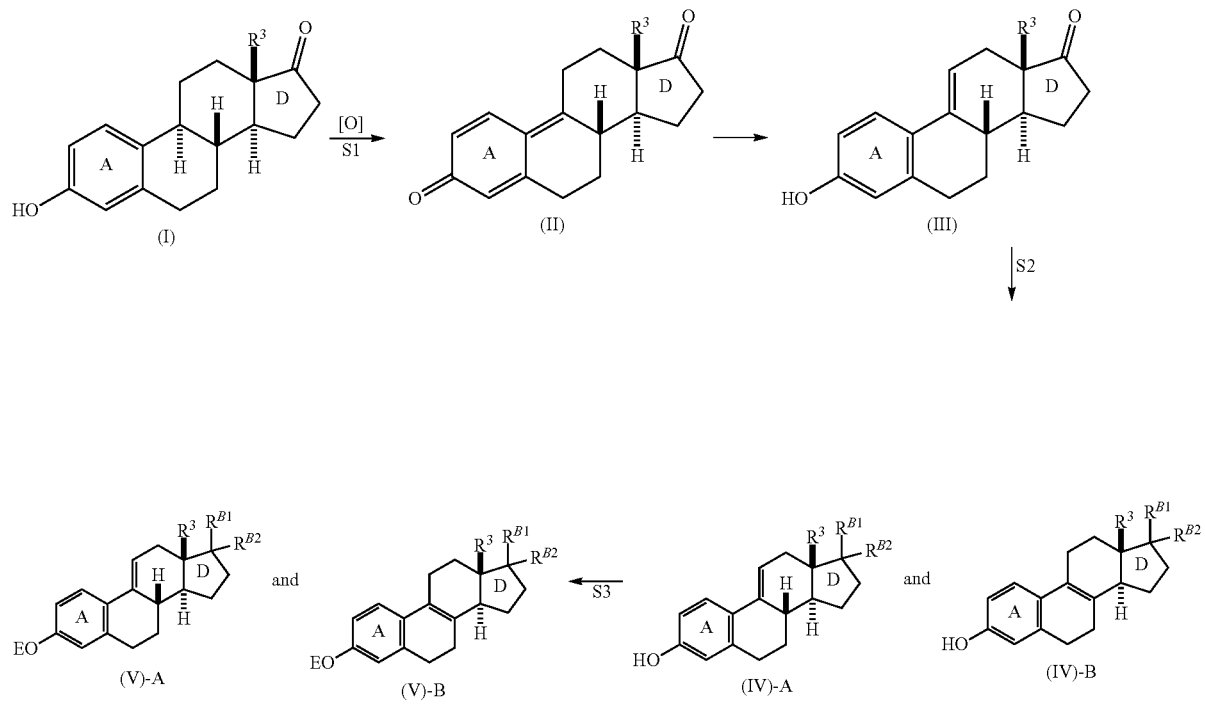

Scheme 6 provides other exemplary routes to provide a compound of Formula (IV-B), e.g., wherein $R^3$ is —$CH_3$. For example, the compound of Formula (V)-B is achieved as racemic mixtures from 6-methoxy-1-tetralone in four steps as described in Scheme 6(A). For the Grignard reaction, see, e.g., Saraber et al., *Tetrahedron*, 2006, 62, 1726-1742. For hydrogenation, see, e.g., Sugahara et al., *Tetrahedron Lett*, 1996, 37, 7403-7406. Scheme 6(B) shows method to obtain enantiopure Torgov's intermediate by chiral resolution. See, e.g., Bucourt et al., *J. Bull. Soc. Chim. Fr.* (1967) 561-563. Scheme 6(C) provides another method of preparing enantiopure Torgov's intermediate aided by enzymatic reduction. See, e.g., Gibian et al., *Tetrahedron Lett.* (1966) 7:2321-2330.

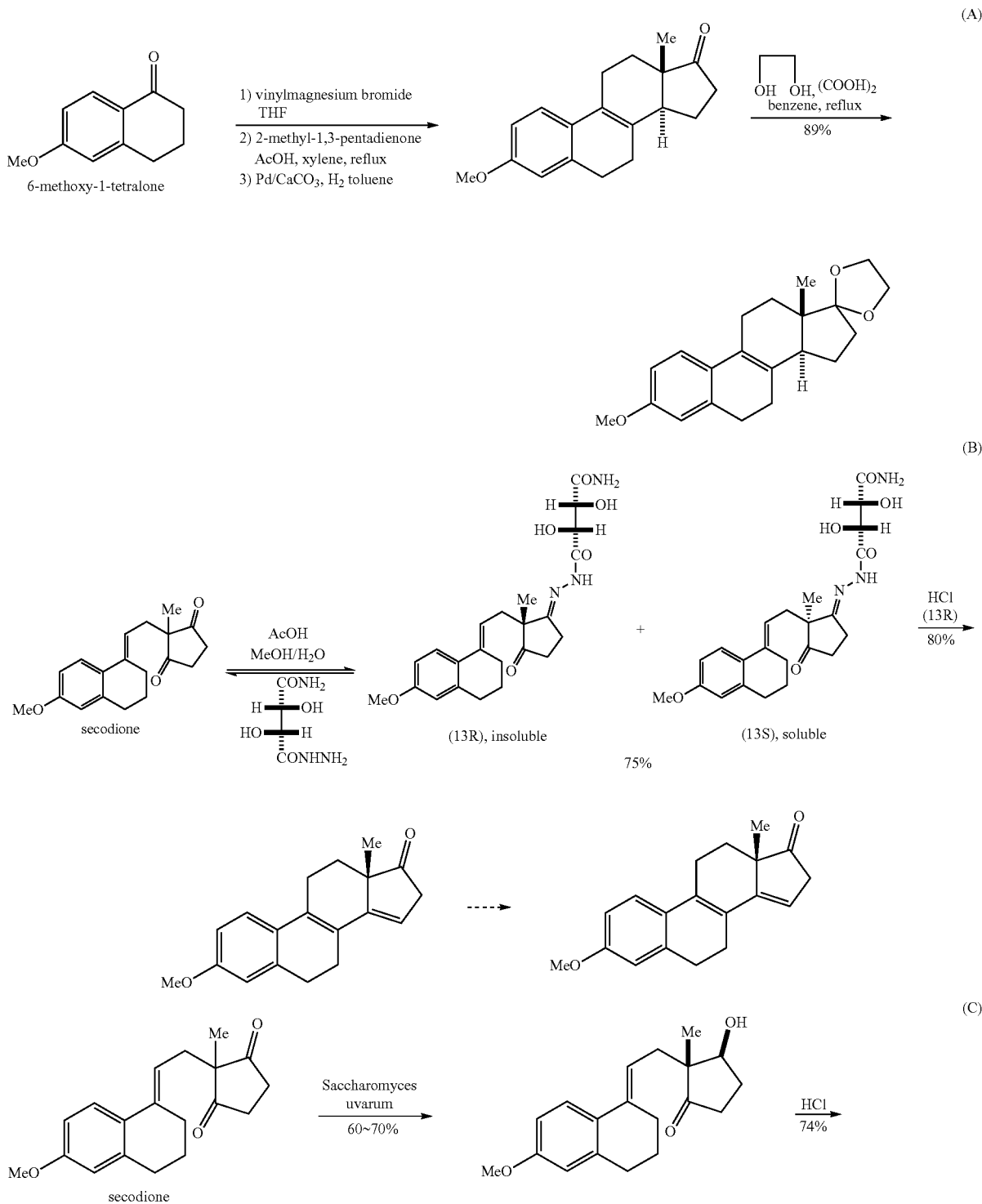

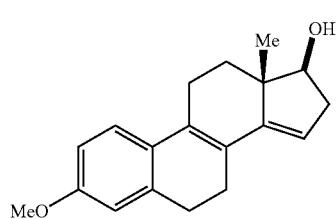
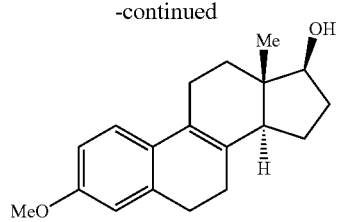

With compounds of Formula (IV-A) and (IV-B) in hand, epoxidation/epoxide opening/epoxidation reactions are conducted (e.g., MMPP, mCPBA) in one-pot to provide the compound of Formula (IX-A) and (IX-B), which are under equilibrium with (IX-A) as a major compound. See Schemes 7A and 7B.

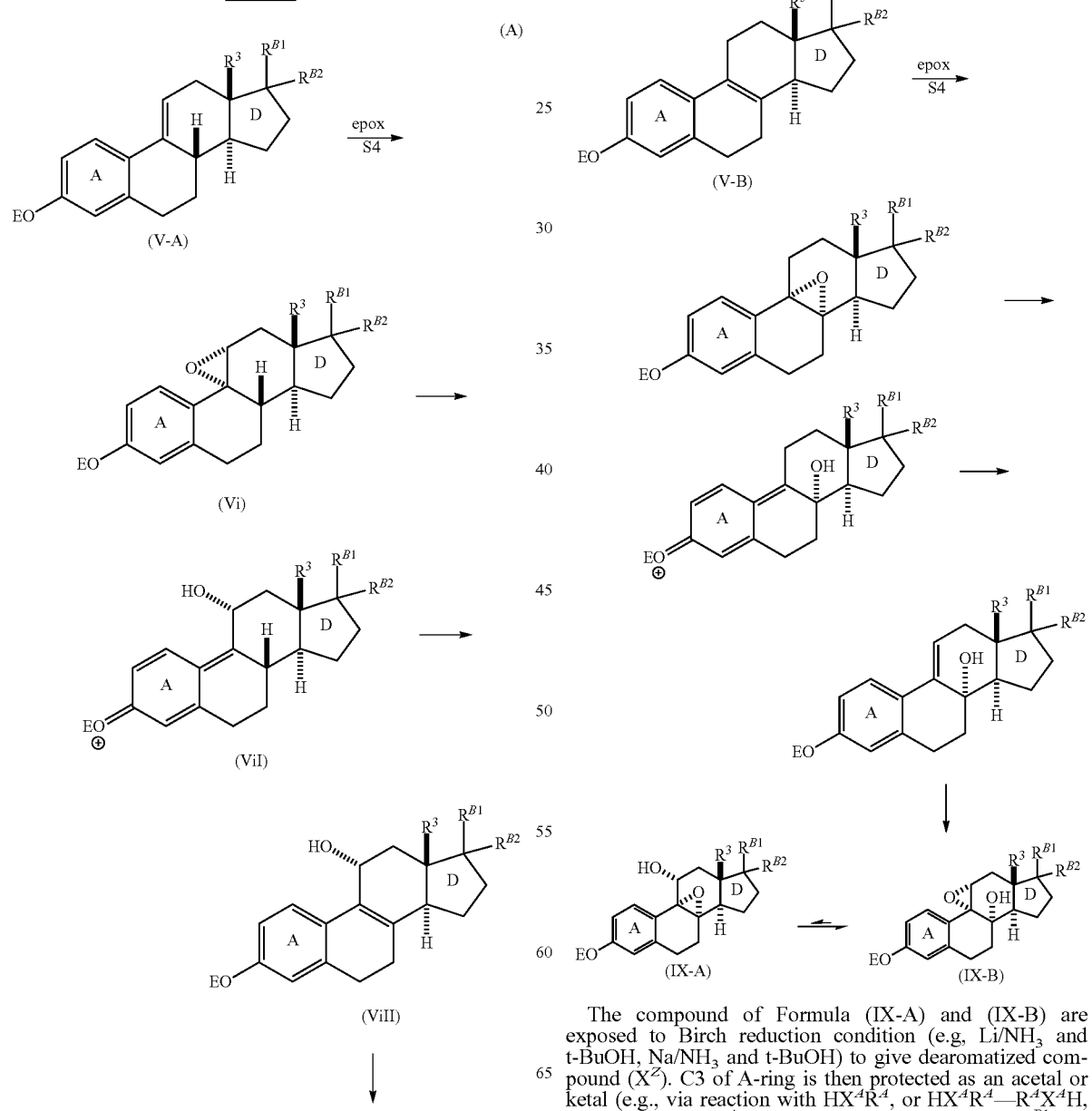

The compound of Formula (IX-A) and (IX-B) are exposed to Birch reduction condition (e.g, Li/NH$_3$ and t-BuOH, Na/NH$_3$ and t-BuOH) to give dearomatized compound ($X^Z$). C3 of A-ring is then protected as an acetal or ketal (e.g., via reaction with HX$^A$R$^A$, or HX$^A$R$^A$—R$^A$X$^A$H, wherein the two R$^A$ groups are joined, and wherein R$^{B1}$ and $R^{B2}$ are each independently —$X^A R^A$) to afford the compound (XI). Exemplary protection conditions include PTSA and ethylene glycol, PTSA and CH(OMe)$_3$, PTSA and CH(OEt)$_3$, and PTSA and 2,2-dimethyl-1,3-propandiol. See Scheme 8.

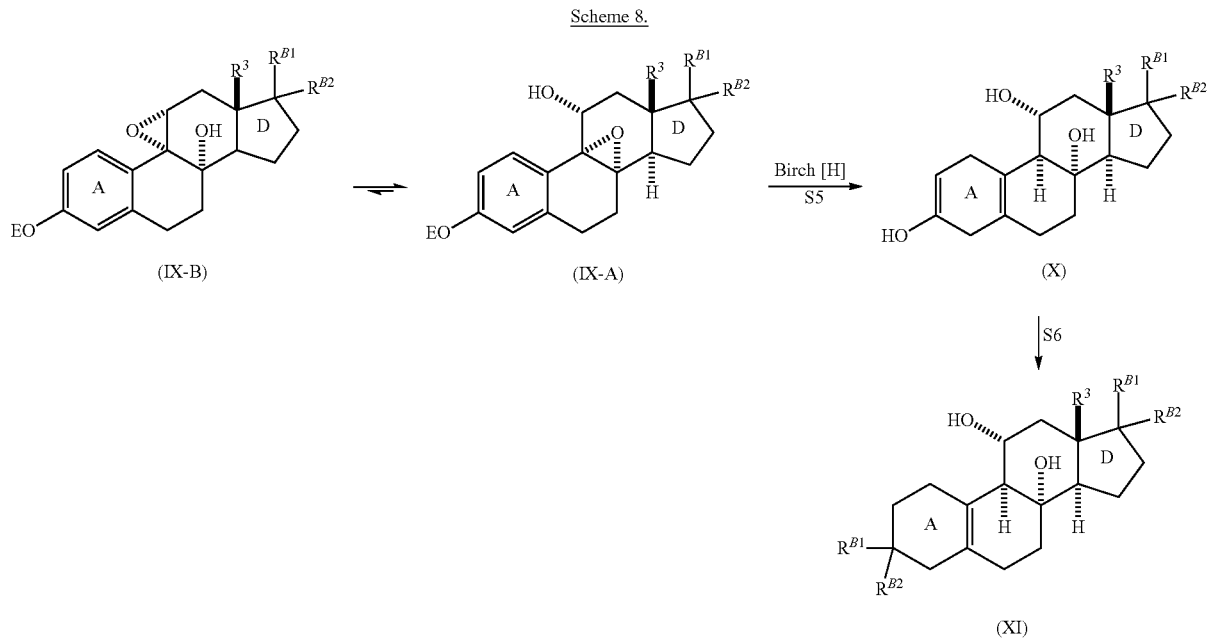

The compound (XI) is converted to a compound of Formula (XIII) through etherification (e.g., NBS, NIS, e.g., wherein X is Br or I). This compound is then oxidized (e.g., SO3 Py/DMSO and triethylamine, IBX, (COCl)$_2$/DMSO and triethylamine) to provide the compound of Formula (XIV). This compound is then treated with base (e.g., DBU, triethylamine) to provide the compound of Formula (XV). This compound is then reduced (e.g., NaBH$_4$ and CeCl$_3$, L-selectride) to provide the compound of Formula (XVI). See Scheme 9.

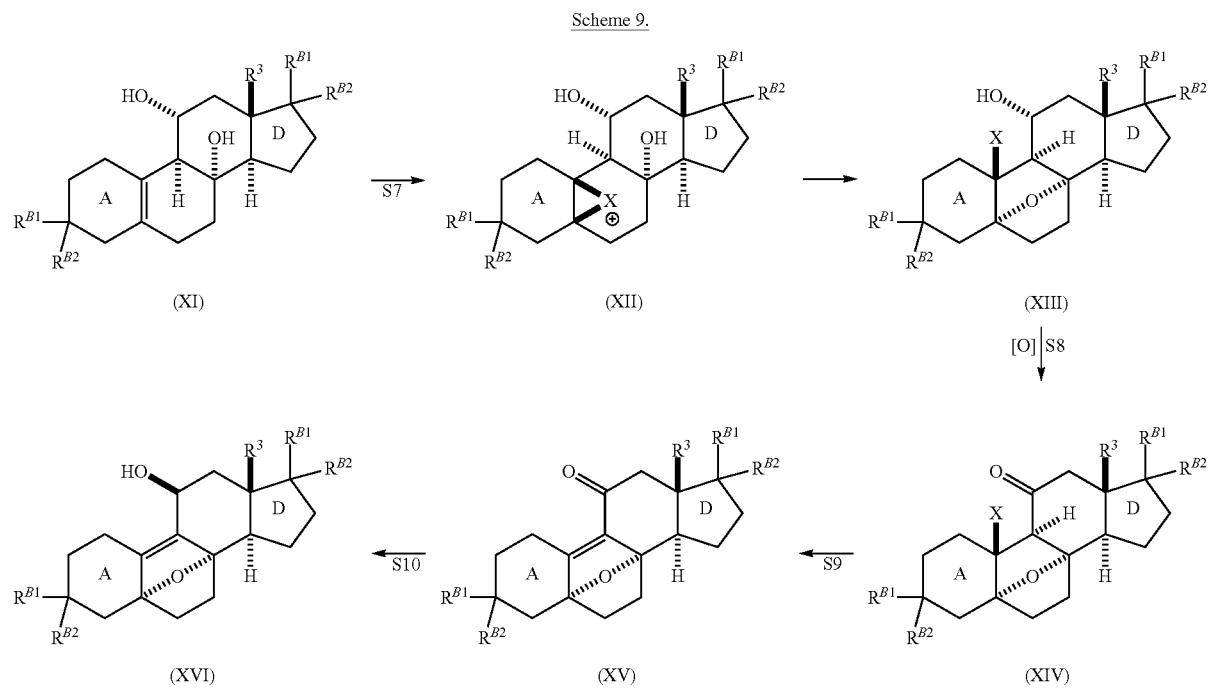

The compound of Formula (XVI) is then treated with cyclopropanation reagents (e.g., ZnEt$_2$ and ClCH$_2$I, ZnEt$_2$ and CH$_2$I$_2$, Zn—Cu and CH$_2$I$_2$) to provide a compound of Formula (XVII). The alcohol of the cyclopropanated product is activated, wherein LG$^1$ is a sulfonyl (e.g., the alcohol is treated with Tf$_2$O, MsCl, to provide an activated alcohol wherein LG$^1$ is Tf or Ms) and treated with base (e.g., 2,6-di-t-butyl-4-methylpyridine, 2,6-lutidine, triethylamine) to provide the compound of Formula (XX). See, e.g., Magnus et al., *Org. Lett.* 2009, 11, 3938-3941. See Scheme 10.

et al., *Nature. Chem.* 2010, 2, 886-892, and Yamashita et al., *J. Org. Chem.* 2011, 76, 2408-2425. See Scheme 11A.

Compound (XXIV) may also be prepared from (XX) through conversion to an activated alcohol, wherein LG$^2$ is a sulfonyl (e.g., the alcohol is treated with Tf$_2$O, MsCl, to provide an activated alcohol wherein LG$^2$ is Tf or Ms; by triflation, e.g., KHMDS and PhNTf$_2$, LiHMDS and PhNTf$_2$, Tf$_2$O and 2,6-di-t-butyl-4-methylpyridine) followed by palladium-catalyzed cross coupling with R$^{B1}$-M, wherein M is a substituted boron (e.g., such as —B(R')$_2$, wherein each R' is —OR" or alkyl wherein the alkyl and R" is alkyl or may

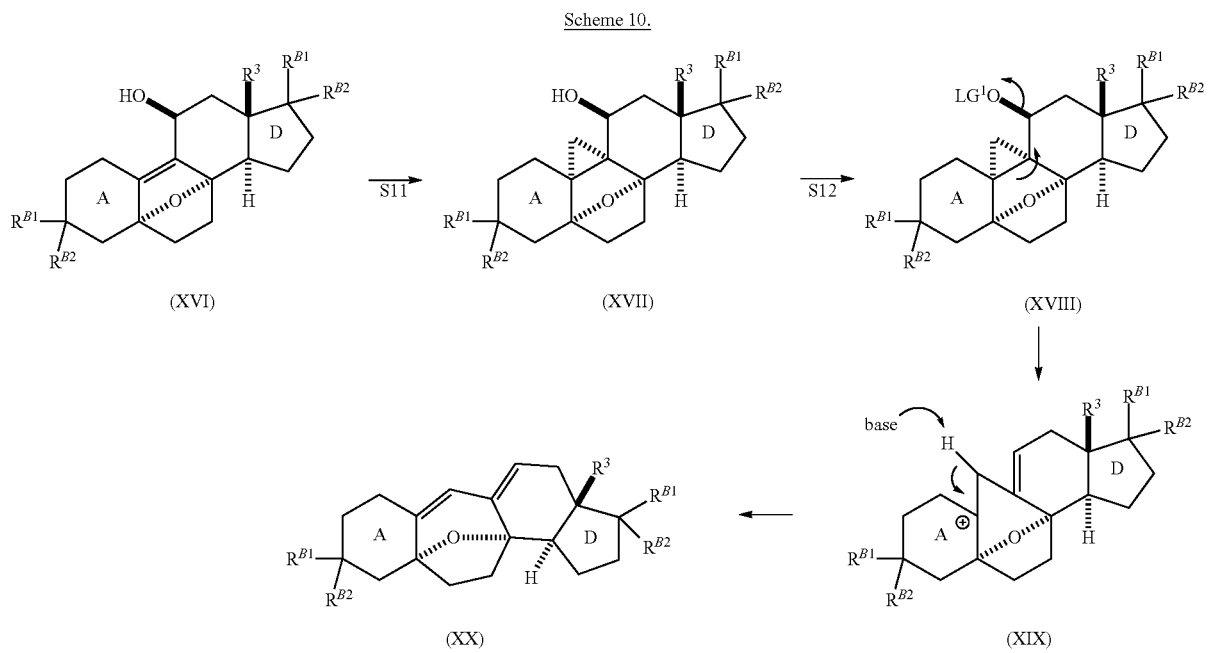

Scheme 10.

Protecting group on D-ring of the compound of Formula (XX) is then deprotected under acidic conditions (e.g., PTSA and acetone/water, TFA/water) to provide the ketone intermediate of Formula (XXI). This product is treated with a compound of Formula R$^{B1}$-M (e.g., R$^{B1}$-CeCl$_2$, R$^1$—Mg) which is prepared from R$^{B1}$—X (e.g., R$^{B1}$—Br, R$^{B1}$—I) to provide a compound of Formula (XXII), wherein R$^{B1}$ is a non-hydrogen group as defined herein. The compound of Formula (XXII) is activated (e.g., TFAA and pyridine, PhNCS and KH) to provide a compound of Formula (XXIII). Reduction of the compound of Formula (XXIII) (e.g., AIBN and Bu$_3$SnH) provides the compound of Formula (XXIV). For steps S14, S15 and S16, see, e.g., Flyer be joined to form a ring) to provide the compound of Formula (XXVI). Exemplary palladium-catalyzed cross coupling conditions include, but are not limited to, R$^{B1}$—B(pin), R$^{B1}$-(9-BBN—H), R$^{B1}$-OBBD, or R$^{B1}$—B(cat), and Pd(PPh$_3$)$_4$ and Na$_2$CO$_3$, or Pd(dppf)Cl$_2$ and K$_3$PO$_4$) (pin=pinacol; cat=catechol; OBBD=9-oxa-10-brabicyclo [3.3.2]decane; 9-BBN—H=9-broabicyclo[3.3.1]nonane). See, e.g., Nicolaou et al., *J. Am. Chem. Soc.* 2009, 131, 10587-10597. Hydrogenation of C16-C17 double bond (e.g., Pd/C and H$_2$, Raney Ni and H$_2$) gives the compound of Formula (XXIV). See Scheme 11B.

Scheme 11.

(A)

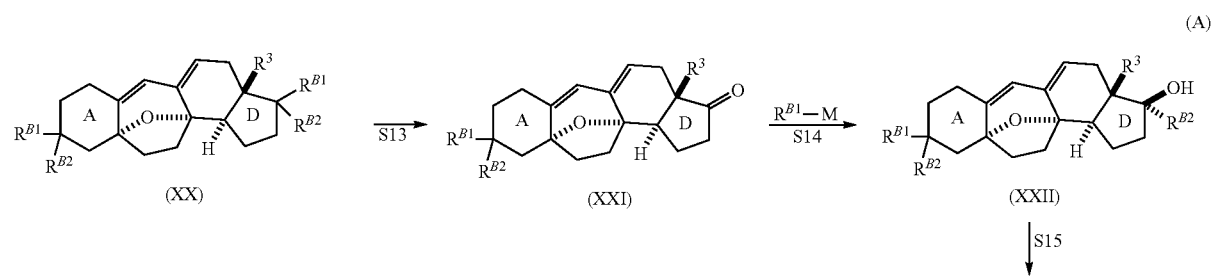

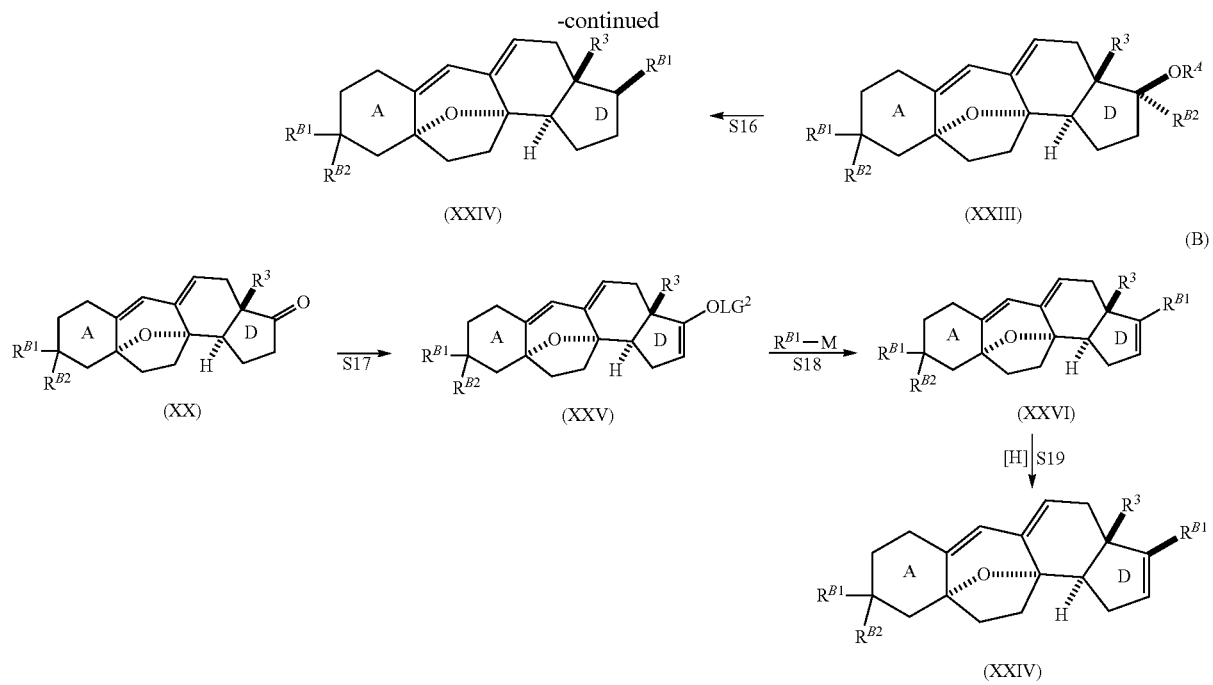

(XXIV) ←S16— (XXIII)

(B)

(XX) —S17→ (XXV) —R^{B1}—M / S18→ (XXVI)

[H] | S19 ↓

(XXIV)

Any one of the compounds of Formula (XXVI) or (XXIV) may then be deprotected (e.g., PTSA and acetone/water, TFA/water, HCl) and the resulting ketone may be trapped as the enolate, followed by subsequent oxidation or amination of the double bond, or reaction of the double bond with an electrophilic carbon $C(R^A)_3$-LG, wherein LG is a leaving group, to provide a substituted ketone product, wherein $R^5$ is —$OR^A$, —$OC(=O)R^A$, —$OC(=O)OR^A$, —$OC(=O)N(R^A)_2$, —$OS(=O)_2R^A$, —$N_3$, —$N(R^A)_2$, —$NR^AC(=O)R^A$, —$NR^AC(=O)OR^A$, —$NR^AC(=O)N(R^A)_2$, —$NR^AS(=O)_2R^A$, or —$C(R^A)_3$. See Schemes 12A and 12B. Exemplary conditions contemplated for enolate trapping include a combination of a base (e.g., lithium diisopropyl amide (LDA)) and a trapping reagent $P_1$-LG, wherein $P_1$ is silyl and LG is a leaving group (e.g., such as trimethylsilyl chloride).

Exemplary oxidative conditions, e.g., to install a —$OR^A$, —$OC(=O)R^A$, —$OC(=O)OR^A$, —$OC(=O)N(R^A)_2$, or —$OS(=O)_2R^A$ group at the $R^5$ position include treating the trapped enolate with an oxidant, such as meta-chloroperoxybenzoic acid (MCPBA), MoOOPh, or DMSO, to provide a substituted ketone wherein $R^5$ is —OH, followed by optional protection, e.g., via treatment of the compound wherein $R^5$ is —OH with a compound of formula $R^A$-LG, LG-C(=O)$R^A$, LG-C(=O)O$R^A$, LG-C(=O)N($R^A$)$_2$, or LG-S(=O)$_2R^A$, wherein LG is a leaving group, to provide a compound wherein $R^5$ is —$OR^A$ (wherein $R^A$ is a non-hydrogen group), —$OC(=O)R^A$, —$OC(=O)OR^A$, —$OC(=O)N(R^A)_2$, or —$OS(=O)_2R^A$.

Exemplary aminating conditions, e.g., to install an —$N_3$, —$N(R^A)_2$, —$NR^AC(=O)R^A$, —$NR^AC(=O)OR^A$, —$NR^AC(=O)N(R^A)_2$, or —$NR^AS(=O)_2R^A$ group at the $R^5$ position include treating the trapped enolate with a compound $N_3$-LG wherein LG is a leaving group (e.g., such as trisylazide) to provide the substituted ketone wherein $R^5$ is —$N_3$. The substituted ketone wherein $R^5$ is —$N_3$ may be treated with a reducing agent (e.g., such as $PPh_3$) to provide a compound wherein $R^5$ is —$NH_2$, followed by optional protection, e.g., via treatment of the compound wherein $R^5$ is —$NH_2$ with a compound of formula $R^A$-LG, LG-C(=O)$R^A$, LG-C(=O)O$R^A$, LG-C(=O)N($R^A$)$_2$, or LG-S(=O)$_2R^A$, wherein LG is a leaving group, to provide a compound wherein $R^5$ is —$N(R^A)_2$ (wherein at least one of $R^A$ is a non-hydrogen group), —$NR^AC(=O)R^A$, —$NR^AC(=O)OR^A$, —$NR^AC(=O)N(R^A)_2$, or —$NR^AS(=O)_2R^A$.

Scheme 12.

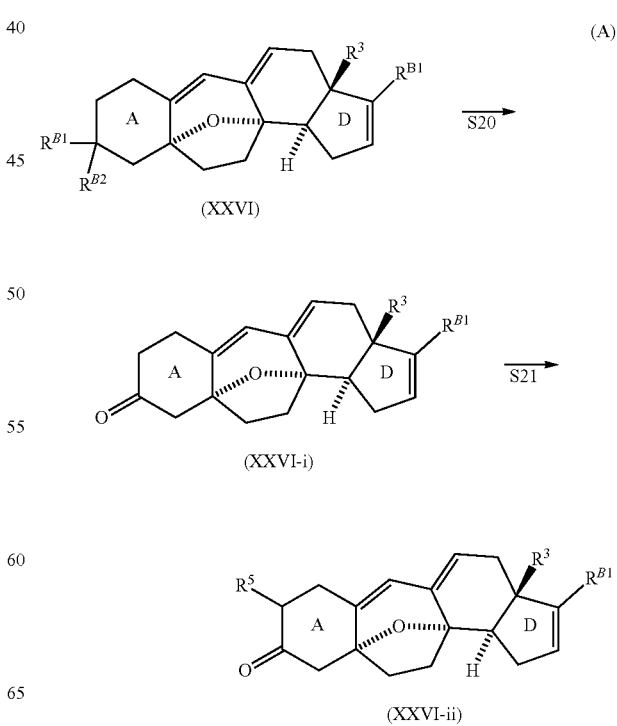

(A)

(XXVI) —S20→

(XXVI-i) —S21→

(XXVI-ii)

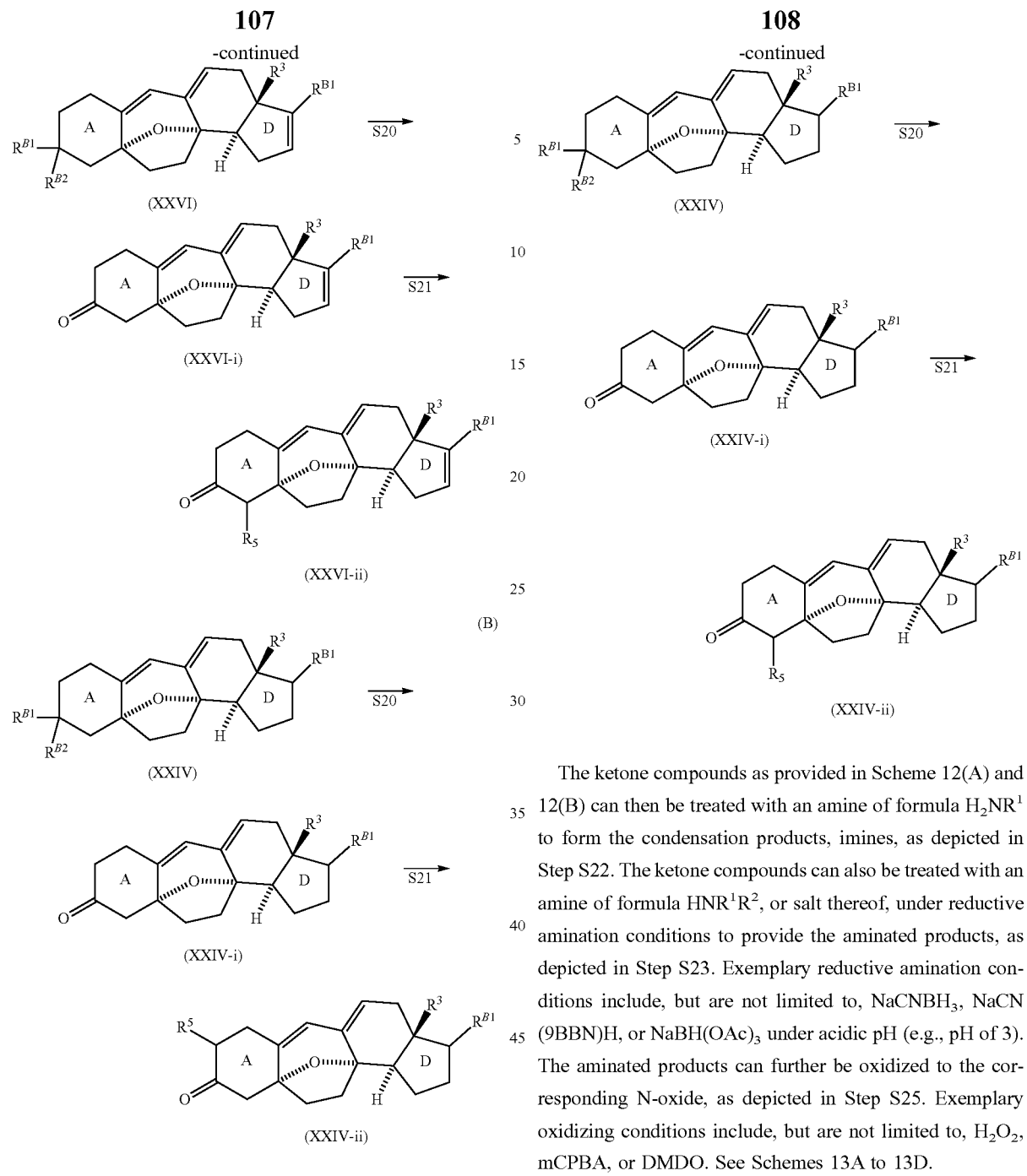

The ketone compounds as provided in Scheme 12(A) and 12(B) can then be treated with an amine of formula $H_2NR^1$ to form the condensation products, imines, as depicted in Step S22. The ketone compounds can also be treated with an amine of formula $HNR^1R^2$, or salt thereof, under reductive amination conditions to provide the aminated products, as depicted in Step S23. Exemplary reductive amination conditions include, but are not limited to, $NaCNBH_3$, NaCN (9BBN)H, or $NaBH(OAc)_3$ under acidic pH (e.g., pH of 3). The aminated products can further be oxidized to the corresponding N-oxide, as depicted in Step S25. Exemplary oxidizing conditions include, but are not limited to, $H_2O_2$, mCPBA, or DMDO. See Schemes 13A to 13D.

Scheme 13.

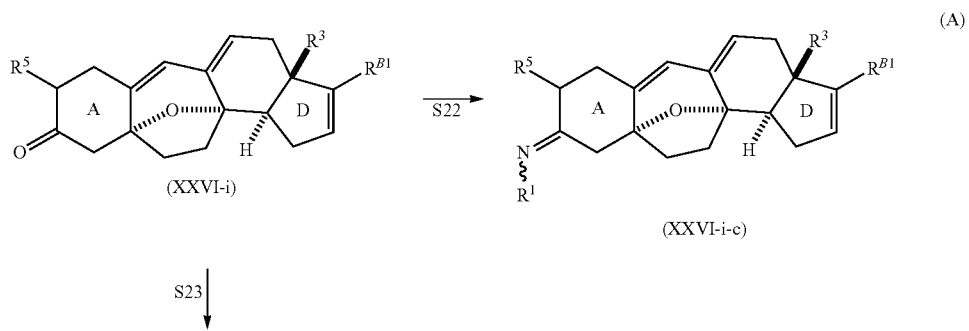

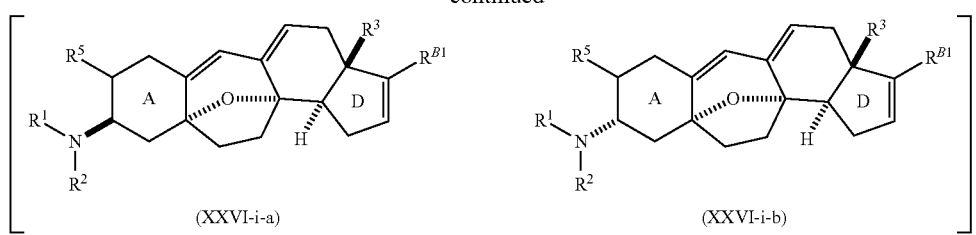
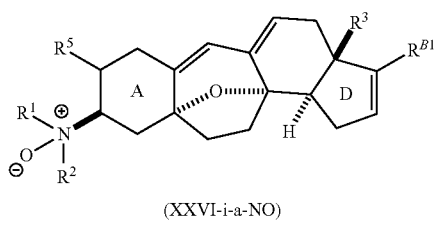
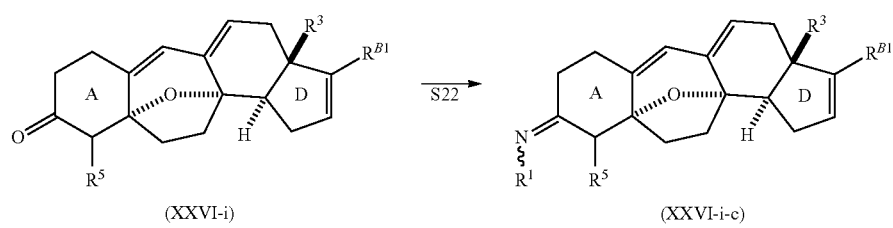
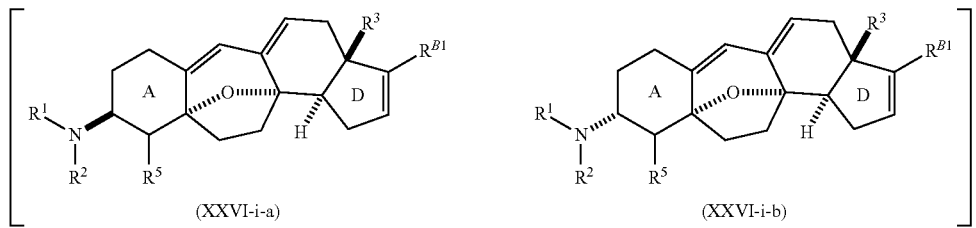
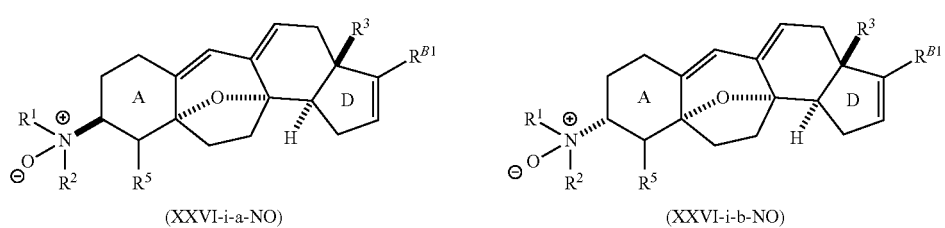

(C)
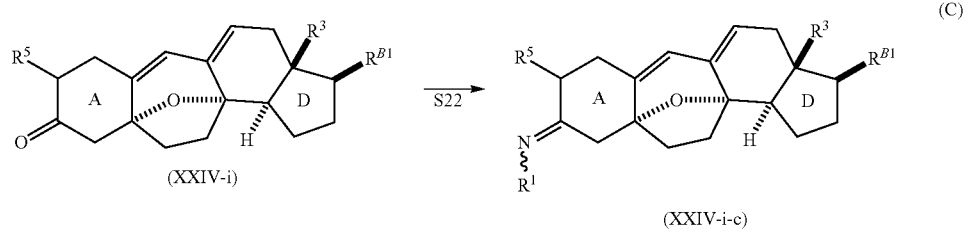
(XXIV-i) →S22→ (XXIV-i-c)
↓S23
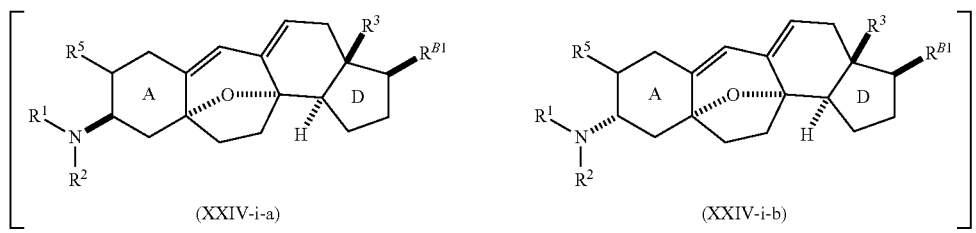
[ (XXIV-i-a)    (XXIV-i-b) ]
↓S25    ↓S25
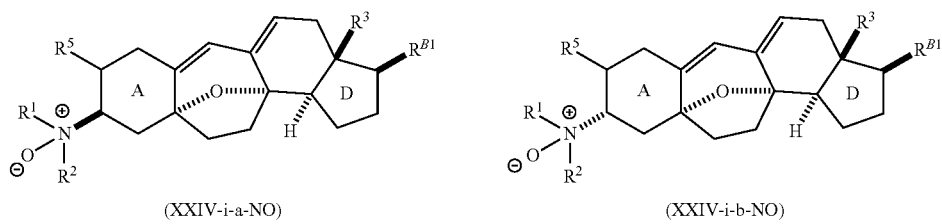
(XXIV-i-a-NO)    (XXIV-i-b-NO)
(D)
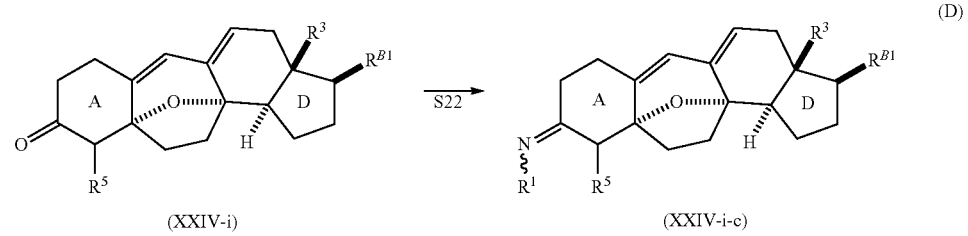
(XXIV-i) →S22→ (XXIV-i-c)
↓S23
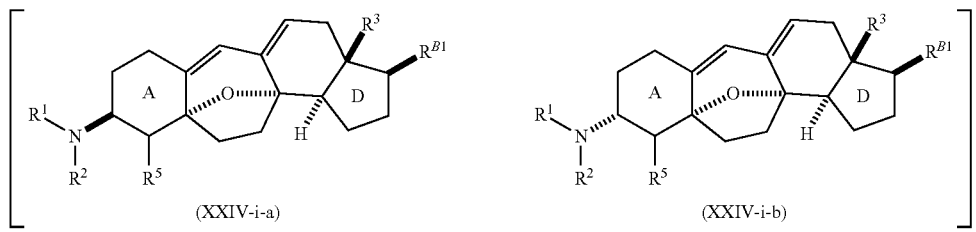
[ (XXIV-i-a)    (XXIV-i-b) ]
↓S25    ↓S25

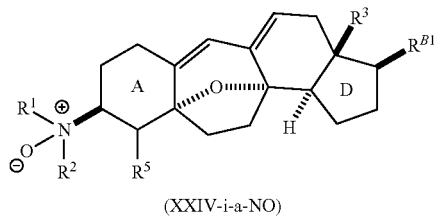

(XXIV-i-a-NO)

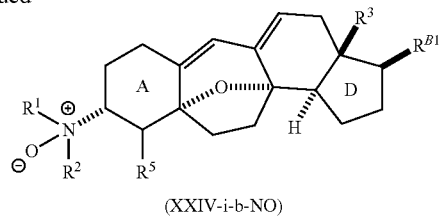

(XXIV-i-b-NO)

The keto compound can also be converted to the compound of Formula (XXV-i) through palladium-catalyzed carbonylative amination with CO and $HN(R^L)R^{B3}$ (e.g., $Pd(PPh_3)_4$ and triethylamine, $Pd(dppf)Cl_2$ and triethylamine). Conditions for the following steps to get to the compound of Formula (XXV-i), (XXV-iv), and (XXV-v) are the same as described previously. See Scheme 14.

Scheme 14.

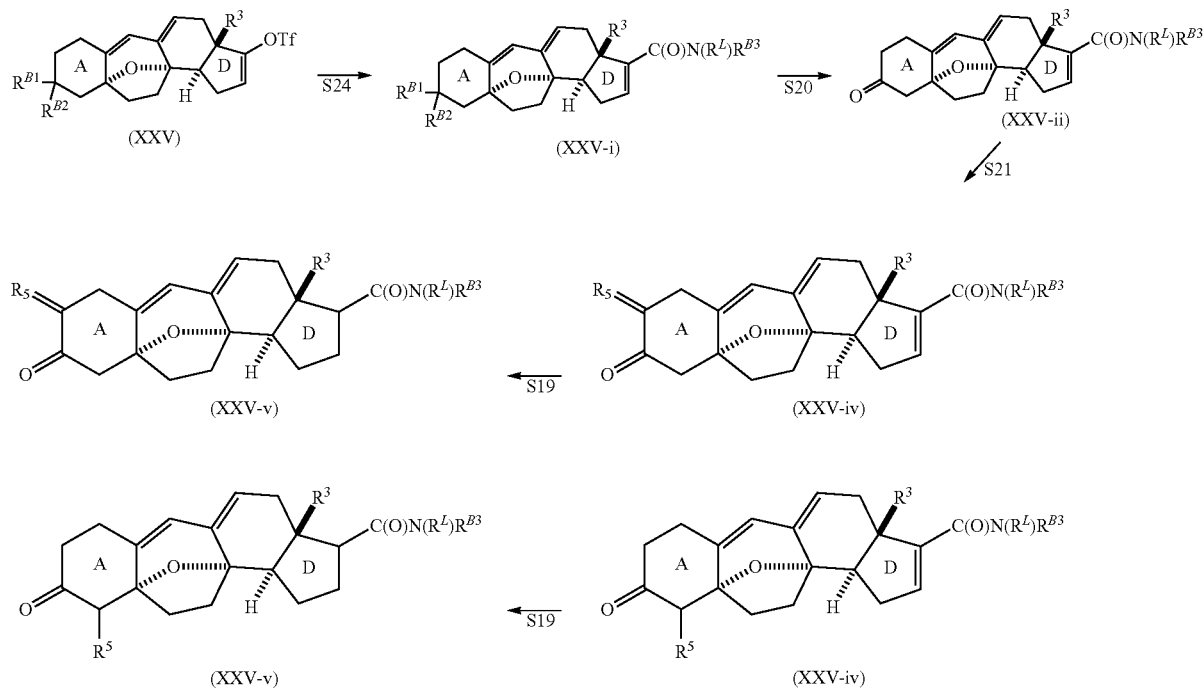

The ketone compounds as provided in Scheme 14 can then be converted to the corresponding imines, amines, and N-oxides, as described previously. See Scheme 15A and 15B.

Scheme 15.

(A)

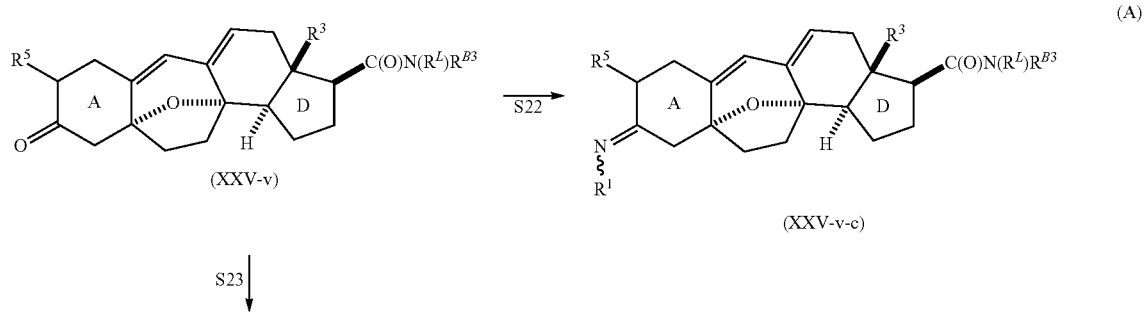

-continued
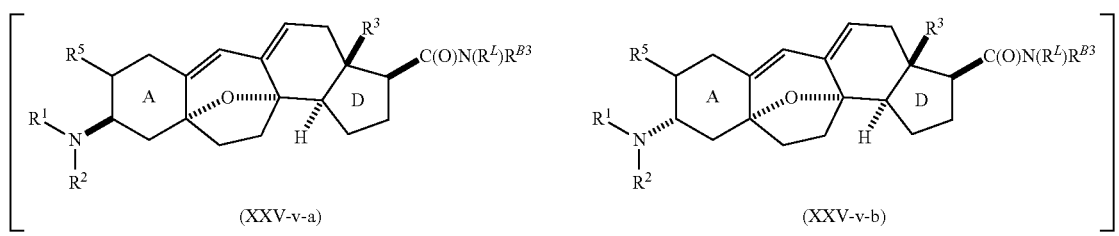
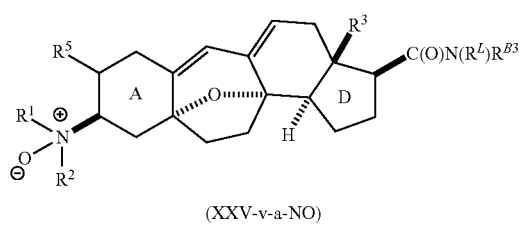
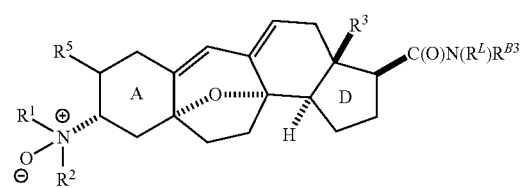
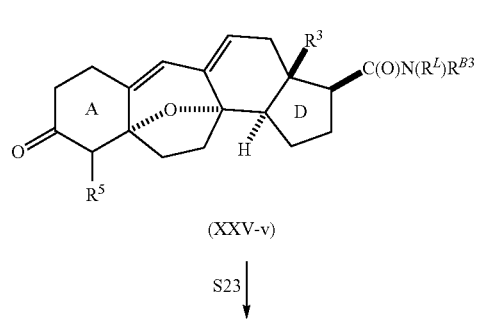
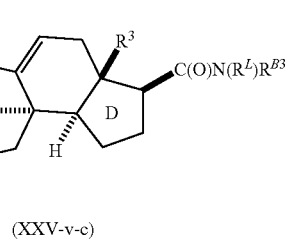
(B)
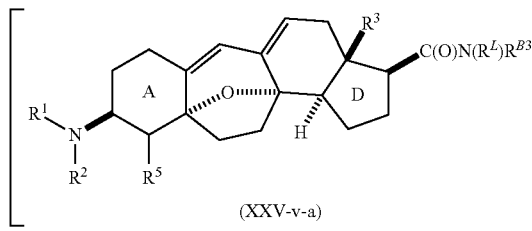
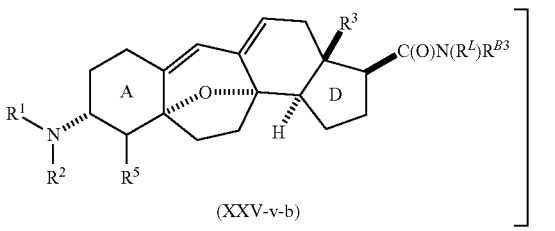
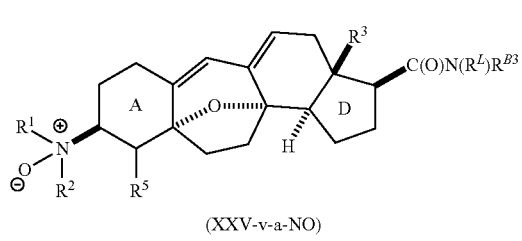

The monoketone compound (XXI) can be reductively aminated with HNR$^{B4}$R$^{B5}$ (e.g., 1,2,3,4-tetrahydro-[2,7] naphthyridine) under conditions previously described to provide the compound of Formular (XXVII). Compound (XXVII) can be converted to the corresponding imines, amines, and N-oxides, as described previously. See Schemes 16(A) and 16(B).
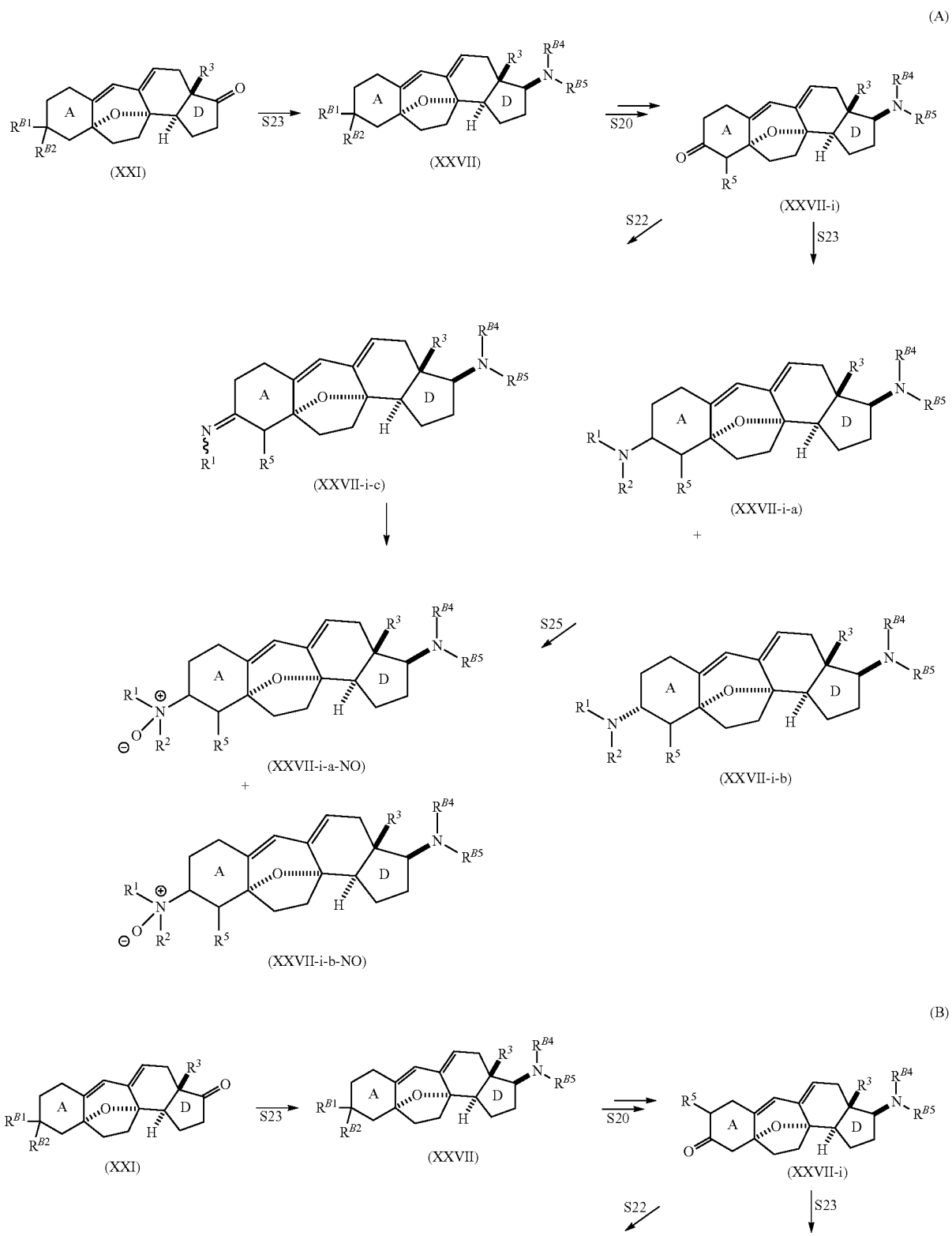
Scheme 16.

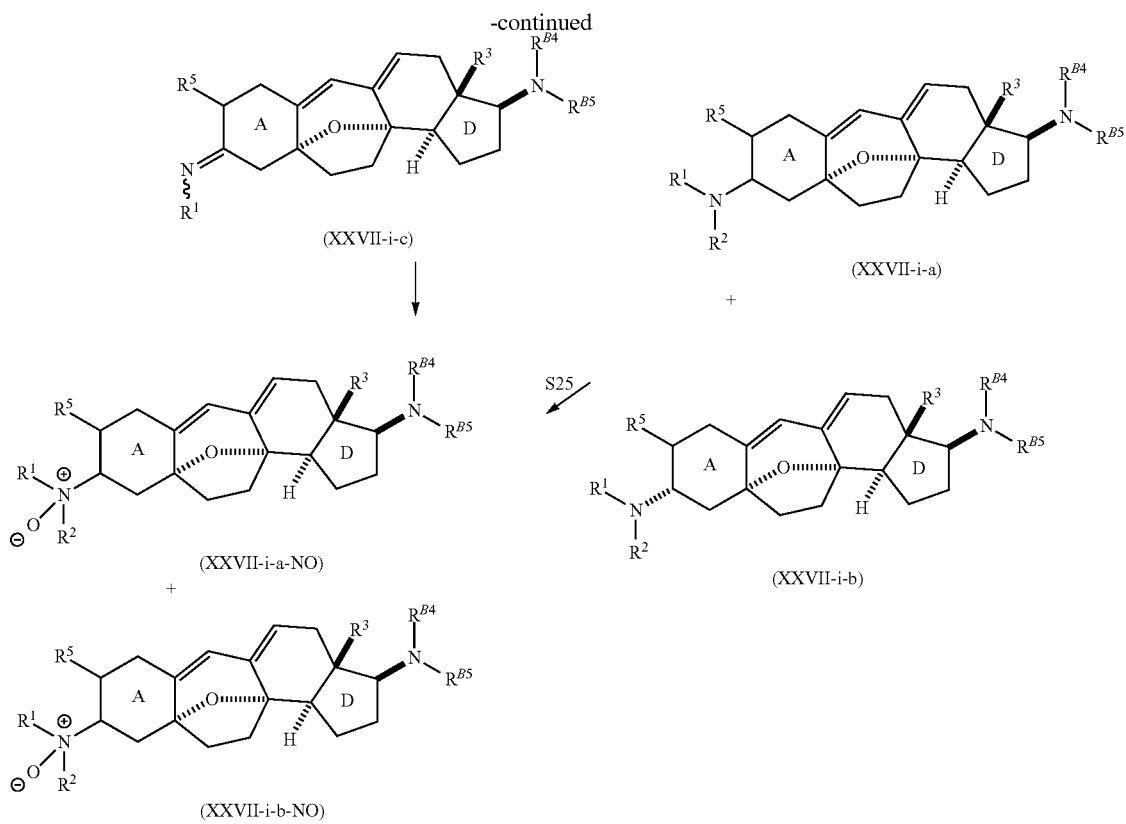

The ketone may be further synthetically manipulated to provide other compounds of interest. For example, the ketone may be reduced (as depicted in step S26) in the presence of a reducing agent to provide the C-3 hydroxylated compound. See Schemes 17 (A) and (B). Exemplary reducing agents include L-selectride, K-selectride, diisobutylaluminum hydride (DIBALH), and lithium aluminum hydride (LAH). Furthermore, various reducing agents will preferentially generate one C-3 hydroxylated compounds as the major isomer over the other, e.g., using L-selectride the beta isomer is preferably generated as the major isomer, while using lithium aluminum hydride (LAH) the alpha is preferably generated as the major isomer. Alternatively, the ketone may be reduced (as depicted in step S30) under Wolff-Kishner reductive conditions to provide compounds of Formula (G1) and (G2). See Scheme 18. Exemplary Wolff-Kishner conditions are described in Furrow, M. E.; Myers, A. G. (2004). "Practical Procedures for the Preparation of N-tert-Butyldimethylsilylhydrazones and Their Use in Modified Wolff-Kishner Reductions and in the Synthesis of Vinyl Halides andgem-Dihalides". *Journal of the American Chemical Society* 126 (17): 5436-5445, incorporated herein by reference.

Scheme 17.

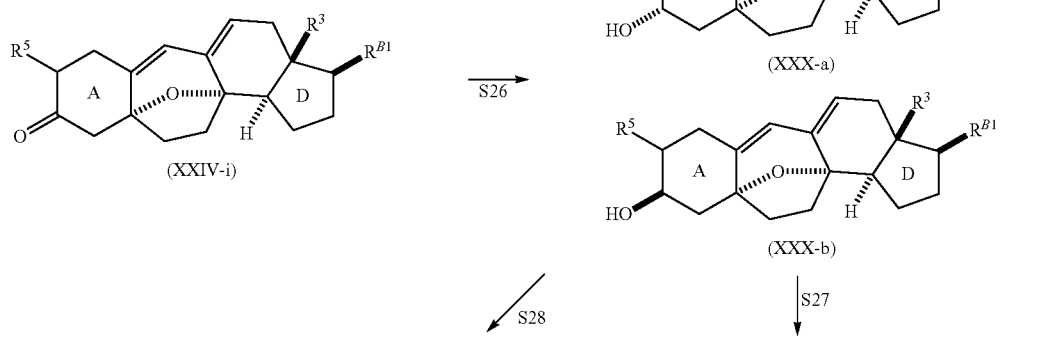

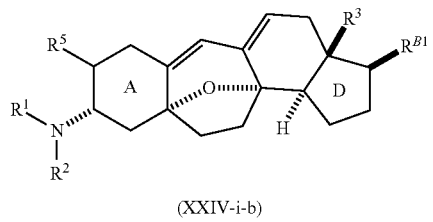
(XXIV-i-b)
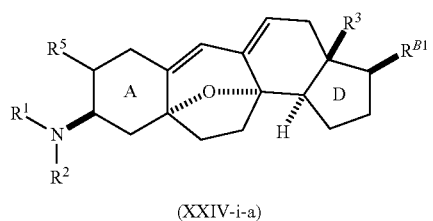
(XXIV-i-a)
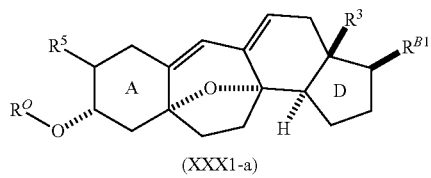
(XXXI-a)
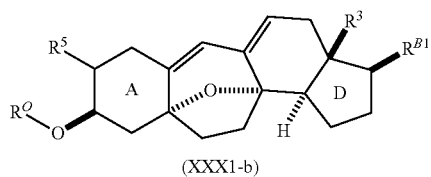
(XXXI-b)
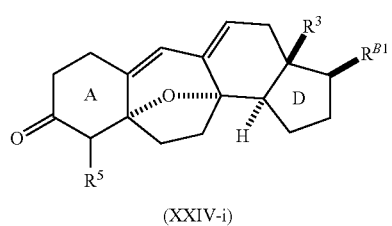
(XXIV-i)
(B)
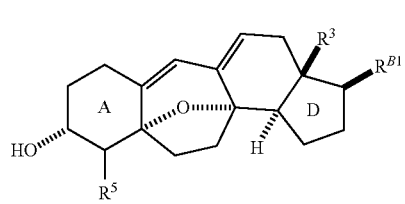
(XXX-a)
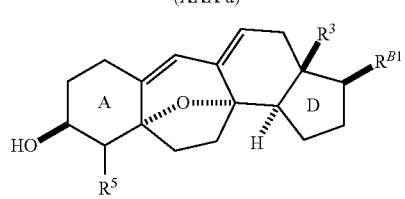
(XXX-b)
S26
S28
S27
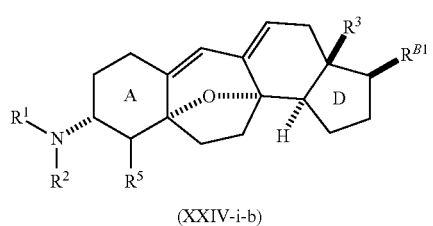
(XXIV-i-b)
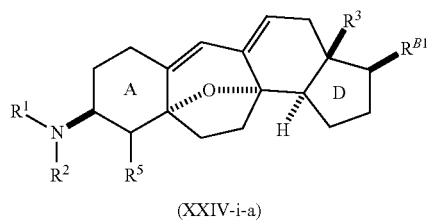
(XXIV-i-a)
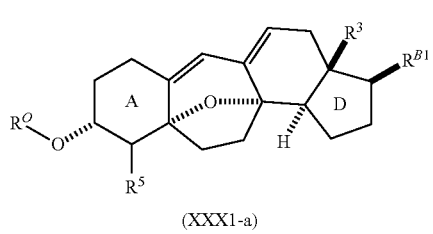
(XXXI-a)
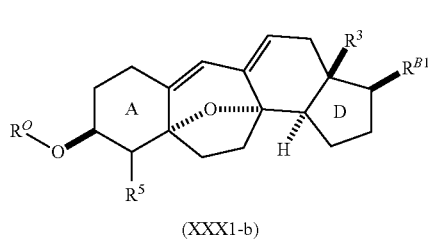
(XXXI-b)

Scheme 18.

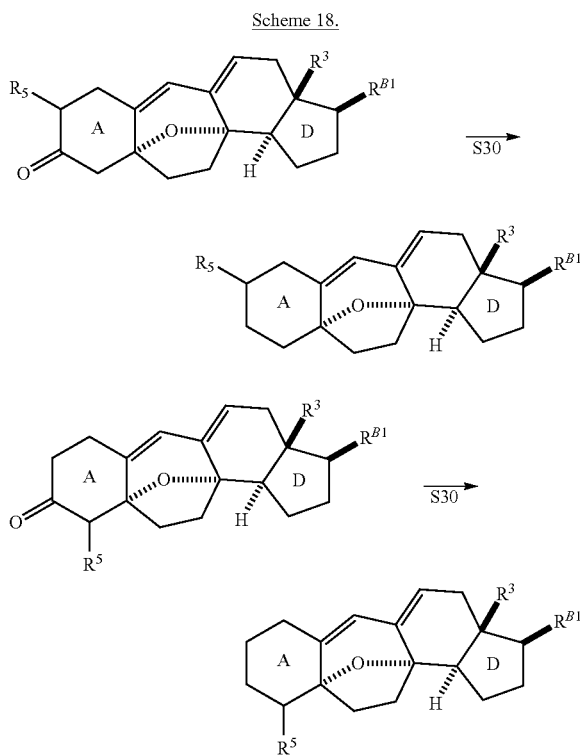

As used herein, a "major isomer" refers to the isomer that is produced in excess of the other isomer, i.e., greater than 50% of the sum of the two isomers produced from the reaction, e.g., greater than 60%, 70%, 80%, 90%, or 95% of the sum of the two isomers produced from the reaction.

The C-3 hydroxylated compound may then be activated to a compound of Formula (E') or (E'') (e.g., by reaction with a group LG-C(=O)$R^A$, wherein LG is a leaving group, either prior to commencing the reaction or in situ (during the reaction) via substitution with a group of formula —C(=O)$R^A$ under Mitsunobu reaction conditions (e.g., with HOC(=O)$R^A$, diethylazodicarboxylate (DEAD) or diisopropyl azodicarboxylate (DIAD), and PPh$_3$)) and then treated with an amine of formula NHR$^1$R$^2$ to provide a compound of Formula (A') or (A'') with inverted C3 stereochemistry as the major isomer (as depicted in step S28). See Schemes 17(A) and (B). Alternatively, the C-3 hydroxlated compound of Formula (D') or (D'') may be treated with base and a compound of formula R$^O$-LG, wherein LG is a leaving group, to provide a protected C3-hydroxyl compound with retention of C3-stereochemistry as the major isomer (as depicted in step S27).

Thus, in one aspect, provided is a method of preparing a compound of Formula (B') or (B''):

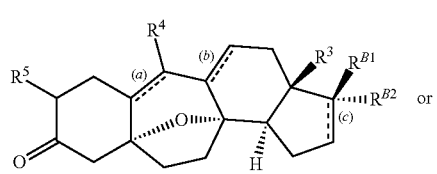

(B')

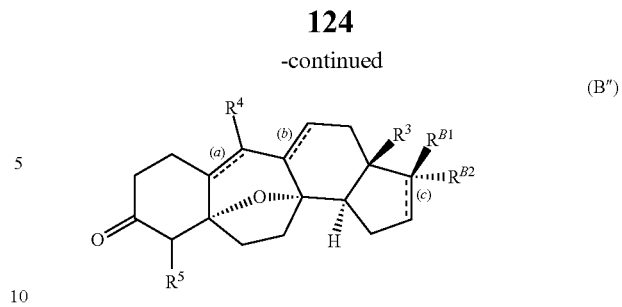

(B'')

or a pharmaceutically acceptable salt, quaternary amine salt, or N-oxide thereof; wherein $R^5$ is —OR$^A$, —OC(=O)R$^A$, —OC(=O)OR$^A$, —OC(=O)N(R$^A$)$_2$, or —OS(=O)$_2$R$^A$, the method comprising treating a compound of Formula:

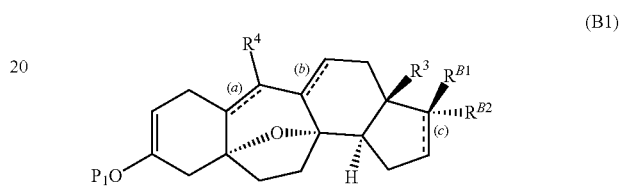

(B1)

or a pharmaceutically acceptable salt, quaternary amine salt, or N-oxide thereof; wherein P$_1$ is silyl, under oxidative conditions.

In certain embodiments, the compound resulting from treatment of the compound of Formula (B1) under oxidative conditions is a compound wherein $R^5$ is —OH. In certain embodiments, the compound of Formula (B') or (B'') wherein $R^5$ is —OH is optionally treated with a compound of formula R$^A$-LG, LG-C(=O)R$^A$, LG-C(=O)OR$^A$, LG-C(=O)N(R$^A$)$_2$, or LG-S(=O)$_2$R$^A$, wherein LG is a leaving group, to provide a compound of Formula (B') or (B'') wherein $R^5$ is —OR$^A$ (wherein R$^A$ is a non-hydrogen group), —OC(=O)R$^A$, —OC(=O)OR$^A$, —OC(=O)N(R$^A$)$_2$, or —OS(=O)$_2$R$^A$.

In another aspect, provided is a method of preparing a compound of Formula (B') or (B''):

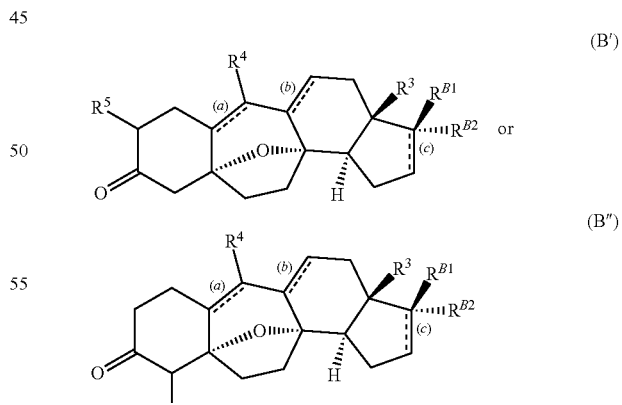

or a pharmaceutically acceptable salt, quaternary amine salt, or N-oxide thereof;

wherein $R^5$ is —N$_3$, —N(R$^A$)$_2$, —NR$^A$C(=O)R$^A$, —NR$^A$C(=O)OR$^A$, —NR$^A$C(=O)N(R$^A$)$_2$, or —NR$^A$S(=O)$_2$R$^A$, the method comprising treating a compound of Formula:

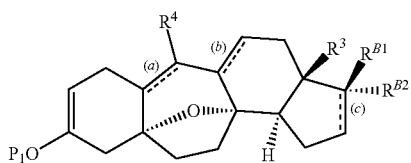

(B1)

or a pharmaceutically acceptable salt, quaternary amine salt, or N-oxide thereof; wherein $P_1$ is silyl, under aminating conditions.

In certain embodiments, the compound resulting from treatment of the compound of Formula (B1) under aminating conditions is a compound wherein $R^5$ is —$N_3$. In certain embodiments, the compound of Formula (B') or (B") wherein $R^5$ is —$N_3$ is reduced to a compound of Formula (B') or (B") wherein $R^5$ is —$NH_2$. In certain embodiments, the compound of Formula (B') or (B") wherein $R^5$ is —$NH_2$ is treated with a compound of Formula $R^A$-LG, LG-C(=O) $R^A$, LG-C(=O)O$R^A$, LG-C(=O)N($R^A$)$_2$, or LG-S(=O)$_2$ $R^A$, wherein LG is a leaving group, to provide a compound of Formula (B') or (B") wherein $R^5$ is —N($R^A$)$_2$ (wherein at least one of $R^A$ is a non-hydrogen group), —$NR^A$C(=O)$R^A$, —$NR^A$C(=O)O$R^A$, —$NR^A$C(=O)N($R^A$)$_2$, or —$NR^A$S(=O)$_2R^A$.

In still yet another aspect, provided is a method of preparing a compound of Formula (B') or (B"):

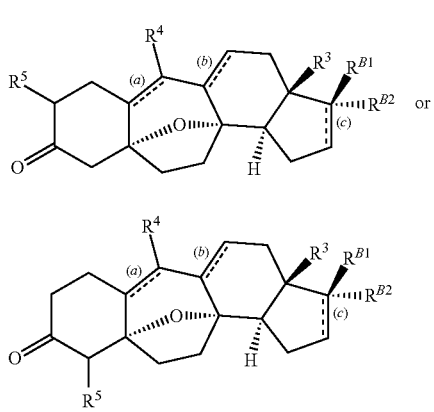

(B')

(B")

or a pharmaceutically acceptable salt, quaternary amine salt, or N-oxide thereof, wherein $R^5$ is —C($R^A$)$_3$, the method comprising treating a compound of Formula:

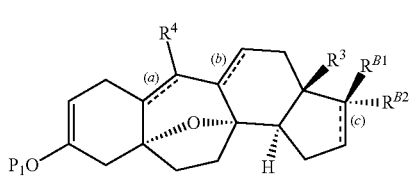

(B1)

or a pharmaceutically acceptable salt, quaternary amine salt, or N-oxide thereof; wherein $P_1$ is silyl, with a compound of formula C($R^A$)$_3$-LG, wherein LG is a leaving group.

In still yet another aspect, provided is a method of preparing a compound of Formula (B1):

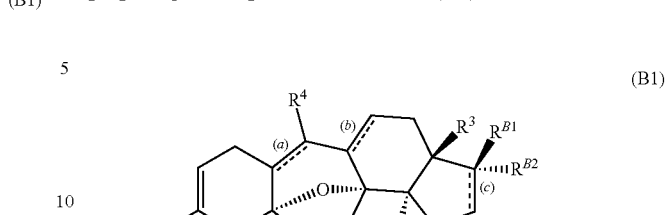

(B1)

or a pharmaceutically acceptable salt, quaternary amine salt, or N-oxide thereof; the method comprising contacting a compound of Formula (B0):

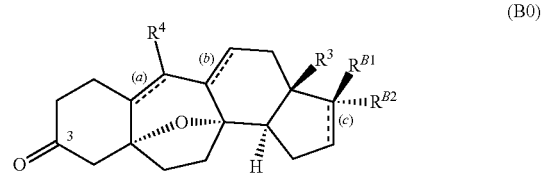

(B0)

with a base and a compound of formula $P_1$-LG, wherein LG is a leaving group.

In another aspect, provided is a method of preparing a compound of Formula A') or (A"):

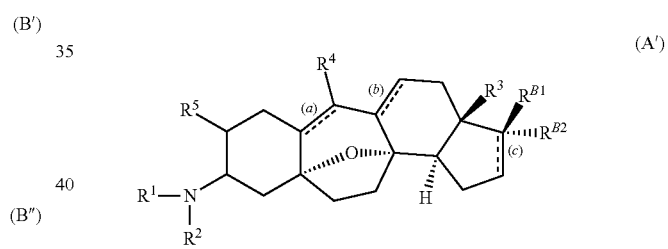

(A')

(A")

or a pharmaceutically acceptable salt, quaternary amine salt, or N-oxide thereof; the method comprising contacting a compound of Formula (B') or (B"):

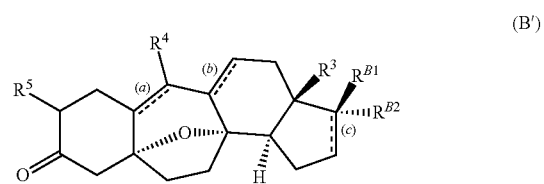

(B')

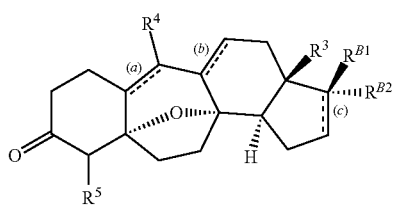

(B")

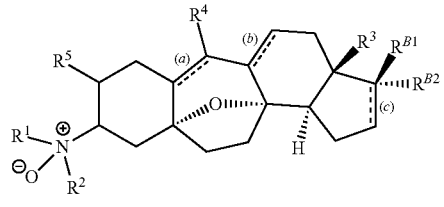

(A-NO')

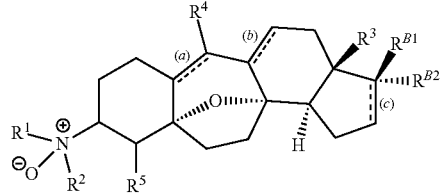

(A-NO")

or a pharmaceutically acceptable salt thereof, provided $R^{B1}$ and $R^{B2}$ are not joined to form an oxo group; with an amine of formula $HNR^1R^2$, or salt thereof, under reductive amination conditions.

In certain embodiments, the method comprises preparing one C3 isomer as the major isomer over the other isomer. For example, in certain embodiments, the method comprises preparing the compound of Formula (A-1') or (A-1") as the major isomer. In other embodiments, the method comprises preparing the compound of Formula (A-2') or (A-2") as the major isomer.

or a pharmaceutically acceptable salt thereof.

In other embodiments, provided is a method of preparing a compound of Formula (D') or (D"):

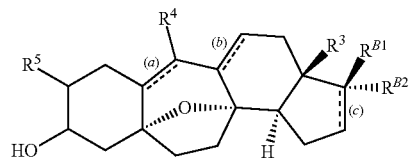

(D')

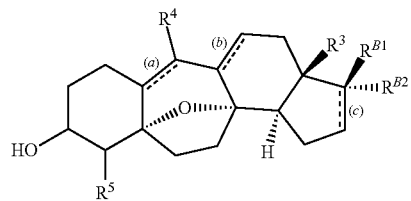

(D")

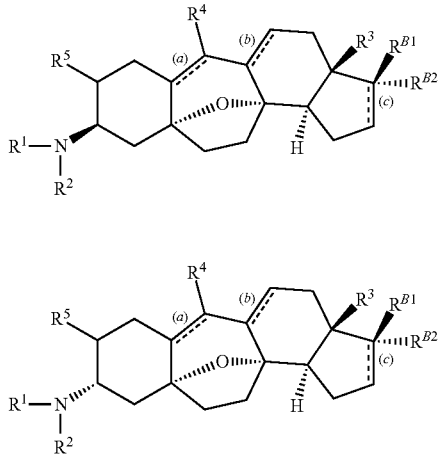

(A-1')

(A-2')

(A-1")

or a pharmaceutically acceptable salt, quaternary amine salt, or N-oxide thereof; the method comprising contacting a compound of Formula (B') or (B"):

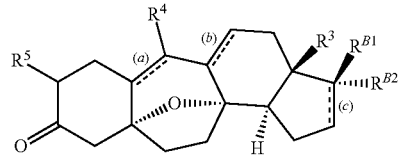

(B')

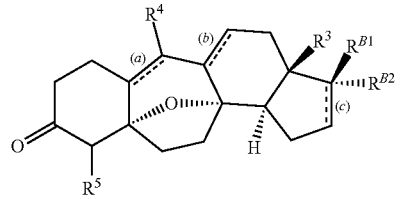

(B")

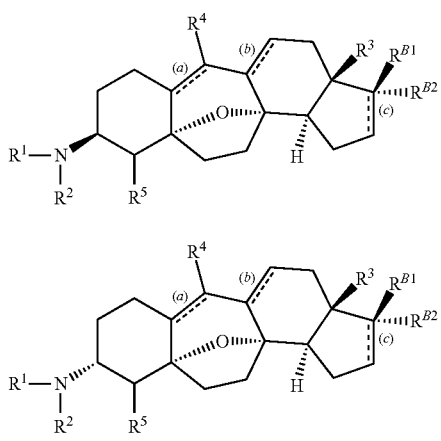

(A-2")

In certain embodiments, the method further comprises oxiding the compound of Formula (A') or (A") to provide an N-oxide of Formula (A-NO') or (A-NO"):

or a pharmaceutically acceptable salt thereof, with a reducing agent. In certain embodiments, the method comprises preparing one C3 isomer as the major isomer over the other isomer.

For example, in certain embodiments, the method comprises preparing the compound of Formula (D-1') or (D-1") as the major isomer. In other embodiments, the method comprises preparing the compound of Formula (D-2') or (D-2") as the major isomer.

(D-1')
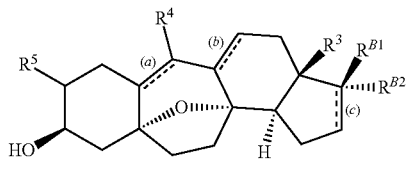

(D-1")
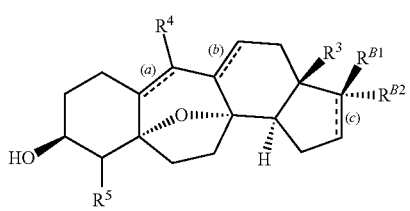

(D-2')
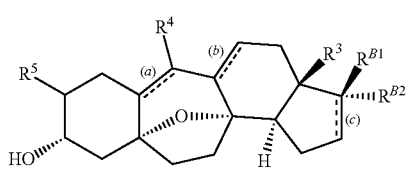

(D-2")
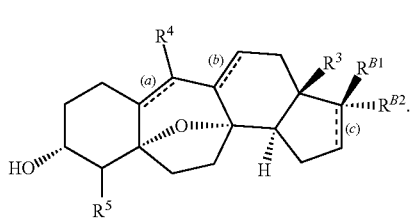

In another aspect, provided is a method of preparing a compound of Formula (E') or (E"):

(E')
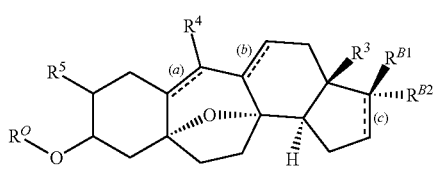

(E")
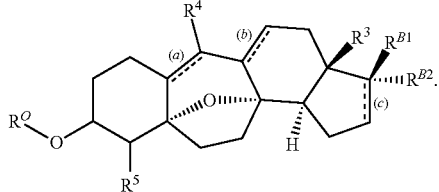

a pharmaceutically acceptable salt thereof; the method comprising contacting a compound of Formula (D') or (D"):

(D')
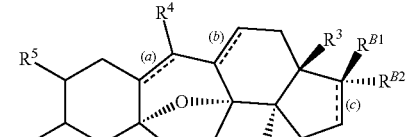

(D")
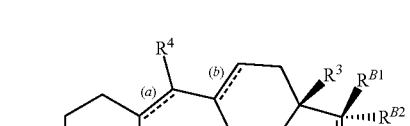

or a pharmaceutically acceptable salt thereof, with a compound of formula $R^O$-LG, wherein LG is a leaving group, to provide a compound of Formula (E') or (E").

In another aspect, provided is a method of preparing a compound of Formula (A') or (A"):

(A')
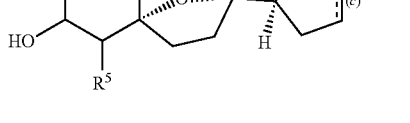

(A")
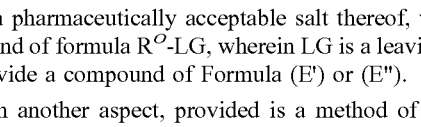

or a pharmaceutically acceptable salt, quaternary amine salt, or N-oxide thereof, the method comprising providing a compound of Formula (E') or (E"):

(E')
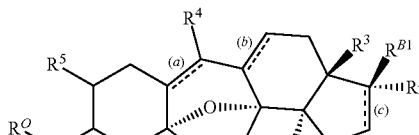

(E")
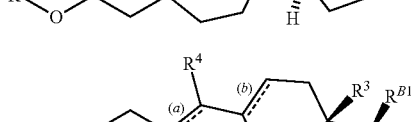

wherein $R^O$ is —C(=O)$R^A$, or a pharmaceutically acceptable salt thereof, and treating the compound of Formula (E') or (E") with a compound of formula NHR$^1$R$^2$, to provide a compound of Formula (A') or (A").

In certain embodiments, the compound of Formula (E') or (E") wherein $R^O$ is —C(=O)$R^A$ is generated in situ from the activation of a compound of Formula (D') or (D") with a compound of formula $R^O$-LG. In certain embodiments, the compound of Formula (E') or (E") is a compound of Formula (E-1') or (E-1"), and the method generates a compound of Formula (A-2') or (A-2") as the major isomer. In certain embodiments, the compound of Formula (E') or (E") is a compound of Formula (E-2') or (E-2"), and the method generates a compound of Formula (A-1') or (A-1") as the major isomer.

In another aspect, provided is method of preparing a compound of Formula (G1):

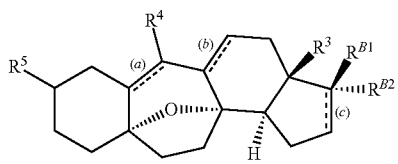

(G1)

or a pharmaceutically acceptable salt, quaternary amine salt, or N-oxide thereof; the method comprising reducing a compound of Formula (B'):

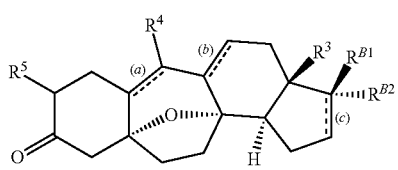

(B')

or a pharmaceutically acceptable salt, quaternary amine salt, or N-oxide thereof.

In another aspect, provided is method of preparing a compound of Formula (G2):

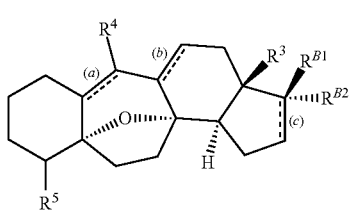

(G2)

or a pharmaceutically acceptable salt, quaternary amine salt, or N-oxide thereof; the method comprising reducing a compound of Formula (B"):

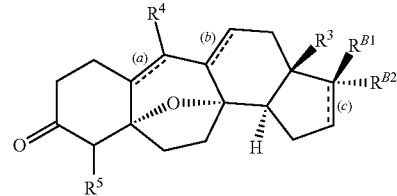

(B")

or a pharmaceutically acceptable salt, quaternary amine salt, or N-oxide thereof.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula:

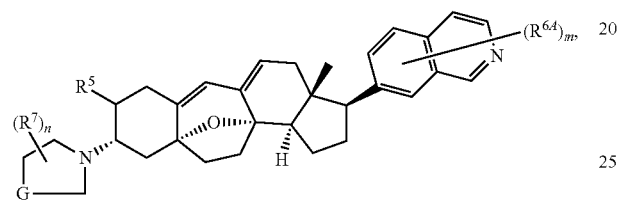

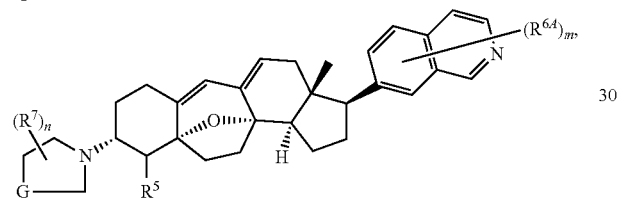

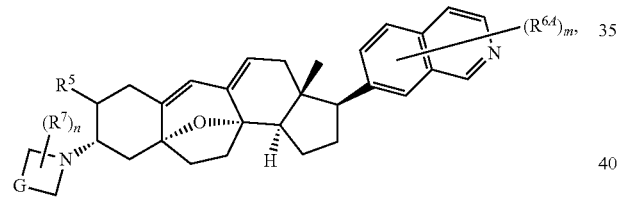

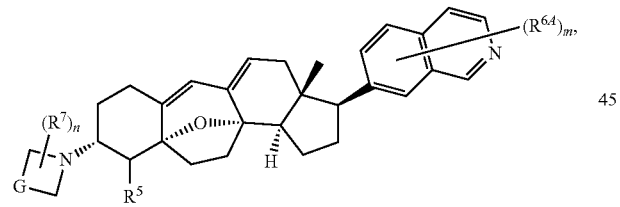

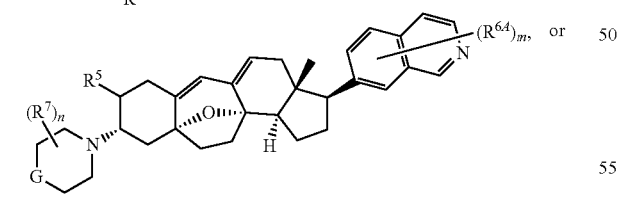

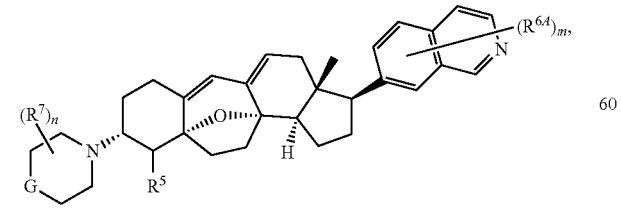

or a pharmaceutically acceptable salt, quaternary amine salt, or N-oxide thereof;

wherein:

m is 0, 1, 2, 3, or 4;

n is 0, 1, or 2;

G is —NH—, —NR'—, —CH$_2$—, —CH(R$^7$)—, or —C(R$^7$)$_2$—;

R$^5$ is —OR$^A$, —OC(=O)R$^A$, —OC(=O)OR$^A$, —OC(=O)N(R$^A$)$_2$, —OS(=O)$_2$R$^A$, —N$^3$, —N(R$^A$)$_2$, —NR$^A$C(=O)R$^A$, —NR$^A$C(=O)R$^A$, —NR$^A$C(=O)N(R$^A$)$_2$, or —NR$^A$S(=O)$_2$R$^A$;

each instance of R$^7$ is independently amino, hydroxyl, halogen, alkyl, alkenyl, alkynyl, carbocyclyl, heterocyclyl, aryl, heteroaryl, or carbonyl;

optionally wherein two R$^7$ groups are joined to form a carbocyclyl, a heterocyclyl, an aryl, a heteroaryl ring, or an oxo (=O) group;

each instance of R$^A$ is independently hydrogen, alkyl, alkenyl, alkynyl, carbocyclyl, heterocyclyl, aryl, heteroaryl, or carbonyl; optionally when attached to N the two R$^A$ groups may be joined to form heterocyclyl or heteroaryl ring;

each instance of R$^{6A}$ is independently halogen, —NO$_2$, —CN, —OR$^{6C}$, SR$^{6C}$, N(R$^{6C}$)$_2$, —C(=O)R$^{6C}$, —C(=O)OR$^{6C}$, —C(=O)N(R$^{6C}$)$_2$, alkyl, alkenyl, alkynyl, carbocyclyl, heterocyclyl, aryl, or heteroaryl;

each instance of R$^{6C}$ is independently hydrogen, alkyl, alkenyl, alkynyl, carbocyclyl, heterocyclyl, aryl, or heteroaryl;

wherein two R$^{6C}$ groups attached to N may optionally be joined to form a heterocyclyl or heteroaryl ring.

2. The compound of claim 1 of Formula:

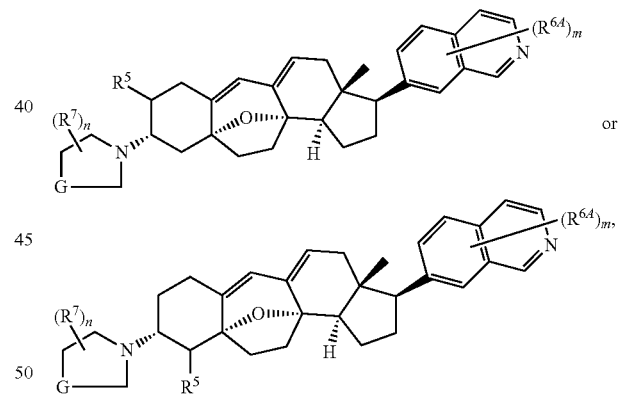

or a pharmaceutically acceptable salt or quaternary amine salt thereof.

3. The compound of claim 2, wherein m and n are independently 0, 1, or 2.

4. The compound of claim 3, wherein m is 0 and n is 1.

5. The compound of claim 4, wherein G is —CH$_2$—, —CH(R$^7$)—, or —C(R$^7$)$_2$—, and each instance of R$^7$ is independently hydroxyl, amino, or halogen.

6. The compound of claim 5, wherein G is —CH(R$^7$)— and each instance of R$^7$ is hydroxyl.

7. The compound of claim 3, wherein m is 0 and n is 0.

8. The compound of claim 7, wherein G is —CH(R$^7$)— and R$^7$ is amino.

9. The compound of claim 1 of Formula:

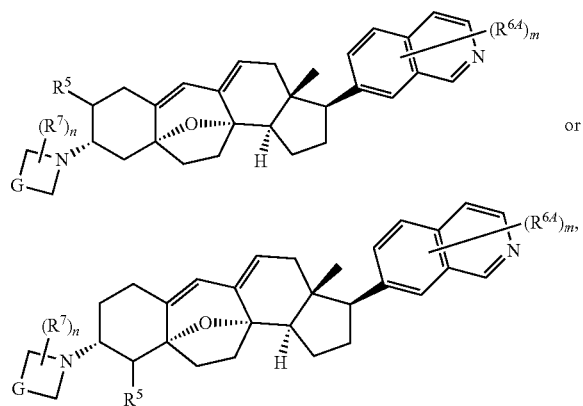

or a pharmaceutically acceptable salt or quaternary amine salt thereof.

10. The compound of claim 9, wherein m and n are independently 0, 1, or 2.

11. The compound of claim 10, wherein m and n are 0.

12. The compound of claim 11, wherein G is —CH$_2$—, —CH(R$^7$)—, or —C(R$^7$)$_2$—, and R$^7$ is hydroxyl, amino, or halogen.

13. The compound of claim 12, wherein G is —CH(R$^7$)—, and R$^7$ is hydroxyl.

14. The compound of claim 12, wherein G is —CH(R$^7$)—, and R$^7$ is amino.

15. The compound of claim 1 of Formula:

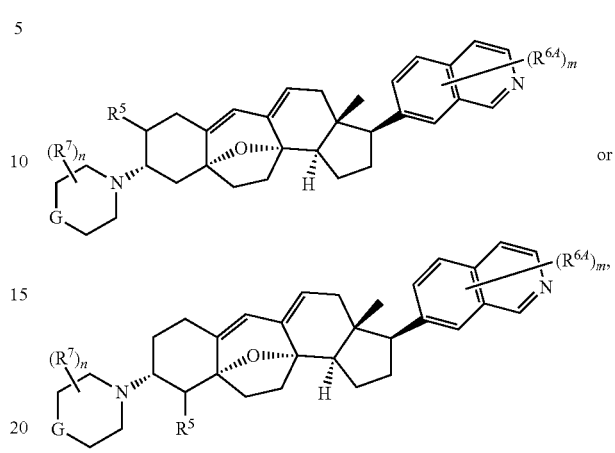

or a pharmaceutically acceptable salt or quaternary amine salt thereof.

16. A pharmaceutical composition comprising a compound according to claim 1 or a pharmaceutically acceptable salt thereof, and a pharmaceutically acceptable excipient.

17. The pharmaceutical composition of claim 16, wherein the composition is suitable for administration to a human.

* * * * *